US012773186B2

(12) United States Patent
Miller et al.

(10) Patent No.: US 12,773,186 B2
(45) Date of Patent: Oct. 27, 2026

(54) HISTOTRIPSY SYSTEMS AND METHODS

(71) Applicant: HistoSonics, Inc., Plymouth, MN (US)

(72) Inventors: Ryan M. Miller, Saline, MI (US); Viktor Bollen, Chelsea, MI (US); Mathew A. Rootes, Plymouth, MN (US); Evan J. McNamara, Saint Louis Park, MN (US); Aleksandra Rakic, Ann Arbor, MI (US); Carolyn M. Turner, Minneapolis, MN (US); Joshua Stopek, Minneapolis, MN (US)

(73) Assignee: HistoSonics, Inc., Plymouth, MN (US)

( * ) Notice: Subject to any disclaimer, the term of this patent is extended or adjusted under 35 U.S.C. 154(b) by 0 days.

(21) Appl. No.: 18/832,708

(22) PCT Filed: Jan. 24, 2023

(86) PCT No.: PCT/US2023/061171
§ 371 (c)(1),
(2) Date: Jul. 24, 2024

(87) PCT Pub. No.: WO2023/141653
PCT Pub. Date: Jul. 27, 2023

(65) Prior Publication Data

US 2025/0152135 A1 May 15, 2025

Related U.S. Application Data

(60) Provisional application No. 63/302,501, filed on Jan. 24, 2022.

(51) Int. Cl.
*A61B 8/00* (2006.01)
*A61N 7/00* (2006.01)

(52) U.S. Cl.
CPC .......... *A61B 8/4461* (2013.01); *A61B 8/4254* (2013.01); *A61N 7/00* (2013.01);
(Continued)

(58) Field of Classification Search
CPC ....... A61B 8/4254; A61B 34/20; A61B 90/37; A61B 34/10; A61B 34/30; A61B 90/50;
(Continued)

(56) References Cited

U.S. PATENT DOCUMENTS 3,243,497 A 3/1966 Kendall et al.
3,679,021 A 7/1972 Goldberg et al.
(Continued)

FOREIGN PATENT DOCUMENTS

AU 2017222925 B2 11/2021
AU 2023231624 9/2024
(Continued)

OTHER PUBLICATIONS

Kisting et al.; Imaging for targeting, monitoring, and assessment after histotripsy: a non-invasive, non-thermal therapy for cancer; Blood Vessels; vol. 10; pp. 15-21; Mar. 2023.
(Continued)

*Primary Examiner* — Adil Partap S Virk
(74) *Attorney, Agent, or Firm* — Shay Glenn LLP

(57) ABSTRACT

A histotripsy therapy system configured for the treatment of tissue is provided, which may include any number of features. Provided herein are systems and methods that provide efficacious non-invasive and minimally invasive therapeutic, diagnostic and research procedures. In particular, provided herein are systems and methods for acoustically coupling a histotripsy therapy system to the skin of a patient to provide targeted, efficacious histotripsy in a variety of different regions and under a variety of different conditions without causing undesired tissue damage to intervening/non-target tissues or structures.

21 Claims, 20 Drawing Sheets

(52) U.S. Cl.
CPC ................. *A61N 2007/0039* (2013.01); *A61N 2007/0082* (2013.01); *A61N 2007/0091* (2013.01)

(58) Field of Classification Search
CPC .... A61B 2034/2051; A61B 2034/2055; A61B 2034/2059; A61B 2034/2061; A61B 2090/374; A61B 2090/376; A61B 2090/3764; A61B 2090/378; A61B 8/4461–4488; A61N 7/00; A61N 2007/0039; A61N 2007/0082; A61N 2007/0091; A61N 2007/0043; A61N 2007/0056–0091
See application file for complete search history.

(56) References Cited

U.S. PATENT DOCUMENTS 3,693,415 A 9/1972 Whittington
3,879,699 A 4/1975 Pepper
4,016,749 A 4/1977 Wachter
4,024,501 A 5/1977 Herring et al.
4,051,394 A 9/1977 Tieden
4,114,457 A 9/1978 Thun
4,117,446 A 9/1978 Alais
4,266,747 A 5/1981 Souder, Jr. et al.
4,269,174 A 5/1981 Adair
4,277,367 A 7/1981 Madsen et al.
4,351,038 A 9/1982 Alais
4,406,153 A 9/1983 Ophir et al.
4,440,025 A 4/1984 Hayakawa et al.
4,447,031 A 5/1984 Souder, Jr. et al.
4,453,408 A 6/1984 Clayman
4,483,343 A 11/1984 Beyer et al.
4,483,345 A 11/1984 Miwa
4,548,374 A 10/1985 Thompson et al.
4,549,533 A 10/1985 Cain et al.
4,550,606 A 11/1985 Drost
4,551,794 A 11/1985 Sandell
4,575,330 A 3/1986 Hull
4,622,972 A 11/1986 Giebeler, Jr.
4,625,731 A 12/1986 Quedens et al.
4,641,378 A 2/1987 McConnell et al.
4,669,483 A 6/1987 Hepp et al.
4,689,986 A 9/1987 Carson et al.
4,757,820 A 7/1988 Itoh
4,771,787 A * 9/1988 Wurster ............... A61B 8/0833 601/4
4,791,915 A 12/1988 Barsotti et al.
4,819,621 A 4/1989 Ueberle et al.
4,829,491 A 5/1989 Saugeon et al.
4,856,107 A 8/1989 Dory
4,865,042 A 9/1989 Umemura et al.
4,888,746 A 12/1989 Wurster et al.
4,890,267 A 12/1989 Rudolph
4,922,917 A 5/1990 Dory
4,928,672 A 5/1990 Grasser et al.
4,938,217 A 7/1990 Lele
4,957,099 A 9/1990 Hassler
4,973,980 A 11/1990 Howkins et al.
4,984,575 A 1/1991 Uchiyama et al.
4,991,151 A 2/1991 Dory
4,995,012 A 2/1991 Dory
RE33,590 E 5/1991 Dory
5,014,686 A 5/1991 Schafer
5,065,751 A 11/1991 Wolf
5,078,140 A * 1/1992 Kwoh ................... A61B 34/30 901/41
5,080,101 A 1/1992 Dory
5,080,102 A 1/1992 Dory
5,091,893 A 2/1992 Smith et al.
5,092,336 A 3/1992 Fink
5,097,709 A 3/1992 Masuzawa et al.
5,111,822 A 5/1992 Dory
5,143,073 A 9/1992 Dory
5,143,074 A 9/1992 Dory
5,150,711 A 9/1992 Dory
5,158,070 A 10/1992 Dory
5,158,071 A 10/1992 Umemura et al.
5,163,421 A 11/1992 Bernstein et al.
5,165,412 A 11/1992 Okazaki
5,174,294 A 12/1992 Saito et al.
5,195,509 A 3/1993 Rentschler et al.
5,209,221 A 5/1993 Riedlinger
5,215,680 A 6/1993 D'Arrigo
5,219,401 A 6/1993 Cathignol et al.
5,222,806 A 6/1993 Roberts
5,230,340 A 7/1993 Rhyne
5,295,484 A 3/1994 Marcus et al.
5,316,000 A 5/1994 Chapelon et al.
5,354,258 A 10/1994 Dory
5,380,411 A 1/1995 Schlief
5,393,296 A 2/1995 Rattner
5,409,002 A 4/1995 Pell
5,431,621 A 7/1995 Dory
5,435,311 A 7/1995 Umemura et al.
5,443,069 A 8/1995 Schaetzle
5,450,305 A 9/1995 Boys et al.
5,469,852 A 11/1995 Nakamura et al.
5,474,071 A 12/1995 Chapelon et al.
5,474,531 A 12/1995 Carter
5,490,051 A 2/1996 Messana
5,492,126 A 2/1996 Hennige et al.
5,501,655 A 3/1996 Rolt et al.
5,520,188 A 5/1996 Hennige et al.
5,523,058 A 6/1996 Umemura et al.
5,524,620 A 6/1996 Rosenschein
5,524,875 A 6/1996 Thommen, Jr.
5,540,909 A 7/1996 Schutt
5,542,935 A 8/1996 Unger et al.
5,558,092 A 9/1996 Unger et al.
5,563,346 A 10/1996 Bartelt et al.
5,566,675 A 10/1996 Li et al.
5,573,497 A 11/1996 Chapelon
5,580,575 A 12/1996 Unger et al.
5,582,578 A 12/1996 Zhong et al.
5,590,657 A 1/1997 Cain et al.
5,601,526 A 2/1997 Chapelon et al.
5,617,862 A 4/1997 Cole et al.
5,648,098 A 7/1997 Porter
5,665,054 A 9/1997 Dory
5,666,954 A 9/1997 Chapelon et al.
5,676,452 A 10/1997 Scholz
5,676,692 A 10/1997 Sanghvi et al.
5,678,554 A 10/1997 Hossack et al.
5,683,064 A 11/1997 Copeland et al.
5,694,936 A 12/1997 Fujimoto et al.
5,695,460 A 12/1997 Siegel et al.
5,717,657 A 2/1998 Ruffa
5,720,287 A 2/1998 Chapelon et al.
5,722,411 A * 3/1998 Suzuki ................... A61B 5/055 601/3
5,724,972 A 3/1998 Petrofsky
5,743,863 A 4/1998 Chapelon
5,753,929 A 5/1998 Bliss
5,759,162 A 6/1998 Oppelt et al.
5,766,138 A 6/1998 Rattner
5,769,790 A 6/1998 Watkins et al.
5,797,848 A 8/1998 Marian et al.
5,800,365 A 9/1998 Zhong et al.
5,820,623 A 10/1998 Ng
5,823,962 A 10/1998 Schaetzle et al.
5,827,204 A 10/1998 Grandia et al.
5,836,896 A 11/1998 Rosenschein
5,849,727 A 12/1998 Porter et al.
5,873,902 A 2/1999 Sanghvi et al.
5,879,314 A 3/1999 Peterson et al.
5,928,169 A 7/1999 Schitzle et al.
5,932,807 A 8/1999 Mallart
5,947,904 A 9/1999 Hossack et al.
5,984,881 A * 11/1999 Ishibashi .................. A61N 7/00 601/2
6,001,069 A 12/1999 Tachibana et al.

(56) References Cited

U.S. PATENT DOCUMENTS 6,007,499 A 12/1999 Martin et al.
6,022,309 A 2/2000 Celliers et al.
6,036,667 A 3/2000 Manna et al.
6,065,166 A 5/2000 Sharrock et al.
6,088,613 A 7/2000 Unger
6,093,883 A 7/2000 Sanghvi et al.
6,113,558 A 9/2000 Rosenschein et al.
6,126,607 A 10/2000 Whitmore, III et al.
6,128,958 A 10/2000 Cain
6,143,018 A 11/2000 Beuthan et al.
6,165,144 A 12/2000 Talish et al.
6,176,842 B1 1/2001 Tachibana et al.
6,296,619 B1 10/2001 Brisken et al.
6,308,585 B1 10/2001 Nilsson et al.
6,308,710 B1 10/2001 Silva
6,309,355 B1 10/2001 Cain et al.
6,318,146 B1 11/2001 Madsen et al.
6,321,109 B2 11/2001 Ben-Haim et al.
6,338,566 B1 1/2002 Verdier
6,344,489 B1 2/2002 Spears
6,391,020 B1 5/2002 Kurtz et al.
6,413,216 B1 7/2002 Cain et al.
6,419,648 B1 7/2002 Vitek et al.
6,424,885 B1 7/2002 Niemeyer et al.
6,470,204 B1 10/2002 Uzgiris et al.
6,488,639 B1 12/2002 Ribault et al.
6,490,469 B2 12/2002 Candy
6,500,141 B1 12/2002 Irion et al.
6,506,154 B1 1/2003 Ezion et al.
6,506,171 B1 1/2003 Vitek et al.
6,508,774 B1 1/2003 Acker et al.
6,511,428 B1 1/2003 Azuma et al.
6,511,444 B2 1/2003 Hynynen et al.
6,522,142 B1 2/2003 Freundlich
6,524,251 B2 2/2003 Rabiner et al.
6,536,553 B1 3/2003 Scanlon
6,543,272 B1 4/2003 Vitek
6,556,750 B2 4/2003 Constantino et al.
6,559,644 B2 5/2003 Froundlich et al.
6,576,220 B2 6/2003 Unger
6,599,288 B2 7/2003 Maguire et al.
6,607,498 B2 8/2003 Eshel
6,612,988 B2 9/2003 Maor et al.
6,613,004 B1 9/2003 Vitek et al.
6,613,005 B1 9/2003 Friedman et al.
6,626,854 B2 9/2003 Friedman et al.
6,626,855 B1 9/2003 Weng et al.
6,645,162 B2 11/2003 Friedman et al.
6,648,839 B2 11/2003 Manna et al.
6,666,833 B1 12/2003 Friedman et al.
6,685,639 B1 * 2/2004 Wang ...................... A61N 7/02 601/3
6,685,640 B1 2/2004 Fry et al.
6,685,657 B2 2/2004 Jones
6,705,994 B2 3/2004 Vortman et al.
6,719,449 B1 4/2004 Laugharn, Jr. et al.
6,719,694 B2 4/2004 Weng et al.
6,735,461 B2 5/2004 Vitek et al.
6,736,814 B2 5/2004 Manna et al.
6,750,463 B1 6/2004 Riley
6,770,031 B2 8/2004 Hynynen et al.
6,773,401 B1 8/2004 Dreschel et al.
6,775,438 B1 8/2004 Gaedke et al.
6,788,977 B2 9/2004 Fenn et al.
6,790,180 B2 9/2004 Vitek
6,820,160 B1 11/2004 Allman
6,852,082 B2 2/2005 Strickberger et al.
6,869,439 B2 3/2005 White et al.
6,890,332 B2 5/2005 Truckal et al.
6,929,609 B2 8/2005 Asafusa
7,004,282 B2 2/2006 Manna et al.
7,059,168 B2 6/2006 Hibi et al.
7,128,711 B2 10/2006 Medan et al.
7,128,719 B2 10/2006 Rosenberg
7,175,596 B2 2/2007 Vitek et al.
7,175,599 B2 2/2007 Hynynen et al.
7,196,313 B2 3/2007 Quinones
7,223,238 B2 5/2007 Swanbom
7,223,239 B2 5/2007 Schulze et al.
7,258,674 B2 8/2007 Cribbs et al.
7,273,458 B2 9/2007 Prausnitz et al.
7,273,459 B2 9/2007 Desilets et al.
7,300,414 B1 11/2007 Holland et al.
7,311,679 B2 12/2007 Desilets et al.
7,331,951 B2 2/2008 Eshel et al.
7,341,569 B2 3/2008 Soltani et al.
7,347,855 B2 3/2008 Eshel et al.
7,358,226 B2 4/2008 Dayton et al.
7,359,640 B2 4/2008 Onde et al.
7,367,948 B2 5/2008 O'Donnell et al.
7,374,551 B2 5/2008 Liang et al.
7,377,900 B2 5/2008 Vitek et al.
7,429,249 B1 9/2008 Winder et al.
7,431,704 B2 10/2008 Babaev
7,442,168 B2 10/2008 Novak et al.
7,462,488 B2 12/2008 Madsen et al.
7,559,905 B2 7/2009 Kagosaki et al.
7,656,638 B2 2/2010 Laakso et al.
7,695,437 B2 4/2010 Quistgaard et al.
7,714,481 B2 5/2010 Sakai
7,771,359 B2 8/2010 Adam
7,967,763 B2 6/2011 Deem et al.
8,057,408 B2 11/2011 Cain et al.
8,295,912 B2 10/2012 Gertner
8,333,115 B1 12/2012 Garvey et al.
8,337,407 B2 12/2012 Quistgaard et al.
8,342,467 B2 1/2013 Stachowski et al.
8,376,970 B2 2/2013 Babaev
8,539,813 B2 9/2013 Cain et al.
8,568,339 B2 10/2013 Rybyanets
8,636,664 B2 1/2014 Brannan
8,715,187 B2 5/2014 Landberg Davis et al.
8,845,537 B2 9/2014 Tanaka et al.
8,932,239 B2 1/2015 Sokka et al.
9,028,434 B2 5/2015 Tanaka
9,049,783 B2 6/2015 Teofilovic
9,061,131 B2 6/2015 Jahnke et al.
9,144,694 B2 9/2015 Cain
9,220,476 B2 12/2015 Coussios et al.
9,220,574 B2 12/2015 Troesken et al.
9,228,730 B1 1/2016 Inbody
9,302,124 B2 4/2016 Konofagou et al.
9,457,201 B2 10/2016 Hoelscher et al.
9,526,923 B2 12/2016 Jahnke et al.
9,636,133 B2 5/2017 Hall et al.
9,642,634 B2 5/2017 Cain et al.
9,763,688 B2 9/2017 Stulen et al.
9,901,753 B2 2/2018 Cain et al.
9,943,708 B2 4/2018 Roberts et al.
10,022,107 B2 7/2018 Thornton et al.
10,046,179 B2 8/2018 Oskar-Kohler
10,046,181 B2 8/2018 Barthe et al.
10,058,352 B2 8/2018 Carvell et al.
10,071,266 B2 9/2018 Cain
10,130,828 B2 11/2018 Vortman et al.
10,219,815 B2 3/2019 Maxwell et al.
10,293,187 B2 5/2019 Cannata et al.
10,293,374 B2 5/2019 Torashima et al.
10,751,015 B2 8/2020 Anderson et al.
10,751,125 B2 8/2020 Levy et al.
10,765,892 B1 9/2020 Vitek et al.
10,772,646 B2 9/2020 Lu et al.
10,780,298 B2 9/2020 Cain et al.
10,791,991 B2 10/2020 Burkett et al.
10,799,209 B2 10/2020 Lahti et al.
10,806,421 B2 10/2020 Keller
10,820,813 B2 11/2020 Alpert
10,847,264 B2 11/2020 Mansker et al.
10,849,511 B2 12/2020 Tochterman et al.
10,869,603 B2 12/2020 Millett et al.
10,869,633 B2 12/2020 Burkett
10,869,648 B2 12/2020 Hubbard et al.
10,874,353 B2 12/2020 Assif
10,874,409 B2 12/2020 Matsubara et al.

(56) References Cited

U.S. PATENT DOCUMENTS 10,878,586 B2 12/2020 Brokman et al.
10,888,232 B2 1/2021 Anderson et al.
10,893,808 B2 1/2021 Dorando
10,900,933 B2 1/2021 Prus et al.
10,905,394 B2 2/2021 Stigall et al.
10,912,463 B2 2/2021 Davies et al.
10,925,688 B2 2/2021 Millett et al.
10,927,003 B2 2/2021 Millett et al.
10,932,678 B2 3/2021 Burkett
10,939,826 B2 3/2021 Glynn et al.
10,942,022 B2 3/2021 Johansson et al.
10,973,419 B2 4/2021 Cort
10,993,618 B2 5/2021 Mansker et al.
10,993,628 B2 5/2021 Tochterman
10,993,694 B2 5/2021 Meyer et al.
11,000,185 B2 5/2021 Stigall et al.
11,006,840 B2 5/2021 Stigall
11,013,491 B2 5/2021 Rice et al.
11,020,087 B2 6/2021 Hoffman
11,020,089 B2 6/2021 Corl
11,026,591 B2 6/2021 Burkett et al.
11,040,140 B2 6/2021 Unser et al.
11,058,399 B2 7/2021 Xu et al.
11,071,522 B2 7/2021 Hynynen et al.
11,103,731 B2 8/2021 Vortman et al.
11,112,473 B2 9/2021 Assif
11,119,552 B2 9/2021 Spencer et al.
11,120,896 B2 9/2021 Balignasay et al.
11,123,019 B2 9/2021 Merritt et al.
11,123,575 B2 9/2021 Vortman et al.
11,135,454 B2 10/2021 Xu et al.
11,141,063 B2 10/2021 Kemp et al.
11,141,131 B2 10/2021 Stigall et al.
11,160,513 B2 11/2021 Anderson et al.
11,205,507 B2 12/2021 Anderson et al.
11,219,748 B2 1/2022 Burkett et al.
11,224,349 B2 1/2022 Davies et al.
11,224,403 B2 1/2022 Cori
11,224,407 B2 1/2022 Wrolstad et al.
11,234,649 B2 2/2022 Matsubara et al.
11,246,533 B2 2/2022 Henderson et al.
11,246,565 B2 2/2022 Corl
11,253,225 B2 2/2022 Hancock et al.
11,260,160 B2 3/2022 Matsubara et al.
11,272,845 B2 3/2022 Cheline et al.
11,272,904 B2 3/2022 Vortman et al.
11,291,866 B2 4/2022 Levy et al.
11,298,030 B2 4/2022 Davies et al.
11,309,071 B2 4/2022 Anderson
11,311,271 B2 4/2022 Stigall et al.
11,324,410 B2 5/2022 Burkett
11,350,906 B2 6/2022 Castella et al.
11,350,954 B2 6/2022 De Cicco et al.
11,364,042 B2 6/2022 Maxwell et al.
11,369,346 B2 6/2022 De Cicco et al.
11,369,994 B2 6/2022 Greenberg et al.
11,395,638 B2 7/2022 Shin et al.
11,406,334 B2 8/2022 Merritt
11,406,355 B2 8/2022 Hoffman et al.
11,406,498 B2 8/2022 Stigall et al.
11,408,987 B2 8/2022 Vignon et al.
11,413,017 B2 8/2022 Stigall et al.
11,419,580 B2 8/2022 Stigall et al.
11,426,140 B2 8/2022 Sudol et al.
11,432,795 B2 9/2022 Merritt
11,432,900 B2 9/2022 Rakic et al.
11,446,000 B2 9/2022 Minas et al.
11,452,496 B2 9/2022 Minas et al.
11,452,506 B2 9/2022 Perez et al.
11,471,215 B2 10/2022 Stigall et al.
11,484,294 B2 11/2022 Hancock et al.
11,510,632 B2 11/2022 Begin et al.
11,517,291 B2 12/2022 Kantor et al.
11,520,874 B2 12/2022 Kennedy et al.
11,524,183 B1 12/2022 Garcia Gutierrez et al.
11,527,001 B2 12/2022 Brokman et al.
11,547,389 B2 1/2023 Shin et al.
11,553,889 B2 1/2023 Spencer et al.
11,554,386 B2 1/2023 Pernot et al.
11,559,207 B2 1/2023 Stigall et al.
11,567,153 B2 1/2023 Stormont et al.
11,576,649 B2 2/2023 Corl
11,576,652 B2 2/2023 De Cicco et al.
11,583,193 B2 2/2023 Groenland et al.
11,589,835 B2 2/2023 Stigall et al.
11,596,351 B2 3/2023 Nair
11,596,384 B2 3/2023 Nair et al.
11,596,385 B2 3/2023 Stigall et al.
11,596,387 B2 3/2023 Song
11,596,389 B2 3/2023 Nair
11,596,469 B2 3/2023 Nair
11,622,746 B2 4/2023 Minas et al.
11,638,576 B2 5/2023 Groenland et al.
11,647,989 B2 5/2023 Hope Simpson et al.
11,648,424 B2 5/2023 Cannata et al.
11,653,895 B2 5/2023 Stigall et al.
11,660,070 B2 5/2023 Stigall et al.
11,666,245 B2 6/2023 Rajguru et al.
11,666,307 B2 6/2023 Unser
11,672,433 B2 6/2023 Park et al.
11,672,552 B2 6/2023 Pasquino et al.
11,672,953 B2 6/2023 May
11,684,342 B2 6/2023 Groenland et al.
11,684,807 B2 6/2023 Vortman et al.
11,701,134 B2 7/2023 Maxwell et al.
11,707,207 B2 7/2023 Stigall et al.
11,707,254 B2 7/2023 Di Tuillio et al.
11,733,881 B2 8/2023 Perez
11,737,728 B2 8/2023 Davies et al.
11,744,527 B2 9/2023 Scott et al.
11,744,547 B2 9/2023 Hynynen
11,759,169 B2 9/2023 Cor
11,759,174 B2 9/2023 Saroha et al.
11,766,237 B2 9/2023 Anderson
11,771,370 B2 10/2023 Hynynen
11,771,405 B2 10/2023 Rhodes
11,771,869 B2 10/2023 Cicco
11,779,307 B2 10/2023 Norris et al.
11,806,167 B2 11/2023 Burkett
11,813,484 B2 11/2023 Cannata et al.
11,813,485 B2 11/2023 Xu et al.
11,819,712 B2 11/2023 Cain et al.
11,854,687 B2 12/2023 Keller
11,857,362 B2 1/2024 Wrolstad et al.
11,857,807 B2 1/2024 Levy et al.
11,864,918 B2 1/2024 Burkett et al.
11,872,412 B2 1/2024 Vortman et al.
11,879,973 B2 1/2024 Prus et al.
11,883,235 B2 1/2024 Stigall et al.
11,890,025 B2 2/2024 Stigall et al.
11,890,136 B2 2/2024 Stigall et al.
11,890,137 B2 2/2024 Jenkins et al.
11,950,954 B2 4/2024 Hyun et al.
11,959,707 B2 4/2024 Luct et al.
11,963,822 B2 4/2024 Wrolstad
11,980,778 B2 5/2024 Cannata et al.
11,986,682 B2 5/2024 Prus et al.
11,992,366 B2 5/2024 Stigall et al.
12,017,013 B2 6/2024 Sasamine et al.
12,035,919 B2 7/2024 Unser
12,036,066 B2 7/2024 De Cicco et al.
12,053,194 B2 8/2024 Goertz et al.
12,082,970 B2 9/2024 Goodman
12,096,949 B2 9/2024 Fermi et al.
12,097,072 B2 9/2024 Stigall et al.
12,112,850 B2 10/2024 Kuo et al.
12,115,007 B2 10/2024 Merritt et al.
12,144,677 B2 11/2024 Corl
12,167,931 B2 12/2024 Corl
12,178,642 B2 12/2024 Rajguru et al.
12,178,643 B2 12/2024 Stigall et al.
12,186,130 B2 1/2025 Davies
12,220,259 B2 2/2025 Burkett et al.
12,232,907 B2 2/2025 Chao et al.

(56) References Cited

U.S. PATENT DOCUMENTS

| | | | |
|---|---|---|---|
| 12,246,195 B2 | 3/2025 | Levy et al. | |
| 12,257,461 B2 | 3/2025 | Son et al. | |
| 12,263,035 B2 | 4/2025 | Stigall et al. | |
| 12,295,600 B2 | 5/2025 | Stigall et al. | |
| 12,303,327 B2 | 5/2025 | Stigall et al. | |
| 12,343,198 B2 | 7/2025 | Laroya | |
| 12,402,802 B2 | 9/2025 | Vitek et al. | |
| 12,419,607 B2 | 9/2025 | Rajguru et al. | |
| 12,440,188 B2 | 10/2025 | Chao et al. | |
| 12,465,477 B2 | 11/2025 | Pasquino et al. | |
| 12,490,936 B2 | 12/2025 | Corl | |
| 12,558,473 B2 | 2/2026 | Saroha et al. | |
| 12,611,167 B2 | 4/2026 | Hancock et al. | |
| 2001/0031922 A1* | 10/2001 | Weng .................. | A61B 8/4461 601/3 |
| 2001/0039420 A1 | 11/2001 | Dory | |
| 2001/0041163 A1 | 11/2001 | Sugita | |
| 2002/0045890 A1 | 4/2002 | Celliers et al. | |
| 2002/0078964 A1 | 6/2002 | Kovac et al. | |
| 2002/0099356 A1 | 7/2002 | Unger et al. | |
| 2002/0145091 A1 | 10/2002 | Talish et al. | |
| 2003/0092982 A1 | 5/2003 | Eppstein | |
| 2003/0112922 A1 | 6/2003 | Burdette et al. | |
| 2003/0149352 A1 | 8/2003 | Liang et al. | |
| 2003/0157025 A1 | 8/2003 | Unger et al. | |
| 2003/0169591 A1 | 9/2003 | Cochran | |
| 2003/0181833 A1 | 9/2003 | Faragalla et al. | |
| 2003/0199857 A1 | 10/2003 | Eizenhofer | |
| 2003/0221561 A1 | 12/2003 | Milo | |
| 2003/0236539 A1 | 12/2003 | Rabiner et al. | |
| 2004/0087854 A1* | 5/2004 | Ueda ...................... | A61B 8/461 600/437 |
| 2004/0127815 A1 | 7/2004 | Marchitto et al. | |
| 2004/0138563 A1 | 7/2004 | Moehring et al. | |
| 2004/0162571 A1 | 8/2004 | Rabiner et al. | |
| 2004/0164213 A1 | 8/2004 | Stephan | |
| 2004/0236248 A1 | 11/2004 | Svedman | |
| 2004/0243021 A1 | 12/2004 | Murphy et al. | |
| 2004/0249509 A1 | 12/2004 | Rogers et al. | |
| 2004/0260214 A1 | 12/2004 | Echt et al. | |
| 2005/0011296 A1 | 1/2005 | Koseki | |
| 2005/0020945 A1 | 1/2005 | Tosaya et al. | |
| 2005/0028289 A1 | 2/2005 | Hakamiun | |
| 2005/0038339 A1 | 2/2005 | Chauhan et al. | |
| 2005/0038361 A1 | 2/2005 | Zhong et al. | |
| 2005/0119572 A1 | 6/2005 | Angelsen et al. | |
| 2005/0121734 A1 | 6/2005 | Degertekin et al. | |
| 2005/0152561 A1 | 7/2005 | Spencer | |
| 2005/0154314 A1 | 7/2005 | Quistgaard | |
| 2005/0154431 A1 | 7/2005 | Quistgaard et al. | |
| 2005/0203399 A1 | 9/2005 | Vaezy et al. | |
| 2005/0215901 A1 | 9/2005 | Anderson et al. | |
| 2005/0234438 A1 | 10/2005 | Mast et al. | |
| 2005/0283098 A1 | 12/2005 | Conston et al. | |
| 2006/0058678 A1 | 3/2006 | Vitek et al. | |
| 2006/0060991 A1 | 3/2006 | Holsteyns et al. | |
| 2006/0074303 A1 | 4/2006 | Chornenky et al. | |
| 2006/0089636 A1 | 4/2006 | Christopherson et al. | |
| 2006/0173321 A1 | 8/2006 | Kubota et al. | |
| 2006/0173387 A1 | 8/2006 | Hansmann et al. | |
| 2006/0184166 A1 | 8/2006 | Valle et al. | |
| 2006/0206028 A1 | 9/2006 | Lee et al. | |
| 2006/0229659 A1 | 10/2006 | Gifford et al. | |
| 2006/0241466 A1 | 10/2006 | Ottoboni et al. | |
| 2006/0241523 A1 | 10/2006 | Sinelnikov et al. | |
| 2006/0241533 A1 | 10/2006 | Geller | |
| 2006/0264760 A1 | 11/2006 | Liu et al. | |
| 2006/0293598 A1 | 12/2006 | Fraser | |
| 2006/0293630 A1 | 12/2006 | Manna et al. | |
| 2007/0004984 A1 | 1/2007 | Crum et al. | |
| 2007/0010805 A1 | 1/2007 | Fedewa et al. | |
| 2007/0016039 A1 | 1/2007 | Vortman et al. | |
| 2007/0044562 A1 | 3/2007 | Sarr | |
| 2007/0065420 A1 | 3/2007 | Johnson | |
| 2007/0083120 A1 | 4/2007 | Cain et al. | |
| 2007/0140413 A1 | 6/2007 | Saracen | |
| 2007/0161902 A1 | 7/2007 | Dan | |
| 2007/0167764 A1 | 7/2007 | Hynynen | |
| 2007/0205785 A1 | 9/2007 | Nilsson | |
| 2007/0219448 A1 | 9/2007 | Seip et al. | |
| 2007/0239001 A1 | 10/2007 | Mehl et al. | |
| 2007/0270683 A1 | 11/2007 | Meloy | |
| 2007/0293762 A1 | 12/2007 | Sawada et al. | |
| 2008/0013593 A1 | 1/2008 | Kawabata | |
| 2008/0033297 A1 | 2/2008 | Sliwa | |
| 2008/0033417 A1 | 2/2008 | Nields et al. | |
| 2008/0051656 A1 | 2/2008 | Vaezy et al. | |
| 2008/0055003 A1 | 3/2008 | Unnikrishnan et al. | |
| 2008/0082026 A1 | 4/2008 | Schmidt et al. | |
| 2008/0091125 A1 | 4/2008 | Owen et al. | |
| 2008/0126665 A1 | 5/2008 | Burr et al. | |
| 2008/0152867 A1 | 6/2008 | Di Pede | |
| 2008/0154132 A1 | 6/2008 | Hall et al. | |
| 2008/0167555 A1* | 7/2008 | Qian ........................ | A61N 7/02 600/439 |
| 2008/0177180 A1 | 7/2008 | Azhari et al. | |
| 2008/0183076 A1 | 7/2008 | Witte et al. | |
| 2008/0194965 A1 | 8/2008 | Sliwa et al. | |
| 2008/0214964 A1 | 9/2008 | Chapelon et al. | |
| 2008/0262345 A1 | 10/2008 | Fichtinger et al. | |
| 2008/0262486 A1 | 10/2008 | Zvuloni et al. | |
| 2008/0269614 A1 | 10/2008 | Adachi et al. | |
| 2008/0283303 A1 | 11/2008 | Cote | |
| 2008/0300485 A1 | 12/2008 | Liu et al. | |
| 2008/0312561 A1 | 12/2008 | Chauhan | |
| 2008/0319376 A1 | 12/2008 | Wilcox et al. | |
| 2009/0012514 A1 | 1/2009 | Moonen et al. | |
| 2009/0030339 A1 | 1/2009 | Cheng et al. | |
| 2009/0036773 A1 | 2/2009 | Lau et al. | |
| 2009/0099482 A1 | 4/2009 | Furuhata et al. | |
| 2009/0112098 A1 | 4/2009 | Vaezy et al. | |
| 2009/0171254 A1 | 7/2009 | Kushculey et al. | |
| 2009/0198094 A1 | 8/2009 | Fenster et al. | |
| 2009/0211587 A1 | 8/2009 | Lawrentschuk | |
| 2009/0227874 A1 | 9/2009 | Suri et al. | |
| 2009/0230822 A1 | 9/2009 | Kushculey et al. | |
| 2009/0230823 A1 | 9/2009 | Kushculey et al. | |
| 2009/0254008 A1 | 10/2009 | Shields, Jr. | |
| 2009/0287083 A1 | 11/2009 | Kushculey et al. | |
| 2009/0306502 A1 | 12/2009 | Lacoste | |
| 2010/0011845 A1 | 1/2010 | Laugharn et al. | |
| 2010/0042020 A1 | 2/2010 | Ben-Ezra | |
| 2010/0056924 A1 | 3/2010 | Powers | |
| 2010/0059264 A1 | 3/2010 | Hasegawa et al. | |
| 2010/0069797 A1 | 3/2010 | Cain et al. | |
| 2010/0125225 A1 | 5/2010 | Gelbart et al. | |
| 2010/0152624 A1 | 6/2010 | Tanis et al. | |
| 2010/0163694 A1 | 7/2010 | Fadler et al. | |
| 2010/0204578 A1 | 8/2010 | Schmidt et al. | |
| 2010/0210940 A1 | 8/2010 | Bradley et al. | |
| 2010/0241005 A1 | 9/2010 | Darlington et al. | |
| 2010/0251823 A1 | 10/2010 | Adachi et al. | |
| 2010/0255623 A1 | 10/2010 | Huang | |
| 2010/0261994 A1 | 10/2010 | Davalos et al. | |
| 2010/0274136 A1 | 10/2010 | Cerofolini | |
| 2010/0280374 A1 | 11/2010 | Roberts et al. | |
| 2010/0286518 A1 | 11/2010 | Lee et al. | |
| 2010/0286519 A1 | 11/2010 | Lee et al. | |
| 2010/0298744 A1 | 11/2010 | Altshuler et al. | |
| 2010/0305432 A1 | 12/2010 | Duhay et al. | |
| 2010/0317971 A1 | 12/2010 | Fan et al. | |
| 2010/0318002 A1 | 12/2010 | Prus et al. | |
| 2011/0072970 A1 | 3/2011 | Slobodzian et al. | |
| 2011/0112400 A1 | 5/2011 | Emery et al. | |
| 2011/0118600 A1 | 5/2011 | Gertner | |
| 2011/0118602 A1 | 5/2011 | Weng et al. | |
| 2011/0144490 A1 | 6/2011 | Davis et al. | |
| 2011/0144545 A1 | 6/2011 | Fan et al. | |
| 2011/0172529 A1 | 7/2011 | Gertner | |
| 2011/0178444 A1 | 7/2011 | Slayton et al. | |
| 2011/0208059 A1 | 8/2011 | Cerofolini | |
| 2011/0245671 A1 | 10/2011 | Sato | |
| 2011/0251528 A1 | 10/2011 | Canney et al. | |
| 2011/0257524 A1 | 10/2011 | Gertner | |

(56) References Cited

U.S. PATENT DOCUMENTS

2011/0257561 A1 10/2011 Gertner et al.
2011/0263967 A1 10/2011 Bailey et al.
2011/0270136 A1 11/2011 Vitek et al.
2011/0302719 A1 12/2011 Schwirian et al.
2011/0319765 A1 12/2011 Gertner
2011/0319927 A1 12/2011 Nita
2012/0029337 A1 2/2012 Aoyagi
2012/0029353 A1 2/2012 Slayton et al.
2012/0029393 A1* 2/2012 Lee .................... A61B 8/4444 601/2
2012/0046592 A1 2/2012 Albright et al.
2012/0059264 A1 3/2012 Hope Simpson et al.
2012/0059285 A1 3/2012 Soltani et al.
2012/0065492 A1 3/2012 Gertner et al.
2012/0065493 A1 3/2012 Gertner
2012/0065494 A1 3/2012 Gertner et al.
2012/0092724 A1 4/2012 Pettis
2012/0101412 A1 4/2012 Vortman et al.
2012/0111339 A1 5/2012 Barthe et al.
2012/0130288 A1 5/2012 Holland et al.
2012/0136279 A1 5/2012 Tanaka et al.
2012/0158013 A1 6/2012 Stefanchik et al.
2012/0172720 A1 7/2012 Asami et al.
2012/0189998 A1 7/2012 Kruecker et al.
2012/0215157 A1 8/2012 Berryman et al.
2012/0232388 A1 9/2012 Curra et al.
2012/0253176 A1 10/2012 Dumoulin
2012/0259250 A1 10/2012 Sapozhnikov et al.
2012/0271167 A1 10/2012 Holland et al.
2012/0271223 A1 10/2012 Khanna
2012/0281902 A1 11/2012 Oikawa et al.
2013/0051178 A1 2/2013 Rybyanets
2013/0053691 A1 2/2013 Kawabata et al.
2013/0090579 A1 4/2013 Cain et al.
2013/0102932 A1 4/2013 Cain et al.
2013/0144165 A1 6/2013 Ebbini et al.
2013/0144194 A1 6/2013 Ahn et al.
2013/0172739 A1 7/2013 Paladini
2013/0190623 A1 7/2013 Bertolina et al.
2013/0190661 A1 7/2013 Wing et al.
2013/0255426 A1 10/2013 Kassow et al.
2013/0257224 A1 10/2013 Wodnicki et al.
2013/0261467 A1 10/2013 Dausch et al.
2013/0267853 A1 10/2013 Dausch et al.
2013/0303906 A1 11/2013 Cain et al.
2013/0338485 A1 12/2013 Mougenot et al.
2014/0005521 A1 1/2014 Kohler et al.
2014/0030806 A1 1/2014 Dudley et al.
2014/0039358 A1 2/2014 Zhou et al.
2014/0046181 A1 2/2014 Benchimol et al.
2014/0058293 A1 2/2014 Hynynen et al.
2014/0058294 A1 2/2014 Gross et al.
2014/0073995 A1 3/2014 Teofilovic et al.
2014/0074076 A1 3/2014 Gertner
2014/0088613 A1 3/2014 Seo et al.
2014/0100459 A1 4/2014 Xu et al.
2014/0112107 A1 4/2014 Guo et al.
2014/0128734 A1 5/2014 Genstier et al.
2014/0180072 A1 6/2014 Davies
2014/0180273 A1 6/2014 Nair
2014/0200489 A1 7/2014 Behar et al.
2014/0243664 A1 8/2014 El-Sayed et al.
2014/0257145 A1 9/2014 Emery
2014/0288428 A1 9/2014 Rothberg et al.
2014/0316269 A1 10/2014 Zhang et al.
2014/0324034 A1 10/2014 Assaf et al.
2014/0330124 A1 11/2014 Carol
2014/0378832 A1 12/2014 Sanghvi et al.
2014/0378964 A1 12/2014 Pearson
2015/0011875 A1 1/2015 Noordhoek et al.
2015/0063668 A1 3/2015 You et al.
2015/0073261 A1 3/2015 Kohler et al.
2015/0080926 A1 3/2015 Emery
2015/0112235 A1 4/2015 Brasset et al.
2015/0148659 A1 5/2015 Vahala
2015/0151141 A1 6/2015 Arnal et al.
2015/0190121 A1 7/2015 Slayton et al.
2015/0190659 A1 7/2015 Kolher
2015/0196239 A1 7/2015 Meehan et al.
2015/0224347 A1 8/2015 Barthe et al.
2015/0257779 A1 9/2015 Sinelnikov et al.
2015/0258352 A1 9/2015 Lin et al.
2015/0265243 A1 9/2015 Kelly
2015/0273246 A1 10/2015 Darlington et al.
2015/0297177 A1 10/2015 Boctor et al.
2015/0305710 A1 10/2015 Stigal et al.
2016/0004933 A1 1/2016 Hu et al.
2016/0038665 A1 2/2016 Schaefer et al.
2016/0114194 A1 4/2016 Gertner
2016/0120572 A1 5/2016 Lee
2016/0135782 A1 5/2016 Chen et al.
2016/0151618 A1 6/2016 Powers et al.
2016/0184614 A1 6/2016 Matula et al.
2016/0206341 A1 7/2016 Slayton
2016/0206867 A1 7/2016 Hossack et al.
2016/0249859 A1 9/2016 Babkin et al.
2016/0287909 A1 10/2016 Maxwell et al.
2016/0303166 A1 10/2016 Katz et al.
2016/0331583 A1 11/2016 Geringer
2016/0331585 A1 11/2016 Kim
2016/0339273 A1 11/2016 Al Mayiah
2016/0345938 A1 12/2016 Tanter et al.
2016/0354087 A1 12/2016 Noonan et al.
2016/0361574 A1 12/2016 Barthe et al.
2017/0000376 A1 1/2017 Partanen et al.
2017/0042521 A1 2/2017 Popovic et al.
2017/0049463 A1 2/2017 Popovic et al.
2017/0065835 A1* 3/2017 Park .................... A61B 5/0042
2017/0071515 A1 3/2017 Chevillet et al.
2017/0072227 A1 3/2017 Khokhlova et al.
2017/0072228 A1 3/2017 Wang et al.
2017/0079519 A1 3/2017 Sung et al.
2017/0100145 A1 4/2017 Khoklova et al.
2017/0120080 A1 5/2017 Phillips et al.
2017/0165046 A1 6/2017 Johnson et al.
2017/0183062 A1 6/2017 Lee
2017/0197099 A1 7/2017 Ruebel et al.
2017/0232277 A1 8/2017 Hall et al.
2017/0263846 A1 9/2017 Nakamura et al.
2017/0281983 A1 10/2017 Marquet et al.
2017/0326589 A1 11/2017 Sudol
2018/0000444 A1 1/2018 Dayton et al.
2018/0008787 A1 1/2018 Schriver et al.
2018/0028841 A1 2/2018 Konofagou et al.
2018/0064412 A1 3/2018 Messas et al.
2018/0161086 A1 6/2018 Davalos et al.
2018/0169444 A1 6/2018 Averkiou et al.
2018/0206816 A1 7/2018 Prus et al.
2018/0207029 A1 7/2018 Herekar et al.
2018/0236271 A1 8/2018 Tanter et al.
2018/0317884 A1 11/2018 Chapelon et al.
2018/0374471 A1 12/2018 Dirksen et al.
2019/0000422 A1 1/2019 West et al.
2019/0023804 A1 1/2019 Onik et al.
2019/0062761 A1 2/2019 Janovjak et al.
2019/0082998 A1 3/2019 Nowroozi et al.
2019/0105113 A1 4/2019 Popovic et al.
2019/0126317 A1* 5/2019 Pernot .................. A61B 8/4461
2019/0275353 A1 9/2019 Cannata et al.
2019/0282294 A1 9/2019 Davalos et al.
2019/0314045 A1 10/2019 Cunitz et al.
2019/0320904 A1 10/2019 Mei
2019/0323086 A1 10/2019 Leuthardt et al.
2019/0328500 A1 10/2019 Cichon et al.
2020/0010575 A1 1/2020 Hode et al.
2020/0037990 A1 2/2020 Qiao et al.
2020/0055085 A1 2/2020 Taffier
2020/0078608 A1 3/2020 Maxwell et al.
2020/0107843 A1 4/2020 Goertz et al.
2020/0182989 A1 6/2020 Freeman et al.
2020/0194117 A1 6/2020 Krieger et al.
2020/0253550 A1 8/2020 Nair
2020/0254285 A1 8/2020 Jang et al.
2020/0260964 A1 8/2020 Collins et al.

(56) References Cited

U.S. PATENT DOCUMENTS

| | | | |
|---|---|---|---|
| 2020/0282239 | A1 | 9/2020 | Beder et al. |
| 2020/0289080 | A1 | 9/2020 | Yang et al. |
| 2020/0305842 | A1 | 10/2020 | Rosenzweig et al. |
| 2020/0308785 | A1 | 10/2020 | Sennhauser |
| 2020/0323515 | A1 | 10/2020 | Levy |
| 2020/0330039 | A1 | 10/2020 | Burkett et al. |
| 2020/0330075 | A1 | 10/2020 | O'Reilly et al. |
| 2020/0346044 | A1 | 11/2020 | Woodcare et al. |
| 2020/0353293 | A1 | 11/2020 | Khokhlova et al. |
| 2020/0367835 | A1 | 11/2020 | Anderson |
| 2020/0375576 | A1 | 12/2020 | Moulton |
| 2020/0405258 | A1 | 12/2020 | Dayton et al. |
| 2020/0405259 | A1 | 12/2020 | Merritt |
| 2021/0000541 | A1 | 1/2021 | Levy et al. |
| 2021/0009936 | A1 | 1/2021 | Kamen et al. |
| 2021/0022703 | A1 | 1/2021 | Nair |
| 2021/0022714 | A1 | 1/2021 | Zagrodsky et al. |
| 2021/0100527 | A1 | 4/2021 | Martin |
| 2021/0108866 | A1 | 4/2021 | Lucht et al. |
| 2021/0121122 | A1 | 4/2021 | Melcher et al. |
| 2021/0161398 | A1 | 6/2021 | Millett et al. |
| 2021/0169515 | A1 | 6/2021 | Pahk et al. |
| 2021/0170204 | A1 | 6/2021 | Vortman et al. |
| 2021/0170205 | A1 | 6/2021 | Vortman et al. |
| 2021/0187331 | A1 | 6/2021 | Zadicario et al. |
| 2021/0196295 | A1 | 7/2021 | Goudot et al. |
| 2021/0220607 | A1 | 7/2021 | Sasamine et al. |
| 2021/0330294 | A1 | 10/2021 | Hynynen et al. |
| 2021/0353161 | A1 | 11/2021 | Merritt et al. |
| 2021/0386451 | A1 | 12/2021 | Escudero et al. |
| 2021/0401366 | A1 | 12/2021 | Weiss et al. |
| 2021/0401400 | A1 | 12/2021 | Sheehan et al. |
| 2022/0008036 | A1 | 1/2022 | Gulsen et al. |
| 2022/0022845 | A1 | 1/2022 | Cori |
| 2022/0031287 | A1 | 2/2022 | Ebbini et al. |
| 2022/0043143 | A1 | 2/2022 | Prus et al. |
| 2022/0059227 | A1 | 2/2022 | Park et al. |
| 2022/0079563 | A1 | 3/2022 | Kemp |
| 2022/0087640 | A1 | 3/2022 | Minas et al. |
| 2022/0110809 | A1 | 4/2022 | Grindstaff et al. |
| 2022/0166462 | A1 | 5/2022 | Deurenberg et al. |
| 2022/0167920 | A1 | 6/2022 | Margolis |
| 2022/0168470 | A1 | 6/2022 | Ricotti et al. |
| 2022/0196771 | A1 | 6/2022 | Zur et al. |
| 2022/0202483 | A1 | 6/2022 | Gertner |
| 2022/0203139 | A1 | 6/2022 | Shapira |
| 2022/0219019 | A1 | 7/2022 | Xu et al. |
| 2022/0233890 | A1 | 7/2022 | Hynynen et al. |
| 2022/0240890 | A1 | 8/2022 | Hancock et al. |
| 2022/0257329 | A1 | 8/2022 | Stigall et al. |
| 2022/0280233 | A1 | 9/2022 | Park et al. |
| 2022/0280367 | A1 | 9/2022 | Diodato et al. |
| 2022/0296211 | A1 | 9/2022 | Saroha et al. |
| 2022/0331611 | A1 | 10/2022 | Razavi et al. |
| 2022/0338750 | A1 | 10/2022 | Allen et al. |
| 2022/0346756 | A1 | 11/2022 | Chen |
| 2022/0361844 | A1* | 11/2022 | Shoudy .................... A61B 8/08 |
| 2022/0370025 | A1 | 11/2022 | Regensburger et al. |
| 2022/0386970 | A1 | 12/2022 | Merritt |
| 2022/0395333 | A1 | 12/2022 | Merritt et al. |
| 2022/0409171 | A1 | 12/2022 | Sudol et al. |
| 2022/0409858 | A1 | 12/2022 | Lin |
| 2023/0000466 | A1 | 1/2023 | Levy et al. |
| 2023/0000469 | A1 | 1/2023 | Prus et al. |
| 2023/0008714 | A1 | 1/2023 | Rajguru et al. |
| 2023/0012365 | A1 | 1/2023 | Alpert et al. |
| 2023/0024998 | A1 | 1/2023 | Greenberg |
| 2023/0031859 | A1 | 2/2023 | Davies et al. |
| 2023/0037603 | A1 | 2/2023 | Pombo et al. |
| 2023/0038498 | A1 | 2/2023 | Xu et al. |
| 2023/0038543 | A1 | 2/2023 | Minas et al. |
| 2023/0042834 | A1 | 2/2023 | Henderson et al. |
| 2023/0045488 | A1 | 2/2023 | Rajguru et al. |
| 2023/0048979 | A1 | 2/2023 | Lindenmoyer et al. |
| 2023/0061534 | A1 | 3/2023 | Stopek |
| 2023/0073447 | A1 | 3/2023 | Minas et al. |
| 2023/0100912 | A1 | 3/2023 | Amar et al. |
| 2023/0112722 | A1 | 4/2023 | Hoffman et al. |
| 2023/0114972 | A1 | 4/2023 | Bigham et al. |
| 2023/0121688 | A1 | 4/2023 | Begin et al. |
| 2023/0126520 | A1 | 4/2023 | Lenich et al. |
| 2023/0129687 | A1 | 4/2023 | Regensburger |
| 2023/0145064 | A1 | 5/2023 | Vortman et al. |
| 2023/0181140 | A1 | 6/2023 | Cohen et al. |
| 2023/0181156 | A1 | 6/2023 | Cohen et al. |
| 2023/0190215 | A1 | 6/2023 | Nachtomy et al. |
| 2023/0190224 | A1 | 6/2023 | Rajguru et al. |
| 2023/0190225 | A1 | 6/2023 | Cohen et al. |
| 2023/0190226 | A1 | 6/2023 | Rajguru et al. |
| 2023/0190227 | A1 | 6/2023 | Cohen et al. |
| 2023/0190228 | A1 | 6/2023 | Cohen et al. |
| 2023/0190229 | A1 | 6/2023 | Cohen et al. |
| 2023/0190230 | A1 | 6/2023 | Yang et al. |
| 2023/0196569 | A1 | 6/2023 | Cohen et al. |
| 2023/0210603 | A1 | 7/2023 | Barrera et al. |
| 2023/0218230 | A1 | 7/2023 | Wu et al. |
| 2023/0218262 | A1 | 7/2023 | Boutelle et al. |
| 2023/0218269 | A1 | 7/2023 | Alpert et al. |
| 2023/0218930 | A1 | 7/2023 | Stopek et al. |
| 2023/0240615 | A1 | 8/2023 | May et al. |
| 2023/0240663 | A1 | 8/2023 | Lafond et al. |
| 2023/0240792 | A1 | 8/2023 | Rakic et al. |
| 2023/0255597 | A1 | 8/2023 | O'Reilly et al. |
| 2023/0260601 | A1 | 8/2023 | Abel et al. |
| 2023/0270388 | A1 | 8/2023 | Richardson et al. |
| 2023/0310899 | A1 | 10/2023 | Hall et al. |
| 2023/0310900 | A1 | 10/2023 | Cannata et al. |
| 2023/0321327 | A1 | 10/2023 | Maxwell et al. |
| 2023/0329559 | A1 | 10/2023 | Xu et al. |
| 2023/0334659 | A1 | 10/2023 | Marama et al. |
| 2023/0334677 | A1 | 10/2023 | Sturm |
| 2023/0338010 | A1 | 10/2023 | Sturm |
| 2023/0372025 | A1 | 11/2023 | Van Der Zaag et al. |
| 2023/0381544 | A1 | 11/2023 | Penot et al. |
| 2023/0389891 | A1 | 12/2023 | Cohen et al. |
| 2023/0398381 | A1 | 12/2023 | Vitek et al. |
| 2024/0000422 | A1 | 1/2024 | Corl |
| 2024/0000426 | A1 | 1/2024 | Davies et al. |
| 2024/0001157 | A1 | 1/2024 | Cannata et al. |
| 2024/0001158 | A1 | 1/2024 | Cannata et al. |
| 2024/0023928 | A1 | 1/2024 | Di Tullio et al. |
| 2024/0023930 | A1 | 1/2024 | Anderson |
| 2024/0023941 | A1 | 1/2024 | Rhodes |
| 2024/0024705 | A1 | 1/2024 | Xu et al. |
| 2024/0033542 | A1 | 2/2024 | Cain et al. |
| 2024/0065632 | A1 | 2/2024 | Burkett |
| 2024/0081754 | A1 | 3/2024 | Regensburger et al. |
| 2024/0138807 | A1 | 5/2024 | Minas |
| 2024/0139552 | A1 | 5/2024 | Duryea et al. |
| 2024/0139553 | A1 | 5/2024 | Miller et al. |
| 2024/0149078 | A1 | 5/2024 | Duryea et al. |
| 2024/0165666 | A1 | 5/2024 | Hynynen et al. |
| 2024/0188929 | A1 | 6/2024 | Minas et al. |
| 2024/0188931 | A1 | 6/2024 | Ossmann et al. |
| 2024/0189267 | A1 | 6/2024 | Bogott et al. |
| 2024/0189627 | A1 | 6/2024 | Bogott et al. |
| 2024/0189628 | A1 | 6/2024 | Grumbir et al. |
| 2024/0207654 | A1 | 6/2024 | Xu et al. |
| 2024/0225592 | A1 | 7/2024 | May et al. |
| 2024/0225671 | A9 | 7/2024 | Maxwell et al. |
| 2024/0245374 | A1 | 7/2024 | Jenkins et al. |
| 2024/0245390 | A1 | 7/2024 | Winkler Brown et al. |
| 2024/0245465 | A1 | 7/2024 | Jenkins et al. |
| 2024/0269491 | A1 | 8/2024 | Xu et al. |
| 2024/0285249 | A1 | 8/2024 | May |
| 2024/0285978 | A1 | 8/2024 | Xu et al. |
| 2024/0299092 | A1 | 9/2024 | Boinagrov et al. |
| 2024/0307027 | A1 | 9/2024 | Minas |
| 2024/0307708 | A1 | 9/2024 | Cannata et al. |
| 2024/0315713 | A1 | 9/2024 | Maxwell et al. |
| 2024/0316367 | A1 | 9/2024 | Cannata et al. |
| 2024/0335680 | A1 | 10/2024 | Achrol et al. |
| 2024/0341732 | A1 | 10/2024 | Hoffman et al. |
| 2024/0350118 | A1 | 10/2024 | Jenkins et al. |

(56) References Cited

U.S. PATENT DOCUMENTS

| | | | |
|---|---|---|---|
| 2024/0374242 | A1 | 11/2024 | Merritt et al. |
| 2024/0408416 | A1 | 12/2024 | Cannata et al. |
| 2025/0040912 | A1 | 2/2025 | Levy et al. |
| 2025/0041577 | A1 | 2/2025 | Shapira et al. |
| 2025/0072872 | A1 | 3/2025 | Nachtomy et al. |
| 2025/0160786 | A1 | 5/2025 | Zagrodsky et al. |
| 2025/0186808 | A1 | 6/2025 | Cannata et al. |
| 2025/0256132 | A1 | 8/2025 | Xu et al. |
| 2025/0263798 | A1 | 8/2025 | Achrol et al. |
| 2025/0320390 | A1 | 10/2025 | Shachaf et al. |
| 2025/0344999 | A1 | 11/2025 | Wu et al. |
| 2025/0349023 | A1 | 11/2025 | Rajguru et al. |
| 2025/0352828 | A1 | 11/2025 | Miller et al. |
| 2026/0076694 | A1 | 3/2026 | Cannata et al. |
| 2026/0115496 | A1 | 4/2026 | Rootes et al. |
| 2026/0124473 | A1 | 5/2026 | Cain et al. |

FOREIGN PATENT DOCUMENTS

| | | | |
|---|---|---|---|
| AU | 2021406651 | B2 | 4/2025 |
| AU | 2022215411 | B2 | 5/2025 |
| BR | 112018017326 | B1 | 12/2022 |
| CA | 3073552 | A1 | 3/2019 |
| CA | 3101381 | A1 | 11/2019 |
| CA | 3055856 | A1 | 4/2020 |
| CA | 3130859 | A1 | 10/2020 |
| CA | 3153080 | A1 | 4/2021 |
| CA | 2910561 | C | 7/2021 |
| CA | 2908740 | C | 10/2021 |
| CA | 2980976 | C | 3/2023 |
| CA | 2840014 | C | 8/2023 |
| CN | 1669672 | A | 9/2005 |
| CN | 1732031 | A | 2/2006 |
| CN | 201197744 | Y | 2/2009 |
| CN | 102292123 | A | 12/2011 |
| CN | 102481164 | A | 5/2012 |
| CN | 102665585 | A | 9/2012 |
| CN | 102740777 | A | 10/2012 |
| CN | 103537016 | A | 1/2014 |
| CN | 103648361 | A | 3/2014 |
| CN | 103812477 | A | 5/2014 |
| CN | 104013444 | A | 9/2014 |
| CN | 104135938 | A | 11/2014 |
| CN | 104208822 | A | 12/2014 |
| CN | 106999076 | B | 8/2017 |
| CN | 109185113 | A | 1/2019 |
| CN | 109689160 | A | 4/2019 |
| CN | 208725992 | U | 4/2019 |
| CN | 111565642 | A | 8/2020 |
| CN | 111655337 | A | 9/2020 |
| CN | 111699022 | A | 9/2020 |
| CN | 111712300 | A | 9/2020 |
| CN | 111712301 | A | 9/2020 |
| CN | 106999053 | B | 10/2020 |
| CN | 107660137 | B | 10/2020 |
| CN | 111757769 | A | 10/2020 |
| CN | 112204412 | A | 1/2021 |
| CN | 112236195 | A | 1/2021 |
| CN | 106661535 | B | 3/2021 |
| CN | 112533673 | A | 3/2021 |
| CN | 112566694 | A | 3/2021 |
| CN | 106999054 | B | 5/2021 |
| CN | 106793997 | B | 6/2021 |
| CN | 107530049 | B | 6/2021 |
| CN | 112912011 | A | 6/2021 |
| CN | 112912012 | A | 6/2021 |
| CN | 112912013 | A | 6/2021 |
| CN | 112969413 | A | 6/2021 |
| CN | 112996445 | A | 6/2021 |
| CN | 113167877 | A | 7/2021 |
| CN | 113196080 | A | 7/2021 |
| CN | 109196369 | B | 8/2021 |
| CN | 109200484 | B | 8/2021 |
| CN | 113316419 | A | 8/2021 |
| CN | 113329788 | A | 8/2021 |
| CN | 109640830 | B | 10/2021 |
| CN | 113473917 | A | 10/2021 |
| CN | 113507946 | A | 10/2021 |
| CN | 113518588 | A | 10/2021 |
| CN | 113705586 | A | 11/2021 |
| CN | 110662575 | B | 12/2021 |
| CN | 113905666 | A | 1/2022 |
| CN | 114222536 | A | 3/2022 |
| CN | 114366154 | A | 4/2022 |
| CN | 114423362 | A | 4/2022 |
| CN | 110248606 | B | 6/2022 |
| CN | 115227992 | A | 10/2022 |
| CN | 109843181 | B | 11/2022 |
| CN | 115461000 | A | 12/2022 |
| CN | 115515504 | A | 12/2022 |
| CN | 109091768 | B | 3/2023 |
| CN | 115779285 | A | 3/2023 |
| CN | 115779287 | A | 3/2023 |
| CN | 115813438 | A | 3/2023 |
| CN | 111032157 | B | 4/2023 |
| CN | 115916035 | A | 4/2023 |
| CN | 110958858 | B | 5/2023 |
| CN | 116172611 | A | 5/2023 |
| CN | 111655337 | B | 6/2023 |
| CN | 109416908 | B | 7/2023 |
| CN | 116507295 | A | 7/2023 |
| CN | 107529989 | B | 8/2023 |
| CN | 111372522 | B | 8/2023 |
| CN | 116617589 | A | 8/2023 |
| CN | 112236195 | B | 9/2023 |
| CN | 114555247 | B | 9/2023 |
| CN | 116744856 | A | 9/2023 |
| CN | 116761554 | A | 9/2023 |
| CN | 109416907 | B | 10/2023 |
| CN | 117321444 | A | 12/2023 |
| CN | 117500437 | A | 2/2024 |
| CN | 117580499 | A | 2/2024 |
| CN | 111212606 | B | 3/2024 |
| CN | 113490459 | B | 5/2024 |
| CN | 118414127 | A | 7/2024 |
| CN | 112601498 | B | 9/2024 |
| CN | 118678921 | A | 9/2024 |
| CN | 113271866 | B | 10/2024 |
| CN | 112603273 | B | 12/2024 |
| CN | 112639754 | B | 12/2024 |
| CN | 119367006 | A | 1/2025 |
| CN | 112704620 | B | 2/2025 |
| CN | 114287963 | B | 2/2025 |
| CN | 110410498 | B | 3/2025 |
| CN | 112426634 | B | 3/2025 |
| CN | 112545816 | B | 5/2025 |
| CN | 112546464 | B | 6/2025 |
| CN | 112618971 | B | 6/2025 |
| CN | 113040905 | B | 6/2025 |
| CN | 114340682 | B | 7/2025 |
| CN | 115515567 | B | 7/2025 |
| CN | 112546465 | B | 8/2025 |
| CN | 309464789 | S | 8/2025 |
| CN | 111991712 | B | 9/2025 |
| CN | 112494106 | B | 10/2025 |
| CN | 114638798 | B | 10/2025 |
| CN | 111388117 | B | 2/2026 |
| CN | 111388121 | B | 2/2026 |
| DE | 3220751 | A1 | 12/1983 |
| DE | 3544628 | A1 | 6/1987 |
| DE | 3817094 | A1 | 11/1989 |
| DE | 4012760 | A1 | 5/1992 |
| DE | 602020055151 | T2 | 7/2025 |
| DE | 602022018890 | T2 | 8/2025 |
| DE | 602020058523 | T2 | 9/2025 |
| DE | 602020059056 | T2 | 9/2025 |
| DE | 602022021590 | T2 | 9/2025 |
| DE | 602017092008 | T2 | 10/2025 |
| DE | 602022022517 | T2 | 10/2025 |
| EP | 0017382 | A1 | 10/1980 |
| EP | 0320303 | A2 | 6/1989 |
| EP | 0332871 | A2 | 9/1989 |
| EP | 0384831 | A2 | 8/1990 |
| EP | 0619156 | A1 | 10/1994 |

(56) References Cited

FOREIGN PATENT DOCUMENTS

| | | | |
|---|---|---|---|
| EP | 0755653 | A1 | 1/1997 |
| EP | 1374785 | A1 | 1/2004 |
| EP | 1504713 | A1 | 2/2005 |
| EP | 1566201 | A2 | 8/2005 |
| EP | 2397188 | A1 | 12/2011 |
| EP | 2934308 | B1 | 10/2015 |
| EP | 2934309 | B1 | 10/2015 |
| EP | 3097180 | B1 | 11/2016 |
| EP | 3100767 | B1 | 11/2019 |
| EP | 2759003 | B1 | 8/2020 |
| EP | 3558457 | A4 | 8/2020 |
| EP | 3700629 | A1 | 9/2020 |
| EP | 3218829 | B1 | 10/2020 |
| EP | 3229688 | B1 | 10/2020 |
| EP | 2887989 | B1 | 2/2021 |
| EP | 3777689 | A1 | 2/2021 |
| EP | 2938253 | B1 | 3/2021 |
| EP | 3076864 | B1 | 3/2021 |
| EP | 2802276 | B1 | 4/2021 |
| EP | 2809221 | B1 | 4/2021 |
| EP | 3801761 | A1 | 4/2021 |
| EP | 3801762 | A2 | 4/2021 |
| EP | 3801763 | A1 | 4/2021 |
| EP | 2967369 | B1 | 5/2021 |
| EP | 2967488 | B1 | 6/2021 |
| EP | 3184048 | B1 | 6/2021 |
| EP | 2967370 | B1 | 9/2021 |
| EP | 3482390 | B1 | 9/2021 |
| EP | 3870067 | A1 | 9/2021 |
| EP | 3870069 | A1 | 9/2021 |
| EP | 3876843 | A1 | 9/2021 |
| EP | 2931130 | B1 | 10/2021 |
| EP | 2934304 | B1 | 10/2021 |
| EP | 3887843 | A1 | 10/2021 |
| EP | 3888534 | A1 | 10/2021 |
| EP | 3895604 | A1 | 10/2021 |
| EP | 3897391 | A1 | 10/2021 |
| EP | 3229672 | B1 | 11/2021 |
| EP | 3902603 | A1 | 11/2021 |
| EP | 3903672 | A1 | 11/2021 |
| EP | 2964096 | B1 | 12/2021 |
| EP | 3930776 | A1 | 1/2022 |
| EP | 3545829 | B1 | 3/2022 |
| EP | 3959530 | A2 | 3/2022 |
| EP | 3060129 | B1 | 4/2022 |
| EP | 3986296 | A1 | 4/2022 |
| EP | 3988167 | A1 | 4/2022 |
| EP | 2914166 | B1 | 5/2022 |
| EP | 3229674 | B1 | 5/2022 |
| EP | 2779907 | B1 | 6/2022 |
| EP | 3102098 | B1 | 6/2022 |
| EP | 2965263 | B1 | 7/2022 |
| EP | 2726152 | B1 | 8/2022 |
| EP | 4042936 | A1 | 8/2022 |
| EP | 3298959 | B2 | 9/2022 |
| EP | 2931131 | B1 | 11/2022 |
| EP | 2938268 | B1 | 11/2022 |
| EP | 3581103 | B1 | 11/2022 |
| EP | 4087492 | A1 | 11/2022 |
| EP | 4093470 | A1 | 11/2022 |
| EP | 3091905 | B1 | 12/2022 |
| EP | 4098203 | A1 | 12/2022 |
| EP | 2950737 | B1 | 1/2023 |
| EP | 3057496 | B1 | 1/2023 |
| EP | 4114274 | A1 | 1/2023 |
| EP | 4117534 | A1 | 1/2023 |
| EP | 2869804 | B1 | 2/2023 |
| EP | 2938265 | B1 | 2/2023 |
| EP | 3024403 | B1 | 3/2023 |
| EP | 4138672 | A1 | 3/2023 |
| EP | 4151156 | A1 | 3/2023 |
| EP | 2938271 | B1 | 4/2023 |
| EP | 4161360 | A1 | 4/2023 |
| EP | 4179995 | A2 | 5/2023 |
| EP | 3171764 | B1 | 6/2023 |
| EP | 4201342 | A1 | 6/2023 |
| EP | 2931132 | B1 | 7/2023 |
| EP | 3229695 | B1 | 7/2023 |
| EP | 4209178 | A1 | 7/2023 |
| EP | 4209179 | A1 | 7/2023 |
| EP | 4226864 | A1 | 8/2023 |
| EP | 4230121 | A2 | 8/2023 |
| EP | 4230146 | A1 | 8/2023 |
| EP | 4233972 | A2 | 8/2023 |
| EP | 2866733 | B1 | 9/2023 |
| EP | 3870069 | B1 | 9/2023 |
| EP | 4247489 | A1 | 9/2023 |
| EP | 3484371 | B1 | 10/2023 |
| EP | 3658037 | B1 | 10/2023 |
| EP | 3685874 | B1 | 10/2023 |
| EP | 3870070 | B1 | 10/2023 |
| EP | 4257151 | A1 | 10/2023 |
| EP | 2938255 | B1 | 11/2023 |
| EP | 3229906 | B1 | 11/2023 |
| EP | 3764914 | B1 | 11/2023 |
| EP | 3903672 | B1 | 11/2023 |
| EP | 4272654 | A2 | 11/2023 |
| EP | 4275609 | A2 | 11/2023 |
| EP | 3316804 | B1 | 12/2023 |
| EP | 3519109 | B1 | 12/2023 |
| EP | 3166479 | B1 | 1/2024 |
| EP | 3537984 | B1 | 1/2024 |
| EP | 3908195 | B1 | 2/2024 |
| EP | 3182920 | B1 | 3/2024 |
| EP | 3174643 | B1 | 4/2024 |
| EP | 3814917 | B1 | 4/2024 |
| EP | 4349283 | A1 | 4/2024 |
| EP | 3681419 | B1 | 5/2024 |
| EP | 4368118 | A2 | 5/2024 |
| EP | 2804525 | B1 | 6/2024 |
| EP | 4380667 | A2 | 6/2024 |
| EP | 4385428 | A1 | 6/2024 |
| EP | 4459545 | A1 | 6/2024 |
| EP | 3324836 | B1 | 9/2024 |
| EP | 3624732 | B1 | 11/2024 |
| EP | 4289415 | A4 | 1/2025 |
| EP | 3190958 | B1 | 2/2025 |
| EP | 4282471 | B1 | 3/2025 |
| EP | 3277378 | B1 | 5/2025 |
| EP | 4041463 | B1 | 8/2025 |
| EP | 3986296 | B1 | 9/2025 |
| EP | 4275744 | B1 | 10/2025 |
| EP | 4633490 | A1 | 10/2025 |
| EP | 4706546 | A2 | 3/2026 |
| ES | 2774069 | T3 | 7/2020 |
| ES | 2819552 | T3 | 4/2021 |
| ES | 2829822 | T3 | 6/2021 |
| ES | 2998435 | T3 | 2/2025 |
| ES | 3005837 | T3 | 3/2025 |
| GB | 2099582 | A | 12/1982 |
| HK | 1245715 | B | 1/2021 |
| IL | 254768 | A | 5/2021 |
| IL | 261285 | B | 2/2022 |
| IN | 202117039853 | A | 12/2021 |
| IN | 387413 | B | 1/2022 |
| IN | 445766 | B | 8/2023 |
| JP | 60-80779 | A | 5/1985 |
| JP | 61-196718 | A | 8/1986 |
| JP | S62144641 | A | 6/1987 |
| JP | S6468249 | A | 3/1989 |
| JP | H02104343 | A | 4/1990 |
| JP | 02-215451 | A | 8/1990 |
| JP | H02246961 | A | 10/1990 |
| JP | H0422351 | A | 1/1992 |
| JP | 06-197907 | A | 7/1994 |
| JP | 07-504339 | A | 5/1995 |
| JP | H07213527 | A | 8/1995 |
| JP | H07284499 | A | 10/1995 |
| JP | 08-84740 | A | 4/1996 |
| JP | 06-304178 | A | 5/1996 |
| JP | 08-131454 | A | 5/1996 |
| JP | 09-55571 | A | 2/1997 |
| JP | H10305041 | A | 11/1998 |
| JP | 10-512477 | A | 12/1998 |

(56) References Cited

FOREIGN PATENT DOCUMENTS

| | | | |
|---|---|---|---|
| JP | 2000300559 | A | 10/2000 |
| JP | 2003510159 | A | 3/2003 |
| JP | 2004505660 | A | 2/2004 |
| JP | 2004249106 | A | 9/2004 |
| JP | 2005167058 | A | 6/2005 |
| JP | 2006511265 | A | 4/2006 |
| JP | 2007144225 | A | 6/2007 |
| JP | 2007520307 | A | 7/2007 |
| JP | 2008049199 | A | 3/2008 |
| JP | 2010019554 | A | 1/2010 |
| JP | 2010029650 | A | 2/2010 |
| JP | 2010204068 | A | 9/2010 |
| JP | 2013538097 | A | 10/2013 |
| JP | 2004512502 | A | 4/2014 |
| JP | 2014204876 | A | 10/2014 |
| JP | 2015002983 | A | 1/2015 |
| JP | 2015519970 | A | 7/2015 |
| JP | 2016508808 | A | 3/2016 |
| JP | 2017/506542 | A | 3/2017 |
| JP | 2017506538 | A | 3/2017 |
| JP | 2019051295 | A | 4/2019 |
| JP | 2020525167 | A | 8/2020 |
| JP | 2020525168 | A | 8/2020 |
| JP | 2020525169 | A | 8/2020 |
| JP | 6785554 | B2 | 10/2020 |
| JP | 6789944 | B2 | 11/2020 |
| JP | 2020534077 | A | 11/2020 |
| JP | 2020195788 | A | 12/2020 |
| JP | 2020535895 | A | 12/2020 |
| JP | 6832958 | B2 | 2/2021 |
| JP | 6835719 | B2 | 2/2021 |
| JP | 6838057 | B2 | 3/2021 |
| JP | 6849592 | B2 | 3/2021 |
| JP | 2021510104 | A | 4/2021 |
| JP | 6896719 | B2 | 6/2021 |
| JP | 6934933 | B2 | 9/2021 |
| JP | 6951560 | B2 | 10/2021 |
| JP | 6979633 | B2 | 12/2021 |
| JP | 6980696 | B2 | 12/2021 |
| JP | 7012726 | B2 | 1/2022 |
| JP | 2022500092 | A | 1/2022 |
| JP | 2022500093 | A | 1/2022 |
| JP | 2022501080 | A | 1/2022 |
| JP | 2022504159 | A | 1/2022 |
| JP | 2022509389 | A | 1/2022 |
| JP | 2022509391 | A | 1/2022 |
| JP | 2022509392 | A | 1/2022 |
| JP | 2022509393 | A | 1/2022 |
| JP | 2022509395 | A | 1/2022 |
| JP | 2022509401 | A | 1/2022 |
| JP | 2022509453 | A | 1/2022 |
| JP | 2022510217 | A | 1/2022 |
| JP | 7019679 | B2 | 2/2022 |
| JP | 7026118 | B2 | 2/2022 |
| JP | 2022514272 | A | 2/2022 |
| JP | 2022515488 | A | 2/2022 |
| JP | 2022516078 | A | 2/2022 |
| JP | 7053500 | B2 | 4/2022 |
| JP | 2022526104 | A | 5/2022 |
| JP | 2022527043 | A | 5/2022 |
| JP | 2022095785 | A | 6/2022 |
| JP | 7171645 | B2 | 11/2022 |
| JP | 7171663 | B2 | 11/2022 |
| JP | 7175640 | B2 | 11/2022 |
| JP | 2022546288 | A | 11/2022 |
| JP | 7187715 | B2 | 12/2022 |
| JP | 2022551875 | A | 12/2022 |
| JP | 2022552229 | A | 12/2022 |
| JP | 7201819 | B2 | 1/2023 |
| JP | 7232204 | B2 | 3/2023 |
| JP | 7239466 | B2 | 3/2023 |
| JP | 7265525 | B2 | 4/2023 |
| JP | 2023071859 | A | 5/2023 |
| JP | 7292448 | B2 | 6/2023 |
| JP | 7299992 | B2 | 6/2023 |
| JP | 7302936 | B2 | 7/2023 |
| JP | 7304344 | B2 | 7/2023 |
| JP | 7321162 | B2 | 8/2023 |
| JP | 7325430 | B2 | 8/2023 |
| JP | 7335367 | B2 | 8/2023 |
| JP | 7340594 | B2 | 9/2023 |
| JP | 7346293 | B2 | 9/2023 |
| JP | 7351972 | B2 | 9/2023 |
| JP | 7352561 | B2 | 9/2023 |
| JP | 7358391 | B2 | 10/2023 |
| JP | 7359765 | B2 | 10/2023 |
| JP | 7370386 | B2 | 10/2023 |
| JP | 2023162327 | A | 11/2023 |
| JP | 2024010135 | A | 1/2024 |
| JP | 2024020483 | A | 2/2024 |
| JP | 7479288 | B2 | 5/2024 |
| JP | 7479351 | B2 | 5/2024 |
| JP | 7485383 | B2 | 5/2024 |
| JP | 7530561 | B2 | 8/2024 |
| JP | 7542708 | B2 | 8/2024 |
| JP | 2024161427 | A | 11/2024 |
| JP | 7612816 | B2 | 1/2025 |
| JP | 7641600 | B2 | 3/2025 |
| KR | 102574559 | B1 | 9/2023 |
| KR | 102764982 | B1 | 2/2025 |
| KR | DM226835001 | S1 | 4/2025 |
| KR | 102854907 | B1 | 9/2025 |
| RU | 2589649 | C1 | 7/2016 |
| RU | 2839094 | C2 | 4/2025 |
| TW | 201729929 | A | 9/2017 |
| WO | WO94/06355 | A1 | 3/1994 |
| WO | WO98/07373 | A1 | 2/1998 |
| WO | WO02/32506 | A1 | 4/2002 |
| WO | WO2005/018469 | A1 | 3/2005 |
| WO | WO2008/051484 | A2 | 5/2008 |
| WO | WO2011/040054 | A1 | 7/2011 |
| WO | WO2011/092683 | A1 | 8/2011 |
| WO | WO2011/154654 | A2 | 12/2011 |
| WO | WO2014/008594 | A1 | 1/2014 |
| WO | WO2014/071386 | A1 | 5/2014 |
| WO | WO2015/000953 | A1 | 1/2015 |
| WO | WO2015/031532 | A1 | 3/2015 |
| WO | WO2015/153909 | A2 | 10/2015 |
| WO | WO2016/099279 | A1 | 6/2016 |
| WO | WO-2017027577 | A1 * | 2/2017 ............... A61N 7/02 |
| WO | WO2018/149671 | A1 | 8/2018 |
| WO | WO2018/208189 | A1 | 11/2018 |
| WO | WO2019/081329 | A1 | 5/2019 |
| WO | WO2019/117926 | A1 | 6/2019 |
| WO | WO2019/122941 | A1 | 6/2019 |
| WO | WO2019/148154 | A1 | 8/2019 |
| WO | WO2020/074615 | A1 | 4/2020 |
| WO | WO2020/087049 | A1 | 4/2020 |
| WO | WO2020/112688 | A1 | 6/2020 |
| WO | WO2020/217098 | A2 | 10/2020 |
| WO | WO2020/237382 | A1 | 12/2020 |
| WO | WO2020/245660 | A1 | 12/2020 |
| WO | WO2021/014221 | A1 | 1/2021 |
| WO | WO2021/032887 | A1 | 2/2021 |
| WO | WO2021/069216 | A1 | 4/2021 |
| WO | WO2021/069971 | A1 | 4/2021 |
| WO | WO2021/089810 | A1 | 5/2021 |
| WO | WO2021/105358 | A1 | 6/2021 |
| WO | WO2021/115958 | A1 | 6/2021 |
| WO | WO2021/116763 | A1 | 6/2021 |
| WO | WO2021/122253 | A1 | 6/2021 |
| WO | WO2021/123905 | A2 | 6/2021 |
| WO | WO2021/123906 | A1 | 6/2021 |
| WO | WO2021/140042 | A1 | 7/2021 |
| WO | WO2021/142090 | A1 | 7/2021 |
| WO | WO2021/170510 | A1 | 9/2021 |
| WO | WO2021/175626 | A1 | 9/2021 |
| WO | WO2021/176275 | A1 | 9/2021 |
| WO | WO2021/178961 | A1 | 9/2021 |
| WO | WO2021/180501 | A1 | 9/2021 |
| WO | WO2021/180550 | A1 | 9/2021 |
| WO | WO2021/213927 | A1 | 10/2021 |
| WO | WO2021/249936 | A1 | 12/2021 |
| WO | WO2021/258007 | A1 | 12/2021 |

(56) References Cited

FOREIGN PATENT DOCUMENTS

| | | |
|---|---|---|
| WO | WO2022/013266 A1 | 1/2022 |
| WO | WO2022/040493 A1 | 2/2022 |
| WO | WO2022/047193 A8 | 3/2022 |
| WO | WO2022/056394 A1 | 3/2022 |
| WO | WO2022/069254 A1 | 4/2022 |
| WO | WO2022/069303 A2 | 4/2022 |
| WO | WO2022/069327 A2 | 4/2022 |
| WO | WO2022/078744 A1 | 4/2022 |
| WO | WO2022/097138 A1 | 5/2022 |
| WO | WO2022/104683 A1 | 5/2022 |
| WO | WO2022/106891 A1 | 5/2022 |
| WO | WO2022/152724 A1 | 7/2022 |
| WO | WO2022/152827 A1 | 7/2022 |
| WO | WO2022/152828 A1 | 7/2022 |
| WO | WO2022/228922 A1 | 11/2022 |
| WO | WO2022/238058 A1 | 11/2022 |
| WO | WO2022/238092 A1 | 11/2022 |
| WO | WO2022/238229 A1 | 11/2022 |
| WO | WO2022/238274 A1 | 11/2022 |
| WO | WO2022/238276 A1 | 11/2022 |
| WO | WO2022/238392 A1 | 11/2022 |
| WO | WO2022/247242 A1 | 12/2022 |
| WO | WO2022/258561 A1 | 12/2022 |
| WO | WO2023/274899 A1 | 1/2023 |
| WO | WO2023/275617 A2 | 1/2023 |
| WO | WO2023/275771 A1 | 1/2023 |
| WO | WO2023/012516 A2 | 2/2023 |
| WO | WO2023/036742 A1 | 3/2023 |
| WO | WO2023/052278 A1 | 4/2023 |
| WO | WO2023/084307 A1 | 5/2023 |
| WO | WO2023/104599 A1 | 6/2023 |
| WO | WO2023/104841 A1 | 6/2023 |
| WO | WO2023/110555 A1 | 6/2023 |
| WO | WO2023/110556 A1 | 6/2023 |
| WO | WO2023/110594 A1 | 6/2023 |
| WO | WO2023/110607 A1 | 6/2023 |
| WO | WO2023/117721 A1 | 6/2023 |
| WO | WO2023/117821 A1 | 6/2023 |
| WO | WO2023/117822 A1 | 6/2023 |
| WO | WO2023/118080 A1 | 6/2023 |
| WO | WO2023105288 A1 | 6/2023 |
| WO | WO2023105290 A1 | 6/2023 |
| WO | WO2023/131566 A1 | 7/2023 |
| WO | WO2023/131574 A1 | 7/2023 |
| WO | WO2023/135024 A1 | 7/2023 |
| WO | WO2023/141653 A2 | 7/2023 |
| WO | WO2023/152639 A1 | 8/2023 |
| WO | WO2023/169967 A1 | 9/2023 |
| WO | WO2023/180811 A2 | 9/2023 |
| WO | WO2023/218428 A1 | 11/2023 |
| WO | WO2023/230053 A1 | 11/2023 |
| WO | WO2023/230054 A1 | 11/2023 |
| WO | WO2024/009143 A1 | 1/2024 |
| WO | WO2024/016088 A1 | 1/2024 |
| WO | WO2024/040185 A2 | 2/2024 |
| WO | WO2024/047580 A1 | 3/2024 |
| WO | WO2024/092272 A1 | 5/2024 |
| WO | WO2024/120659 A1 | 6/2024 |
| WO | WO2024/125872 A1 | 6/2024 |
| WO | WO2024/130252 A1 | 6/2024 |
| WO | WO2024/144897 A1 | 7/2024 |
| WO | WO2024/148416 A1 | 7/2024 |
| WO | WO2024/163876 A1 | 8/2024 |

OTHER PUBLICATIONS

Lu et al.; Transcranial MR-guided histotripsy system; IEEE transactions on ultrasonics, ferroelectrics, and frequency control; 66(9); pp. 2917-2929; Mar. 23, 2021.

Rosnitskiy et al.; Method for designing multielement fully populated random phased arrays for ultrasound surgery applications. IEEE transactions on ultrasonics, ferroelectrics, and frequency control; 65(4); pp. 630-637; Jan. 31, 2018.

Stocker et al.; Endocavity histotripsy for efficient tissue ablationRtransducer design and characterization. IEEE transactions on ultrasonics, ferroelectrics, and frequency control; 68(9); pp. 2896-2905; Jan. 28, 2021.

Wagner et al.; An X-ray C-arm guided automatic targeting system for histotripsy; IEEE Transactions on Biomedical Engineering; 70(2); pp. 592-602; Aug. 15, 2022.

Wijlemans et al.; Magnetic resonance-guided high-intensity focused ultrasound (MR-HIFU) ablation of liver tumours; Cancer Imaging; 12(2); pp. 387-394; Sep. 28, 2012.

Woodacre et al.; A low-cost miniature histotripsy transducer for precision tissue ablation. IEEE transactions on ultrasonics, ferroelectrics, and frequency control; 65(11); pp. 2131-2140; Nov. 1, 2018.

Miller et al.; U.S. Appl. No. 18/924,812 entitled "Histotripsy systems and methods," filed Oct. 23, 2024.

Ma et al.; Acoustic focusing and imaging via phononic crystal and acoustic metamaterials; Journal of Applied Physics; 131(1); doi:10.10653/5.0074503; 29 pages; Jan. 5, 2022.

Snell et al.; U.S. Appl. No. 18/886,807 entitled "Simulation software and tools for evaluating histotripsu therapy for a given pose and position of a therapy array," filed Sep. 16, 2024.

Schell et al.; U.S. Appl. No. 18/890,580 entitled "Co-registration techniques between computed tomography imaging systems and histrotripsy robotic systems," filed Nov. 14, 2024.

Hall et al. U.S. Appl. No. 19/229,825 entitled "Ultrasound transducer with transmit-receive capability for histotripsy," filed Jun. 5, 2025.

Xu et al.; U.S. Appl. No. 19/006,948 entitled "Histotripsy therapy systems and methods for the treatment of brain tissue," filed Dec. 31, 2024.

Maxwell et al.; U.S. Appl. No. 19/187,641 entitled "Histotripsy for thrombolysis," filed Apr. 23, 2025.

Cannata et al.;U.S. Appl. No. 19/210,971 entitled "Ultrasound therapy transducer for histotripsy system and methods," filed May 16, 2025.

Miller et al.; U.S. Appl. No. 19/046,322 entitled "Histotripsy systems and methods for managing thermal dose delivered to a subject," filed Feb. 5, 2025.

Miller; U.S. Appl. No. 19/103,752 entitled "Histotripsy systems and methods," filed Feb. 13, 2025.

Akiyama et al.; Elliptically curved acoustic lens for emitting strongly focused finite-amplitude beams: Application of the spheroidal beam equation model to the theoretical prediction; Acoustical Science and Technology, vol. 26, pp. 279-284, May 2005.

Appel et al.; Stereoscopic highspeed recording of bubble filaments; Ultrasonics Sonochemistry; vol. 11(1); pp. 39-42; Jan. 2004.

Arani et al.; Transurethral prostate magnetic resonance elestography; prospective imaging requirements; Magn. Reson. Med.; 65(2); pp. 340-349; Feb. 2011.

Aschoff et al.; How does alteration of hepatic blood flow affect liver perfusion and radiofrequency-induced thermal lesion size in rabbit liver?; J Magn Reson Imaging; 13(1); pp. 57-63; Jan. 2001.

Atchley et al.; Thresholds for cavitation produced in water by pulsed ultrasound; Ultrasonics .; vol. 26(5); pp. 280-285; Sep. 1988.

Avago Technologies; ACNV2601 High Insulation Voltage 10 MBd Digital Opotcoupler. Avago Technologies Data Sheet; pp. 1-11; Jul. 29, 2010.

Avago Technologies; Avago's ACNV2601 optocoupler is an optically coupled logic gate; Data Sheet; 2 pages; Jul. 29, 2010.

Avtech; AVR-8 Data sheet; May 23, 2004; 3 pages; retrieved from the internet (http//www.avtechpulse.com).

Bader et al.; For whom the bubble grows: physical principles of bubble nucleation and dynamics in histotripsy ultrasound therapy; Ultrasound in medicine & biology; 45(5); pp. 1056-1080; May 1, 2019.

Bak; Rapid protytyping or rapid production? 3D printing processes move industry towards the latter; Assembly Automation; 23(4); pp. 340-345; Dec. 1, 2003.

Billson et al.; Rapid prototyping technologies for ultrasonic beam focussing in NDE; IEEE International Ultrasonic Symposium Proceedings; pp. 2472-2474; Oct. 2011.

(56) References Cited

OTHER PUBLICATIONS

Bjoerk et al.; Cool/MOS CP—How to make most beneficial use of the generation of super junction technology devices. Infineon Technologies AG. [retrieved Feb. 4, 2014] from the internet (http://www.infineon.com/dgdl/Infineon+-+Application+Note+-+PowerMOSFETs+-+600V+CoolMOS%E284%A2+-+CP+Most+beneficial+use+of+superjunction+technologie+devices.pdf?folderid=db3a304412b407950112b408e8c90004&fileid=db3a304412b407950112b40ac9a40688> pp. 1, 4, 14; Feb. 2007.
Bland et al.; Surgical Oncology; McGraw Hill; Chap. 5 (Cavitron Ultrasonic Aspirator); pp. 461-462; Jan. 29, 2001.
Burdin et al.; Implementation of the laser diffraction technique for cavitation bubble investigations; Particle & Particle Systems Characterization; vol. 19; pp. 73-83; May 2002.
Cain et al.; Concentric-ring and sector-vortex phased-array applicators for ultrasound hyperthermia, IEEE Transactions on Microwave Theory and Techniques; 34(5); pp. 542-551; May 1986.
Cain, Charles A.; Histotripsy: controlled mechanical sub-division of soft tissues by high intensity pulsed ultrasound (conference presentation); American Institute of Physics (AIP) Therapeutic Ultrasound: 5th International Symposium on Therapeutic Ultrasound; 44 pgs.; Oct. 27-29, 2005.
Canney et al.; Shock-Induced Heating and Millisecond Boiling in Gels and Tissue Due to High Intensity Focused Ultrasound; Ultrasound in Medicine & Biology, vol. 36, pp. 250-267; Feb. 2010 (author manuscript).
Chan et al.; An image-guided high intensity focused ultrasound device for uterine fibroids treatment; Medical Physics, vol. 29, pp. 2611-2620, Nov. 2002.
Clasen et al.; MR-guided radiofrequency ablation of hepatocellular carcinoma: Long-term effectiveness; J Vase Interv Radiol; 22(6); pp. 762-770; Jun. 2011.
Clement et al.; A hemisphere array for non-invasive ultrasound brain therapy and surgery; Physics in Medicine and Biology, vol. 45, p. 3707-3719, Dec. 2000.
Cline et al.; Magnetic resonance-guided thermal surgery; Magnetic Resonance in Medicine; 30(1); pp. 98-106; Jul. 1993.
Curiel et al.; Elastography for the follow-up of high-intensity focused ultrasound prostate cancer treatment: Initial comparison with MRI; Ultrasound Med. Biol; 31(11); pp. 1461-1468; Nov. 2005.
Desilets et al.; The Design of Efficient Broad-Band Piezoelectric Transducers; Sonics and Ultrasonics, IEEE Transactions on, vol. 25, pp. 115-125, May 1978.
Dovedi et al.; Acquired Resistance to Fractionated Radiotherapy Can Be Overcome by Concurrent PD-LI Blockade; Cancer Research; 74(19); pp. 5458-5468; Oct. 1, 2014.
Emelianov et al.; Triplex ultrasound: Elasticity imaging to age deep venous thrombosis; Ultrasound Med Biol; 28(6); pp. 757-767; Jun. 2002.
Gateau et al.; Transcranial ultrasonic therapy based on time reversal of acoustically induced cavitation bubble signature. IEEE Transactions on Biomedical Engineering; 57(1); pp. 134-144; Sep. 18, 2009.
Giannatsis et al.; Additive fabrication technologies applied to medicine and health care: a review; The International Journal of Advanced Manufacturing Technology; 40(1-2); pp. 116-127; Jan. 2009.
Gudra et al.; Influence of acoustic impedance of multilayer acoustic systems on the transfer function of ultrasonic airborne transducers; Ultrasonics, vol. 40, pp. 457-463, May 2002.
Hall et al.; A Low Cost Compact 512 Channel Therapeutic Ultrasound System For Transcutaneous Ultrasound Surgery; AIP Conference Proceedings, Boston, MA; vol. 829, pp. 445-449, Oct. 27-29, 2005.
Hall et al.; Acoustic Access to the Prostate for Extracorporeal Ultrasound Ablation; Journal of Endourology, vol. 24, pp. 1875-1881, Nov. 2010.
Hall et al.; Histotripsy of the prostate: dose effects in a chronic canine model; Urology; 74(4); pp. 932-937; Oct. 2009 (author manuscript).
Hall et al.; Imaging feedback of tissue liquefaction (histotripsy) in ultrasound surgery; IEEE Ultrasonic Symposium, Sep. 18-21, 2005, pp. 1732-1734.
Haller et al.; Determination of acoustic cavitation probabilities and thresholds using a single focusing transducer to induce and detect acoustic cavitation events: I. Method and terminology; Ultrasound in Medicine & Biology; 44(2); pp. 377-396; Feb. 1, 2018.
Hartmann; Ultrasonic properties of poly(4-methyl pentene-1), Journal of Applied Physics, vol. 51, pp. 310-314, Jan. 1980.
Hobarth et al.; Color flow doppler sonography for extracorporal shock wave lithotripsy; Journal of Urology; 150(6); pp. 1768-1770; Dec. 1, 1993.
Holland et al.; Thresholds for transient cavitation produced by pulsed ultrasound in a controlled nuclei environment; J. Acoust. Soc. Am.; vol. 88(5); pp. 2059-2069; Nov. 1990.
Huber et al.; Influence of shock wave pressure amplitude and pulse repetition frequency on the lifespan, size and number of transient cavities in the field of an electromagnetic lithotripter; Physics in Medicine and Biology; vol. 43(10); pp. 3113-3128; Oct. 1998.
Hynynen et al.; Feasibility of using ultrasound phased arrays for MRI monitored noninvasive surgery; IEEE transactions on ultrasonics, ferroelectrics, and frequency control; 43(6); pp. 1043-1053; Nov. 1996.
Hynynen et al.; Tissue thermometry during ultrasound exposure; European Urology; 23(Suppl 1); pp. 12-16; (the year of publication is sufficiently earlier than the effective U.S. filing date and any foreign priority date so that the particular month of publication is not in issue) 1993.
International Society for Magnetic Resonance in Medicine (ISMRM); No. 105; XP040714022;I Jul. 24, 2020.
Hoogenboom et al.; Mechanical high-intensity focused ultrasound destruction of soft tissue: working mechanisms and physiologic effects; Ultrasound in medicine & biology; 41(6); pp. 1500-1517; Jun. 1, 2015.
Kallel et al.; The feasibility of elastographic visualization of HIFU-induced thermal lesions in soft tissues: Image-guided high-intensity focused ultrasound; Ultrasound Med. Biol; 25(4); pp. 641-647; May 1999.
Khokhlova et al.; Controlled tissue emulsification produced by high intensity focused ultrasound shock waves and millisecond boiling; J. Acoust. Soc. Am.; 130(5), pt. 2; pp. 3498-3510; Nov. 2011.
Kim et al.; Dependence of particle vol. fraction on sound velocity and attenuation of EPDM composites; Ultrasonics, vol. 46, pp. 177-183, Feb. 2007.
Kim et al.; Development of a wearable robotic positioning system for noninvasive transcranial focused ultrasound stimulation. IEEE/ASME Transactions on Mechatronics; 21(5); pp. 2284-2293; Jun. 13, 2016.
Konofagou; Quo vadis elasticity imaging?; Ultrasonics; 42(1-9); pp. 331-336; Apr. 2004.
Krimholtz et al.; New equivalent circuits for elementary piezoelectric transducers; Electronics Letters, vol. 6, pp. 398-399, Jun. 1970.
Kruse et al.; Tissue characterization using magnetic resonance elastography: Preliminary results; Phys. Med. Biol; 45(6); pp. 1579-1590; Jun. 2000.
Lake et al.; Histotripsy: minimally invasive technology for prostatic tissue ablation in an in vivo canine model; Urology; 72(3); pp. 682-686; Sep. 2008.
Lauterborn et al.; Cavitation bubble dynamics studied by high speed photography and holography: part one; Ultrasonics; vol. 23; pp. 260-268; Nov. 1985.
Lensing et al.; Deep-vein thrombosis; The Lancet, vol. 353, pp. 479-485, Feb. 6, 1999.
Lin et al.; Dual-beam histotripsy: a low-frequency pump enabling a high-frequency probe for precise lesion formation; IEEE Trans. Ultrason. Ferroelectr. Control; 61(2); pp. 325-340; Feb. 2014; (Author Manuscript; 29 pages).
Liu et al.; Real-time 2-D temperature imaging using ultrasound; IEEE Trans Biomed Eng; 57(1); pp. 12-16; Jan. 2010 (author manuscript, 16 pgs.).
Lu et al.; Viscoelastic property measurement in thin tissue constructs using ultrasound; IEEE Trans Ultrason Ferroelectr Freq Control; 55(2); pp. 368-383; Feb. 2008 (author manuscript, 37 pgs.).

(56) References Cited

OTHER PUBLICATIONS

Macoskey; Acoustic methods for histotripsy feedback; (Dissertation); Biomedical Engineering and Science Computing; University of Michigan 2019; 207 pages; retrived from the internet (https://deepblue.lib.umich.edu/handle/2027.42/149988) on Feb. 2022.
Manes et al.; Design of a Simplified Delay System for Ultrasound Phased Array Imaging; Sonics and Ultrasonics, IEEE Transactions on, vol. 30, pp. 350-354, Nov. 1983.
Maréchal et al.; Effect of Radial Displacement of Lens on Response of Focused Ultrasonic Transducer; Japanese Journal of Applied Physics, vol. 46, p. 3077-3085; May 15, 2007.
Maréchal et al.; Lens-focused transducer modeling using an extended KLM model; Ultrasonics, vol. 46, pp. 155-167, May 2007.
Martin et al.; Water-cooled, high-intensity ultrasound surgical applicators with frequency tracking; Ultrasonics, Ferroelectrics and Frequency Control, IEEE Transactions on, vol. 50, pp. 1305-1317, Oct. 2003.
Maxwell et al.; Cavitation clouds created by shock scattering from bubbles during histotripsy; J. Acoust. Soc. Am.; 130(4); pp. 1888-1898; Oct. 2011.
Maxwell et al.; Noninvasive Thrombolysis Using Pulsed Ultrasound Cavitation Therapy—Histotripsy; Ultrasound in Medicine & Biology, vol. 35, pp. 1982-1994, Dec. 2009 (author manuscript).
Maxwell; Noninvasive thrombolysis using histotripsy pulsed ultrasound cavitation therapy; PhD Dissertation. University of Michigan, Ann Arbor, Michigan. Jun. 2012.
Maxwell et al.; In-vivo study of non-invasive thrombolysis by histotripsy in a porcine model; IEEE international Ultrasonics Symposium; IEEE; p. 220-223; Sep. 20, 2009.
Maxwell et al.; The role of compressional pressure in the formation of dense bubble clouds in histotripsy; 2009 IEEE International Ultrasonics Symposium; pp. 81-84; Sep. 20, 2009.
Miller et al.; A review of in vitro bioeffects of inertial ultrasonic cavitation from a mechanistic perspective; Ultrasound in Medicine and Biology; vol. 22; pp. 1131-1154; (the year of publication is sufficiently earlier than the effective U.S. filing date and any foreign priority date so that the particular month of publication is not in issue) 1996.
Miller et al.; Investigation of the mechanism of ARFI-based color doppler feedback of histotripsy tissue fractionation; Ultrasonic Symposium (IUS); 2013 IEEE International; 4 pages; Jul. 21-25, 2013.
Miller et al.; Real-time elastography-based monitoring of histotripsy tissue fractionation using color doppler; Ultrasonics Symposium (IUS); 2012 IEEE International; 8 pages; Oct. 7-10, 2012.
Nightingale et al.; Analysis of contrast in images generated with transient acoustic radiation force; Ultrasound Med Biol; 32(1); pp. 61-72; Jan. 2006.
Ohl et al.; Bubble dynamics, shock waves and sonoluminescence; Phil. Trans. R. Soc. Lond. A; vol. 357; pp. 269-294; (the year of publication is sufficiently earlier than the effective U.S. filing date and any foreign priority date so that the particular month of publication is not in issue) 1999.
Okada et al.; A case of hepatocellular carcinoma treated by MR-guided focused ultrasound ablation with respiratory gating; Magn Reson Med Sci; 5(3); pp. 167-171; Oct. 2006.
Palmeri et al.; Acoustic radiation force-based elasticity imaging methods; Interface Focus; 1; pp. 553-564; Aug. 2011.
Parsons et al.; Cost-effective assembly of a basic fiber-optic hydrophone for measurement of high-amplitude therapeutic ultrasound fields; The Journal of the Acoustical Society of America, vol. 119, pp. 1432-1440, Mar. 2006.
Parsons et al.; Pulsed cavitational ultrasound therapy for controlled tissue homogenization; Ultrasound in Med. & Biol.; vol. 32(1); pp. 115-129; Jan. 2006.
Pishchalnikov et al.; Cavitation Bubble Cluster Activity in the Breakage of Kidney Stones by Lithotripter Shock Waves; J Endourol .; 17(7): 435-446; Sep. 2003.
Porter et al.; Reduction in left ventricular cavitary attenuation and improvement in posterior myocardial contrast . . .; J Am Soc Echocardiography; pp. 437-441; Jul.-Aug. 1996.
Qu et al.; Non-thermal histotripsy tumor ablation promotes abscopal immune responses that enhance cancer immunotherapy; Journal for immunotherapy of cancer, 8(1); Jan. 15, 2020.
Roberts et al.; Pulsed cavitational ultrasound: a noninvasive technology for controlled tissue ablation (histotripsy) in the rabbit kidney; Journal of Urology; vol. 175(2); pp. 734-738; Feb. 2006.
Rosenschein et al.; Ultrasound Imaging-Guided Noninvasive Ultrasound Thrombolysis: Preclinical Results; Circulation; vol. 102; pp. 238-245, Jul. 11, 2000.
Rowland et al.; MRI study of hepatic tumours following high intensity focused ultrasound surgery; British Journal of Radiology; 70; pp. 144-153; Feb. 1997.
Roy et al.; A precise technique for the measurement of acoustic cavitation thresholds and some preliminary results; Journal of the Acoustical Society of America; vol. 78(5); pp. 1799-1805, Nov. 1985.
Sapareto et al.; Thermal dose determination in cancer therapy; Int J Radiat Oncol Biol Phys; 10(6); pp. 787-800; Apr. 1984.
Sapozhnikov et al.; Ultrasound-Guided Localized Detection of Cavitation During Lithotripsy in Pig Kidney in Vivo; IEEE Ultrasonics Symposium, vol. 2; pp. 1347-1350; Oct. 7-10, 2001.
Sato et al.; Experimental Investigation of Phased Array Using Tapered Matching Layers. 2002 IEEE Ultrasound Symposium. Vol. 2; pp. 1235-1238, Oct. 2002.
Sferruzza et al.; Generation of high power unipolar pulse with a piezocomposite transducer; In 1999 IEEE Ultrasonics Symposium Proceedings; International Symposium (Cat. No. 99CH37027); vol. 2; pp. 1125-1128; Oct. 17, 1999.
Shung; Diagnostic Ultrasound: Imaging and Blood Flow Measurements; Taylor and Francis Group, LLC; Boca Raton, FL; 207 pages; (the year of publication is sufficiently earlier than the effective U.S. filing date and any foreign priority date so that the particular month of publication is not in issue) 2006.
Simonin et al.; Characterization of heterogeneous structure in a polymer object manufactured by stereolithography with low-frequency microechography; Journal of Materials Chemistry; vol. 6, pp. 1595-1599, Sep. 1996.
Sokolov et al.; Use of a dual-pulse lithotripter to generate a localized and intensified cavitation field; Journal of the Acoustical Society of America; vol. 110(3); pp. 1685-1695; Sep. 2001.
Song et al.; Feasibility of Using Lateral Mode Coupling Method for a Large Scale Ultrasound Phased Array for Noninvasive Transcranial Therapy; Biomedical Engineering; IEEE Transactions on, vol. 57, pp. 124-133; Jan. 2010 (author manuscript).
Souchon et al.; Visualisation of HIFU lesions using elastography of the human prostate in vivo: Preliminary results; Ultrasound Med. Biol; 29(7); pp. 1007-1015; Jul. 2003.
Souquet et al.; Design of Low-Loss Wide-Band Ultrasonic Transducers for Noninvasive Medical Application; Sonics and Ultrasonics, IEEE Transactions on, vol. 26, pp. 75-80, Mar. 1979.
Sukovich et al.; Real-time transcranial histotripsy treatment localization and mapping using acoustic cavitation emission feedback; IEEE transactions on ultrasonics, ferroelectrics, and frequency control; 67(6); pp. 1178-1791; Jan. 17, 2020.
Therapeutic Ultrasound Group. Non-invasive Ultrasonic Tissue Fraction for Treatment of Benign Disease and Cancer—"Histotripsy". University research [online]. Biomedical Engineering Department, University of Michigan. Jul. 2011 [retrieved on Jan. 28, 2014] from: (http://web/archive.org/web/20110720091822/http://www.histotripsy.umich.edu/index.html> entiredocument) Jul. 2011.
Toda; Narrowband impedance matching layer for high efficiency thickness mode ultrasonic transducers; Ultrasonics, Ferroelectrics and Frequency Control, IEEE Transactions on, vol. 49, pp. 299-306, Mar. 2002.
Urban et al.; Measurement of prostate viscoelasticity using shearwave dispersion ultrasound vibrometry (SDUV): an in vitro study; IEEE International Ultrasonics Symposium Proceedings (IUS); pp. 1141-1144; Oct. 11, 2010.

(56) References Cited

OTHER PUBLICATIONS

Van Kervel et al.; A calculation scheme for the optimum design of ultrasonic transducers; Ultrasonics, vol. 21, pp. 134-140, May 1983.
Wang et al.; Quantitative ultrasound backscatter for pulsed cavitational ultrasound therapy-histotripsy; Ultrasonics, Ferroelectrics and Frequency Control, IEEE Transactions on, vol. 56, pp. 995-1005, May 2009.
Wikipedia; Medical ultrasound; 15 pages; retrieved from the internet (https://en.wikipedia.org/w/index.php?title=Medical_utrasound&oldid=515340960) on Jan. 12, 2018.
Wu et al.; Mechanism and dynamics of hydrodynamic-acoustic cavitation (HAC); Ultrasonics sonochemistry; vol. 49., pp. 89-96; Dec. 1, 2018.
Xie et al.; Correspondence of ultrasound elasticity imaging to direct mechanical measurement in aging DVT in rats; Ultrasound Med Biol; 31(10); pp. 1351-1359; Oct. 2005 (author manuscript, 20 pgs.).
Xu et al.; A new strategy to enhance cavitational tissue erosion by using a high intensity initiating sequence; IEEE Trans Ultrasonics Ferroelectrics and Freq Control; vol. 53(8); pp. 1412-1424; Aug. 2006.
Xu et al.; Controlled ultrasound tissue erosion: the role of dynamic interaction between insonation and microbubble activity; Journal of the Acoustical Society of America; vol. 117(1); pp. 424-435; Jan. 2005.
Xu et al.; Controlled ultrasound tissue erosion; IEEE Transaction on Ultrasonics, Ferroelectrics, and Frequency Control; vol. 51 (6); pp. 726-736; Jun. 2004.
Xu et al.; Effects of acoustic parameters on bubble cloud dynamics in ultrasound tissue erosion (histotripsy); Journal of the Acoustical Society of America; vol. 122(1); pp. 229-236; Jul. 2007.
Xu et al.; High Speed Imaging of Bubble Clouds Generated in Pulsed Ultrasound Cavitational Therapy Histotripsy; IEEE Trans Ultrason Ferroelectr Freq Control; ; vol. 54; No. 10; pp. 2091R2101; Oct. 2007.
Xu et al.; Investigation of intensity threshold for ultrasound tissue erosion; Ultrasound in Med. & Biol.; vol. 31(12); pp. 1673-1682; Dec. 2005.
Xu et al.; Optical and acoustic monitoring of bubble cloud dynamics at a tissue-fluid interface in ultrasound tissue erosion; Journal of the Acoustical Society of America; vol. 121(4); pp. 2421-2430; Apr. 2007.
Yan et al.; A review of rapid prototyping technologies and systems; Computer-Aided Design, vol. 28, pp. 307-318, Apr. 1996.
Zhang et al.; A fast tissue stiffness-dependent elastography for HIFU-induced lesions inspection; Ultrasonics; 51(8); pp. 857-869; Dec. 2011.
Zheng et al.; An acoustic backscatter-based method for localization of lesions induced by high-intensity focused ultrasound; Ultrasound Med Biol; 36(4); pp. 610-622; Apr. 2010.
Cannata et al.; U.S. Appl. No. 18/311,050 entitled "Histotripsy systems and methods," filed May 2, 2023.
Duryea et al.; U.S. Appl. No. 18/498,979 entitled "Histotripsy systems and methods," filed Oct. 31, 2023.
Cannata et al.; U.S. Appl. No. 18/630,758 entitled "Histotripsy systems and methods," filed Apr. 9, 2024.
Cannata et al.; U.S. Appl. No. 18/642,529 entitled "Histotripsy systems and associated methods including user interfaces and workflows for treatment planning and therapy," filed Apr. 22, 2024.
Stopek.; U.S. Appl. No. 18/761,937 entitled "Minimally invasive histotripsy systems and methods," filed Jul. 2, 2024.
Allen et al.; Controlling cavitation?based image contrast in focused ultrasound histotripsy surgery; Magnetic resonance in medicine; 73(1); pp. 204-213; Jan. 2015.
Bader et al.; Assessment of collaborative robot (cobot)-assisted histotripsy for venous clot ablation; IEEE Transactions on Biomedical Engineering; 68(4); pp. 1220-1228; Sep. 11, 2020.
Coon et al.; HIFU treatment time reduction in superficial tumours through focal zone path selection; International journal of hyperthermia; 27(5); pp. 465-481; Aug. 1, 2011.
Froghi et al.; Liver ultrasound histotripsy: novel analysis of the histotripsy site cell constituents with implications for histotripsy application in cell transplantation and cancer therapy; Bioengineering; 10(2); 276; 20 pages; Feb. 20, 2023.
Gobl; Acoustic window planning for ultrasound acquisition. International journal of computer assisted radiology and surgery; 12(6); pp. 993-1001; Jun. 2017.
Khokhlova et al.; Initial assessment of boiling histotripsy for mechanical ablation of ex vivo human prostate tissue; Ultrasound in Medicine & Biology; 49(1); pp. 62-71; 20 pages; (Author Manuscript); Jan. 2023.
Kumar et al.; A comparative study of histotripsy parameters for the treatment of fibrotic ex-vivo human benign prostatic hyperplasia tissue; Research Square rs.3.rs-4549536.2; doi: 10.21203/rs-4549536/v1; 24 pages; (Preprint); Jul. 2024.
Vlaisavljevich et al.; Histotripsy-induced caviation cloud initiation thresholds in tissues of different mechanical properties; IEEE Transactions on Ultrasonic, Ferroelectrics, and Frequency control; 61(2); pp. 341-352; 27 pages; (Author manuscript); Feb. 2014.
Vlaisaljevich et al.; Effects of tissue stiffness, ultrasound frequency, and pressure on histotripsy-induced cavitation bubble behavior; Physics in Medical and Biology; 60(6); pp. 2271-2292; 30 pages; (Author manuscript); Mar. 2015.
Vlaisavljevich et al.; Effects of thermal preconditioning on tissue susceptibility to histotripsy; Ultrasound in Medicine and Biology; 41(11); pp. 2938-2954; 27 pages; (Author manuscript); Nov. 2015.
Vlaisavljevich et al.; Effects of tissue mechanical properties on susceptibility to histotripsy-induced tissue damage; Physics in Medicine and Biology; 59(2); pp. 253-270; 26 pages; (Author Manuscript); Jan. 2014.
Duryea et al.; U.S. Appl. No. 19/139,227 entitled "Systems and methods for enhancing histotripsy bubble cloud size through pulse shape optimization," filed Jun. 13, 2025.
Stopek; U.S. Appl. No. 19/361,539 entitled "Histotripsy systems and methods for rejected organ recovery" filed Oct. 17, 2025.
Xu et al.; U.S. Appl. No. 19/471,955 entitled "Simultaneous MRI and ultrasound guidance for histotripsy systems and methods," filed Oct. 2, 2025.
Xu et al.; U.S. Appl. No. 19/471,961 entitled "Real-time monitoring of histrotripsy dose delivery damage spatially and temporally," filed Oct. 2, 2025.
Hall et al.; U.S. Appl. No. 19/475,240 entitled "Histotripsy systems and methods," filed Oct. 14, 2025.
Duryea et al.; U.S. Appl. No. 19/270,038, entitled "Histotripsy systems and methods," filed Jul. 15, 2025.
Grumbir et al.; U.S. Appl. No. 19/510,190 entitled "Ultrasound coupling systems for histotripsy and systems, methods, and devices therof," filed Feb. 10, 2026.

* cited by examiner

HISTOTRIPSY SYSTEMS AND METHODS

PRIORITY CLAIM

This patent application claims priority to U.S. provisional patent application No. 63/302,501, titled "HISTOTRIPSY SYSTEMS AND METHODS" and filed on Jan. 24, 2022, which is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD

The present disclosure details novel high intensity therapeutic ultrasound (HITU) systems configured to produce acoustic cavitation, methods, devices and procedures for the minimally and non-invasive treatment of healthy, diseased and/or injured tissue. The acoustic cavitation systems and methods described herein, also referred to Histotripsy, may include transducers, drive electronics, positioning robotics, imaging systems, and integrated treatment planning and control software to provide comprehensive treatment and therapy for soft tissues in a patient.

BACKGROUND

Histotripsy, or pulsed ultrasound cavitation therapy, is a technology where extremely short, intense bursts of acoustic energy induce controlled cavitation (microbubble formation) within the focal volume. The vigorous expansion and collapse of these microbubbles mechanically homogenizes cells and tissue structures within the focal volume. This is a very different end result than the coagulative necrosis characteristic of thermal ablation. To operate within a non-thermal, Histotripsy realm; it is necessary to deliver acoustic energy in the form of high amplitude acoustic pulses with low duty cycle.

Compared with conventional focused ultrasound technologies, Histotripsy has important advantages: 1) the destructive process at the focus is mechanical, not thermal; 2) cavitation appears bright on ultrasound imaging thereby confirming correct targeting and localization of treatment; 3) treated tissue generally, but not always, appears darker (more hypoechoic) on ultrasound imaging, so that the operator knows what has been treated; and 4) Histotripsy produces lesions in a controlled and precise manner. It is important to emphasize that unlike thermal ablative technologies such as microwave, radiofrequency, high-intensity focused ultrasound (HIFU) cryo or radiation, Histotripsy relies on the mechanical action of cavitation for tissue destruction and not on heat, cold or ionizing energy.

SUMMARY OF THE DISCLOSURE

An ultrasound treatment head is provided, comprising a therapy transducer array configured to deliver ultrasound pulses to a focal location, a bore located within the therapy transducer array, a coupling assembly sized and configured for axial and rotational movement within the bore of the therapy transducer array, an ultrasound imaging probe coupled to the coupling assembly, and at least one user input device configured to control axial movement and/or rotation of the ultrasound imaging probe relative to the therapy transducer array.

In some embodiments, the ultrasound treatment head further comprises at least one encoder configured to track an axial and/or rotational position of the ultrasound imaging probe.

In one embodiment, the ultrasound treatment head further comprises one or more processors configured to register the axial and/or rotational position of the ultrasound imaging probe with a digital treatment plan.

In another embodiment, the at least one encoder is in electrical communication with one or more remote processors configured to register the axial and/or rotational position of the ultrasound imaging probe with a digital treatment plan.

In some embodiments, the digital treatment plan further comprises at least one of a target contour and a margin contour.

In one embodiment, the at least one user input device further comprises an image probe control, a first shaft coupled to the image probe control, a first gear coupled to the first shaft, a second gear coupled to the first gear, a second shaft coupled to the second gear, a shuttle assembly coupled to the coupling assembly and configured to move axially along the second shaft when the second shaft is rotated, wherein manipulation of the image probe control results in a corresponding axial movement of the ultrasound imaging probe along a length of the second shaft.

In some embodiments, the at least on user input device further comprises a rotational sleeve disposed around the coupling assembly, the rotational sleeve being keyed to the coupling assembly, wherein rotation of the rotational sleeve results in a corresponding rotational movement of the ultrasound imaging probe.

In one example, the ultrasound treatment head further comprises one or more detents positioned at specified rotational angles against the rotational sleeve to provide tactile feedback to a user.

In some embodiments, the rotational sleeve further includes one or more tabs which align with an axial position of the ultrasound imaging probe.

In one example, the ultrasound treatment head further comprises one or more bushings configured to align an outer diameter of the coupling assembly with an inner diameter of the bore.

In some embodiments, the ultrasound treatment head further comprises a position sensor configured to determine when the ultrasound imaging probe is in a retracted position.

In one embodiment, the ultrasound treatment head further comprises one or more processors in electrical communication with the position sensor configured to prevent initiation of therapy with the therapy transducer array if the position sensor determines that the ultrasound imaging probe is not in a specified position with respect to the therapy transducer array.

In some examples, the specified position comprises fully retracted within the ultrasound treatment head.

In other embodiments, the specified position comprises positioned so as to not obstruct or substantially obstruct the therapy transducer array.

In one example, the ultrasound treatment head further comprises a keyed plate configured to rotate with rotation of the ultrasound imaging probe further comprises a rotational encoder coupled to the keyed plate, wherein a rotor of the rotational encoder rotates with rotation of the keyed plate and a stator of the rotational encoder remains static during rotation of the keyed plate.

In some examples, the ultrasound treatment head further comprises a grip base disposed over the keyed plate and configured to couple to the therapy transducer array.

In one embodiment, the ultrasound treatment head further comprises a quick-release connector configured to couple a robotic positioning arm to the ultrasound treatment head.

In some examples, the quick-release connector includes mating features configured to interface with corresponding mating features on the robotic positioning arm.

The ultrasound treatment head of claim 16, further comprising one or more handles, wherein at least one handle is hollow to allow for routing of a wire from the rotational encoder to a processor.

The ultrasound treatment head of claim 1, further comprising a pair of handles positioned on opposing sides of the ultrasound treatment head.

The ultrasound treatment head of claim 1, further comprising at least one handle, wherein the at least one handle includes a free-drive user input device configured to allow a user to move or manipulate a position and/or orientation of the ultrasound treatment head when the ultrasound treatment head is coupled to a robotic positioning arm.

An ultrasound therapy system, comprising a treatment head that includes an ultrasound therapy transducer and an ultrasound imaging probe, wherein the ultrasound imaging probe is configured to move axially and be rotated independently with respect to the ultrasound therapy transducer, a robotic positioning arm coupled to the treatment head, the robotic positioning arm being configured to move the treatment head according to a digital treatment plan.

In one embodiment, the ultrasound therapy system further comprises at least one encoder disposed in the treatment head and configured to track an axial and/or rotational position of the ultrasound imaging probe.

In some examples, the ultrasound therapy system comprises one or more processors configured to register a position of the ultrasound imaging probe with the digital treatment plan.

In one embodiment, the ultrasound therapy system further comprises an electrical connection between the therapy head and the robotic positioning arm to communicate the position of the ultrasound imaging probe to a controller of the robotic positioning arm.

In another embodiment, the ultrasound therapy system further comprises a quick-release connector configured to couple the robotic positioning arm to the treatment head.

In some embodiments, the ultrasound therapy system further comprises at least one encoder configured to track an axial and/or rotational position of the ultrasound imaging probe.

In other embodiments, the ultrasound therapy system further comprises one or more processors configured to register the axial and/or rotational position of the ultrasound imaging probe with a digital treatment plan.

In some embodiments, the at least one encoder is in electrical communication with one or more remote processors configured to register the axial and/or rotational position of the ultrasound imaging probe with a digital treatment plan.

In one example, the ultrasound therapy system further comprises at least one user input device configured to control axial and/or rotational movement of the ultrasound imaging probe.

In some embodiments, the at least one user input device further comprises an imaging probe control, a first shaft coupled to the imaging probe control, a first gear coupled to the first shaft, a second gear coupled to the first gear, a second shaft coupled to the second gear, a shuttle assembly coupled to the coupling assembly and configured to move axially along the second shaft when the second shaft is rotated, wherein manipulation of the imaging probe control results in a corresponding axial movement of the ultrasound imaging probe along a length of the second shaft.

In some examples, the at least on user input device further comprises a rotational sleeve disposed around the coupling assembly, the rotational sleeve being keyed to the coupling assembly, wherein rotation of the rotational sleeve results in a corresponding rotational movement of the ultrasound imaging probe.

In one embodiment, the ultrasound therapy system further comprises one or more detents positioned at specified rotational angles against the rotational sleeve to provide tactile feedback to a user.

In some embodiments, the rotational sleeve further includes one or more tabs which align with an axial position of the ultrasound imaging probe.

In one example, the ultrasound therapy system further comprises one or more bushings configured to align an outer diameter of the coupling assembly with an inner diameter of the bore.

In other embodiments, the ultrasound therapy system further comprises a position sensor configured to determine when the ultrasound imaging probe is in a retracted position.

In one implementation, the ultrasound therapy system further comprises one or more processors in electrical communication with the position sensor configured to prevent initiation of therapy with the therapy transducer array if the position sensor determines that the ultrasound imaging probe is not in a specified position with respect to the therapy transducer array.

In some examples, the specified position comprises fully retracted within the ultrasound treatment head.

In other embodiments, the specified position comprises positioned so as to not obstruct or substantially obstruct the therapy transducer array.

In another implementation, a keyed plate is configured to rotate with rotation of the ultrasound imaging probe.

In some embodiments, the ultrasound therapy system further comprises a rotational encoder coupled to the keyed plate, wherein a rotor of the rotational encoder rotates with rotation of the keyed plate and a stator of the rotational encoder remains static during rotation of the keyed plate.

In another embodiment, the ultrasound therapy system further comprises a grip base disposed over the keyed plate and configured to couple to the therapy transducer array.

A method is provided, comprising submerging an ultrasound treatment head into an acoustic coupling medium in acoustic communication with a patient, positioning the ultrasound treatment head with a robotic arm such that a focus of the ultrasound treatment head is located on a target tissue volume, axially advancing an ultrasound imaging probe of the ultrasound treatment head towards the target tissue volume while maintaining the focus of the ultrasound treatment head on the target tissue volume, obtaining ultrasound images of the target tissue volume with the ultrasound imaging probe for treatment planning, at least partially retracting the ultrasound imaging probe relative to the ultrasound treatment head, and transmitting histotripsy pulses from the ultrasound treatment head into the target tissue volume.

In some embodiments, the method further comprises rotating the ultrasound imagining probe while maintaining the focus of the ultrasound treatment head on the target tissue volume.

In some examples, axially advancing the ultrasound imaging probe further comprises axially advancing the ultrasound imaging probe to make contact with a membrane of a coupling container in acoustic communication with the patient.

In one embodiment, the membrane is in contact with skin of the patient.

In other embodiments, axially advancing the ultrasound imaging probe further comprises axially advancing the ultrasound imaging probe to make contact with skin of the patient.

In some embodiments, the method further comprises moving the ultrasound treatment head with the robotic arm while maintaining acoustic coupling between the ultrasound imaging probe and the skin or membrane.

In other embodiments, the method further comprises, prior to initiating ultrasound therapy determining if the ultrasound imaging probe is at least partially retracted to a specified position, and initiating ultrasound therapy only if the ultrasound imaging probe is in the specified position.

In some examples, the specified position comprises a fully retracted position.

In another embodiment, the specified position comprises a position that does not substantially obstruct transducer elements of the ultrasound treatment head.

In some embodiments, the specified position comprises a position that does not substantially obstruct histotripsy pulses from the ultrasound treatment head.

An ultrasound treatment system is provided, comprising a robotic positioning arm controlled by a robotic positioning system, a treatment head disposed on the robotic positioning arm, the treatment head comprising, a therapy transducer array configured to deliver ultrasound pulses to a focal location, an ultrasound imaging probe sized and configured for axial and rotational movement within a bore of the therapy transducer array, a linear encoder configured to determine an axial position of the ultrasound imaging probe, and, a rotational encoder configured to determine a rotational position of the ultrasound imaging probe, at least one processor configured to communicate the axial position and rotational position of the ultrasound imaging probe to the robotic positioning system, one or more processors in communication with the robotic positioning system configured to receive the axial position and rotational position of the ultrasound imaging probe from the linear encoder and rotational encoder, respectively, and to register the axial position and rotational position of the ultrasound imaging probe with a digital treatment plan.

In one embodiment, the ultrasound treatment system further comprises a position sensor configured to determine if the ultrasound imaging probe is at a specified axial position with respect to the therapy transducer array.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

The system, methods and devices of the disclosure may be used for open surgical, minimally invasive surgical (laparoscopic and percutaneous), robotic surgical (integrated into a robotically-enabled medical system), endoscopic or completely transdermal extracorporeal non-invasive acoustic cavitation for the treatment of healthy, diseased and/or injured tissue including but not limited to tissue destruction, cutting, skeletonizing and ablation. Furthermore, due to tissue selective properties, histotripsy may be used to create a cytoskeleton that allows for subsequent tissue regeneration either de novo or through the application of stem cells and other adjuvants. Finally, histotripsy can be used to cause the release of delivered agents such as chemotherapy and immunotherapy by locally causing the release of these agents by the application of acoustic energy to the targets. As will be described below, the acoustic cavitation system may include various sub-systems, including a Cart, Therapy, Integrated Imaging, Robotics, Coupling and Software. The system also may comprise various Other Components, Ancillaries and Accessories, including but not limited to computers, cables and connectors, networking devices, power supplies, displays, drawers/storage, doors, wheels, and various simulation and training tools, etc. All systems, methods and means creating/controlling/delivering histotripsy are considered to be a part of this disclosure, including new related inventions disclosed herein.

Figure 1A:
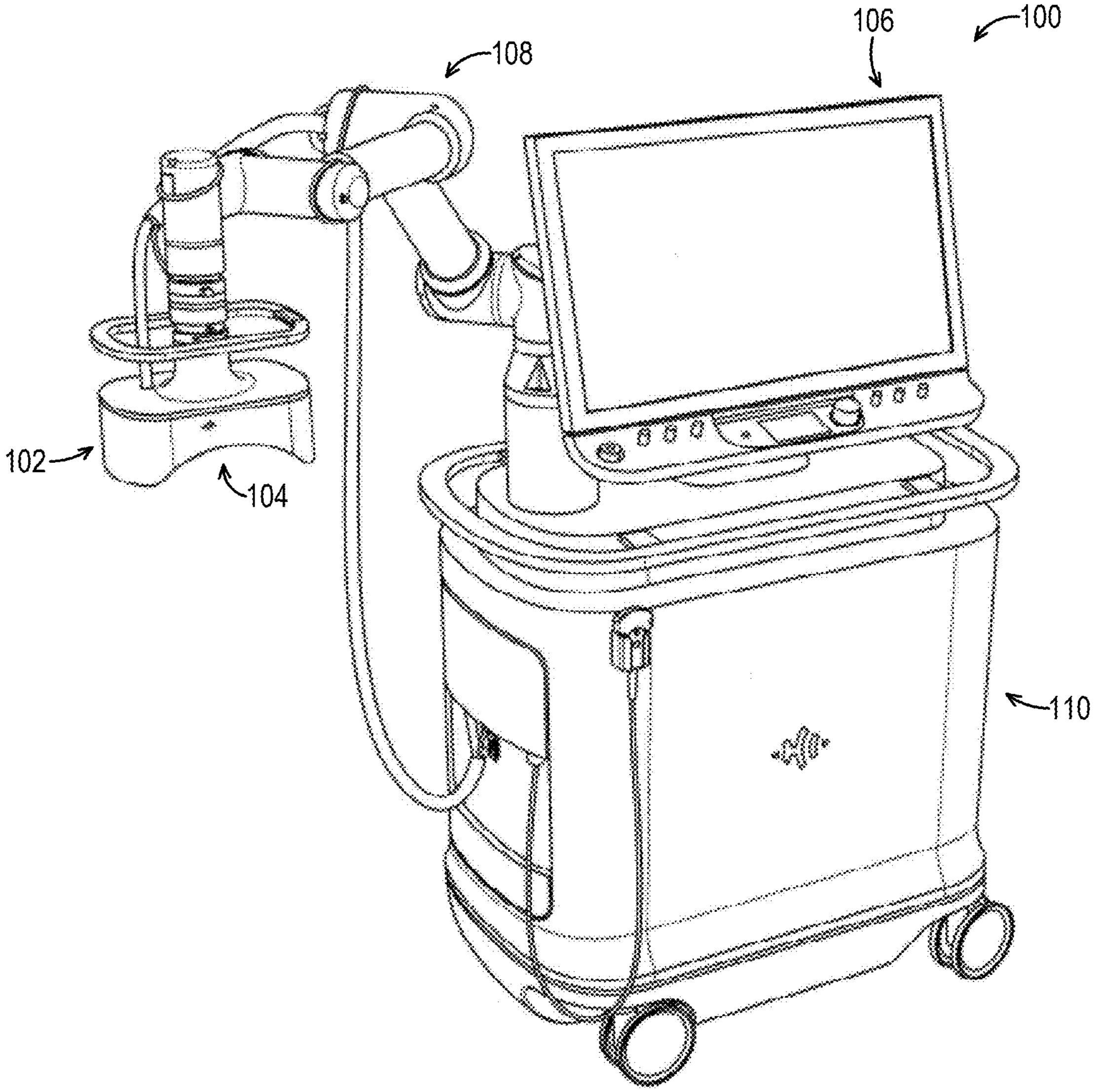
FIGS. 1A-1B illustrate an ultrasound imaging and therapy system.

FIG. 1A generally illustrates histotripsy system 100 according to the present disclosure, comprising a therapy transducer 102, an imaging system 104, a display and control panel 106, a robotic positioning arm 108, and a cart 110. The system can further include an ultrasound coupling interface and a source of coupling medium, not shown.

Figure 1B:
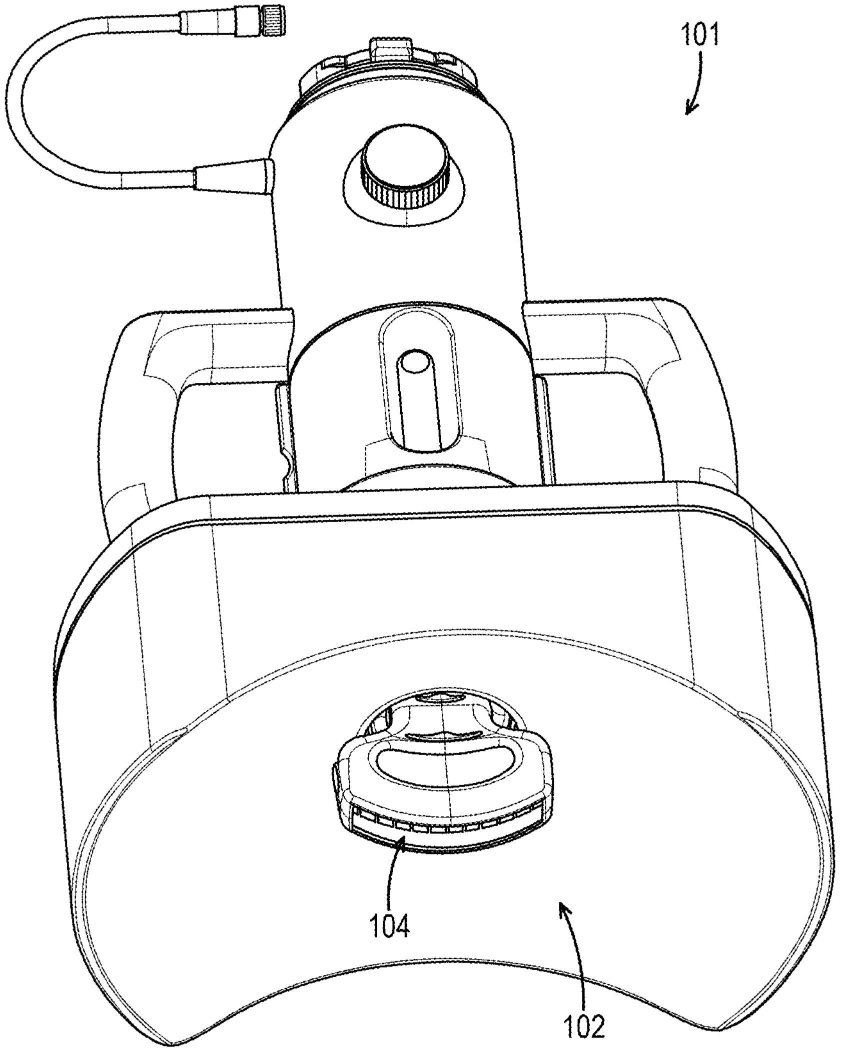

FIG. 1B is a bottom view of the therapy transducer 102 and the imaging system 104. In some embodiments, the imaging system may comprise an ultrasound imaging system. As shown, the imaging system can be positioned in the center of the therapy transducer. However, other embodiments can include the imaging system positioned in other locations within the therapy transducer, or even directly integrated into the therapy transducer. In some embodiments, the imaging system is configured to produce realtime imaging at a focal point of the therapy transducer. The system also allows for multiple imaging transducers to be located within the therapy transducer to provide multiple views of the target tissue simultaneously and to integrate these images into a single 3-D image. Additional details around the therapy transducer 102 and imaging system 104, collectively referred to herein as a "treatment head" 101, are provided below.

The histotripsy system may comprise one or more of various sub-systems, including a Therapy sub-system that can create, apply, focus and deliver acoustic cavitation/histotripsy through one or more therapy transducers, Integrated Imaging sub-system (or connectivity to) allowing real-time visualization of the treatment site and histotripsy effect through-out the procedure, a Robotics positioning sub-system to mechanically and/or electronically steer the therapy transducer, further enabled to connect/support or interact with a Coupling sub-system to allow acoustic coupling between the therapy transducer and the patient, and Software to communicate, control and interface with the system and computer-based control systems (and other external systems) and various Other Components, Ancillaries and Accessories, including one or more user interfaces and displays, and related guided work-flows, all working in part or together. The system may further comprise various fluidics and fluid management components, including but not limited to, pumps, valve and flow controls, temperature and degassing controls, and irrigation and aspiration capabilities, as well as providing and storing fluids. It may also contain various power supplies and protectors.

As described above, the histotripsy system may include integrated imaging. However, in other embodiments, the histotripsy system can be configured to interface with separate imaging systems, such as C-arm, fluoroscope, cone beam CT, MRI, etc., to provide real-time imaging during histotripsy therapy. In some embodiments, the histotripsy system can be sized and configured to fit within a C-arm, fluoroscope, cone beam CT, MRI, etc.

Cart

The Cart 110 may be generally configured in a variety of ways and form factors based on the specific uses and procedures. In some cases, systems may comprise multiple Carts, configured with similar or different arrangements. In some embodiments, the cart may be configured and arranged to be used in a radiology environment and in some cases in concert with imaging (e.g., CT, cone beam CT and/or MRI scanning). In other embodiments, it may be arranged for use in an operating room and a sterile environment for open surgical or laparoscopic surgical and endoscopic application, or in a robotically enabled operating room, and used alone, or as part of a surgical robotics procedure wherein a surgical robot conducts specific tasks before, during or after use of the system and delivery of acoustic cavitation/histotripsy. As such and depending on the procedure environment based on the aforementioned embodiments, the cart may be positioned to provide sufficient work-space and access to various anatomical locations on the patient (e.g., torso, abdomen, flank, head and neck, etc.), as well as providing work-space for other systems (e.g., anesthesia cart, laparoscopic tower, surgical robot, endoscope tower, etc.).

The Cart may also work with a patient surface (e.g., table or bed) to allow the patient to be presented and repositioned in a plethora of positions, angles and orientations, including allowing changes to such to be made pre, peri and post-procedurally. It may further comprise the ability to interface and communicate with one or more external imaging or image data management and communication systems, not limited to ultrasound, CT, fluoroscopy, cone beam CT, PET, PET/CT, MRI, optical, ultrasound, and image fusion and or image flow, of one or more modalities, to support the procedures and/or environments of use, including physical/mechanical interoperability (e.g., compatible within cone beam CT work-space for collecting imaging data pre, peri and/or post histotripsy) and to provide access to and display of patient medical data including but not limited to laboratory and historical medical record data.

In some embodiments one or more Carts may be configured to work together. As an example, one Cart may comprise a bedside mobile Cart equipped with one or more Robotic arms enabled with a Therapy transducer, and Therapy generator/amplifier, etc., while a companion cart working in concert and at a distance of the patient may comprise Integrated Imaging and a console/display for controlling the Robotic and Therapy facets, analogous to a surgical robot and master/slave configurations.

In some embodiments, the system may comprise a plurality of Carts, all slave to one master Cart, equipped to conduct acoustic cavitation procedures. In some arrangements and cases, one Cart configuration may allow for storage of specific sub-systems at a distance reducing operating room clutter, while another in concert Cart may comprise essentially bedside sub-systems and componentry (e.g., delivery system and therapy).

One can envision a plethora of permutations and configurations of Cart design, and these examples are in no way limiting the scope of the disclosure.

Histotripsy

Histotripsy comprises short, high amplitude, focused ultrasound pulses to generate a dense, energetic, “bubble cloud”, capable of the targeted fractionation and destruction of tissue. Histotripsy is capable of creating controlled tissue erosion when directed at a tissue interface, including tissue/fluid interfaces, as well as well-demarcated tissue fractionation and destruction, at sub-cellular levels, when it is targeted at bulk tissue. Unlike other forms of ablation, including thermal and radiation-based modalities, histotripsy does not rely on heat cold or ionizing (high) energy to treat tissue. Instead, histotripsy uses acoustic cavitation generated at the focus to mechanically effect tissue structure, and in some cases liquefy, suspend, solubilize and/or destruct tissue into sub-cellular components.

Histotripsy can be applied in various forms, including: 1) Intrinsic-Threshold Histotripsy: Delivers pulses with a 1-2 cycles of high amplitude negative/tensile phase pressure exceeding the intrinsic threshold to generate cavitation in the medium (e.g., ~24-28 MPa for water-based soft tissue), 2) Shock-Scattering Histotripsy: Delivers typically pulses 3-20 cycles in duration. The shockwave (positive/compressive phase) scattered from an initial individual microbubble generated forms inverted shockwave, which constructively interfere with the incoming negative/tensile phase to form high amplitude negative/rarefactional phase exceeding the intrinsic threshold. In this way, a cluster of cavitation microbubbles is generated. The amplitude of the tensile phases of the pulses is sufficient to cause bubble nuclei in the medium to undergo inertial cavitation within the focal zone throughout the duration of the pulse. These nuclei scatter the incident shockwaves, which invert and constructively interfere with the incident wave to exceed the threshold for intrinsic nucleation, and 3) Boiling Histotripsy: Employs pulses roughly 1-20 ms in duration. Absorption of the shocked pulse rapidly heats the medium, thereby reducing the threshold for intrinsic nuclei. Once this intrinsic threshold coincides with the peak negative pressure of the incident wave, boiling bubbles form at the focus.

The large pressure generated at the focus causes a cloud of acoustic cavitation bubbles to form above certain thresholds, which creates localized stress and strain in the tissue and mechanical breakdown without significant heat deposition. At pressure levels where cavitation is not generated, minimal effect is observed on the tissue at the focus. This cavitation effect is observed only at pressure levels significantly greater than those which define the inertial cavitation threshold in water for similar pulse durations, on the order of 10 to 30 MPa peak negative pressure.

Histotripsy may be performed in multiple ways and under different parameters. It may be performed totally non-invasively by acoustically coupling a focused ultrasound transducer over the skin of a patient and transmitting acoustic pulses transcutaneously through overlying (and intervening) tissue to the focal zone (treatment zone and site). The application of histotripsy is not limited to a transdermal approach but can be applied through any means that allows contact of the transducer with tissue including open surgical laparoscopic surgical, percutaneous and robotically mediated surgical procedures. It may be further targeted, planned, directed and observed under direct visualization, via ultrasound imaging, given the bubble clouds generated by histotripsy may be visible as highly dynamic, echogenic regions on, for example, B Mode ultrasound images, allowing continuous visualization through its use (and related procedures). Likewise, the treated and fractionated tissue shows a dynamic change in echogenicity (typically a reduction), which can be used to evaluate, plan, observe and monitor treatment.

Generally, in histotripsy treatments, ultrasound pulses with 1 or more acoustic cycles are applied, and the bubble cloud formation relies on the pressure release scattering of the positive shock fronts (sometimes exceeding 100 MPa, P+) from initially initiated, sparsely distributed bubbles (or a single bubble). This is referred to as the "shock scattering mechanism".

This mechanism depends on one (or a few sparsely distributed) bubble(s) initiated with the initial negative half cycle(s) of the pulse at the focus of the transducer. A cloud of microbubbles then forms due to the pressure release backscattering of the high peak positive shock fronts from these sparsely initiated bubbles. These back-scattered high-amplitude rarefactional waves exceed the intrinsic threshold thus producing a localized dense bubble cloud. Each of the following acoustic cycles then induces further cavitation by the backscattering from the bubble cloud surface, which grows towards the transducer. As a result, an elongated dense bubble cloud growing along the acoustic axis opposite the ultrasound propagation direction is observed with the shock scattering mechanism. This shock scattering process makes the bubble cloud generation not only dependent on the peak negative pressure, but also the number of acoustic cycles and the amplitudes of the positive shocks. Without at least one intense shock front developed by nonlinear propagation, no dense bubble clouds are generated when the peak negative half-cycles are below the intrinsic threshold.

When ultrasound pulses less than 2 cycles are applied, shock scattering can be minimized, and the generation of a dense bubble cloud depends on the negative half cycle(s) of the applied ultrasound pulses exceeding an "intrinsic threshold" of the medium. This is referred to as the "intrinsic threshold mechanism".

This threshold can be in the range of 26-30 MPa for soft tissues with high water content, such as tissues in the human body. In some embodiments, using this intrinsic threshold mechanism, the spatial extent of the lesion may be well-defined and more predictable. With peak negative pressures (P−) not significantly higher than this threshold, sub-wavelength reproducible lesions as small as half of the −6 dB beam width of a transducer may be generated.

With high-frequency Histotripsy pulses, the size of the smallest reproducible lesion becomes smaller, which is beneficial in applications that require precise lesion generation. However, high-frequency pulses are more susceptible to attenuation and aberration, rendering problematical treatments at a larger penetration depth (e.g., ablation deep in the body) or through a highly aberrative medium (e.g., transcranial procedures, or procedures in which the pulses are transmitted through bone(s)). Histotripsy may further also be applied as a low-frequency "pump" pulse (typically <2 cycles and having a frequency between 100 kHz and 1 MHZ) can be applied together with a high-frequency "probe" pulse (typically <2 cycles and having a frequency greater than 2 MHz, or ranging between 2 MHz and 10 MHz) wherein the peak negative pressures of the low and high-frequency pulses constructively interfere to exceed the intrinsic threshold in the target tissue or medium. The low-frequency pulse, which is more resistant to attenuation and aberration, can raise the peak negative pressure P− level for a region of interest (ROI), while the high-frequency pulse, which provides more precision, can pin-point a targeted location within the ROI and raise the peak negative pressure P− above the intrinsic threshold. This approach may be referred to as "dual frequency", "dual beam histotripsy" or "parametric histotripsy."

Additional systems, methods and parameters to deliver optimized histotripsy, using shock scattering, intrinsic threshold, and various parameters enabling frequency compounding and bubble manipulation, are herein included as part of the system and methods disclosed herein, including additional means of controlling said histotripsy effect as pertains to steering and positioning the focus, and concurrently managing tissue effects (e.g., prefocal thermal collateral damage) at the treatment site or within intervening tissue. Further, it is disclosed that the various systems and methods, which may include a plurality of parameters, such as but not limited to, frequency, operating frequency, center frequency, pulse repetition frequency, pulses, bursts, number of pulses, cycles, length of pulses, amplitude of pulses, pulse period, delays, burst repetition frequency, sets of the former, loops of multiple sets, loops of multiple and/or different sets, sets of loops, and various combinations or permutations of, etc., are included as a part of this disclosure, including future envisioned embodiments of such.

Therapy Components

The Therapy sub-system may work with other sub-systems to create, optimize, deliver, visualize, monitor and control acoustic cavitation, also referred to herein and in following as "histotripsy", and its derivatives of, including boiling histotripsy and other thermal high frequency ultrasound approaches. It is noted that the disclosed inventions may also further benefit other acoustic therapies that do not comprise a cavitation, mechanical or histotripsy component. The therapy sub-system can include, among other features, an ultrasound therapy transducer and a pulse generator system configured to deliver ultrasound pulses into tissue.

In order to create and deliver histotripsy and derivatives of histotripsy, the therapy sub-system may also comprise components, including but not limited to, one or more function generators, amplifiers, therapy transducers and power supplies.

The therapy transducer can comprise a single element or multiple elements configured to be excited with high amplitude electric pulses (>1000V or any other voltage that can cause harm to living organisms). The amplitude necessary to drive the therapy transducers for Histotripsy vary depending on the design of the transducer and the materials used (e.g., solid or polymer/piezoelectric composite including ceramic or single crystal) and the transducer center frequency which is directly proportional to the thickness of the piezo-electric material. Transducers therefore operating at a high frequency require lower voltage to produce a given surface pressure than is required by low frequency therapy transducers. In some embodiments, the transducer elements are formed using a piezoelectric-polymer composite material or a solid piezoelectric material. Further, the piezoelectric material can be of polycrystalline/ceramic or single crystalline formulation. In some embodiments the transducer elements can be formed using silicon using MEMs technology, including CMUT and PMUT designs.

In some embodiments, the function generator may comprise a field programmable gate array (FPGA) or other suitable function generator. The FPGA may be configured with parameters disclosed previously herein, including but not limited to frequency, pulse repetition frequency, bursts, burst numbers, where bursts may comprise pulses, numbers of pulses, length of pulses, pulse period, delays, burst repetition frequency or period, where sets of bursts may comprise a parameter set, where loop sets may comprise various parameter sets, with or without delays, or varied delays, where multiple loop sets may be repeated and/or new loop sets introduced, of varied time delay and independently controlled, and of various combinations and permutations of such, overall and throughout.

In some embodiments, the generator or amplifier may be configured to be a universal single-cycle or multi-cycle pulse generator, and to support driving via Class D or inductive driving, as well as across all envisioned clinical applications, use environments, also discussed in part later in this disclosure. In other embodiments, the class D or inductive current driver may be configured to comprise transformer and/or auto-transformer driving circuits to further provide step up/down components, and in some cases, to preferably allow a step up in the amplitude. They may also comprise specific protective features, to further support the system, and provide capability to protect other parts of the system (e.g., therapy transducer and/or amplifier circuit components) and/or the user, from various hazards, including but not limited to, electrical safety hazards, which may potentially lead to use environment, system and therapy system, and user harms, damage or issues.

Disclosed generators may allow and support the ability of the system to select, vary and control various parameters (through enabled software tools), including, but not limited to those previously disclosed, as well as the ability to start/stop therapy, set and read voltage level, pulse and/or burst repetition frequency, number of cycles, duty ratio, channel enabled and delay, etc., modulate pulse amplitude on a fast time-scale independent of a high voltage supply, and/or other service, diagnostic or treatment features.

In some embodiments, the Therapy sub-system and/or components of, such as the amplifier, may comprise further integrated computer processing capability and may be networked, connected, accessed, and/or be removable/portable, modular, and/or exchangeable between systems, and/or driven/commanded from/by other systems, or in various combinations. Other systems may include other acoustic cavitation/histotripsy, HIFU, HITU, radiation therapy, radiofrequency, microwave, and cryoablation systems, navigation and localization systems, open surgical, laparoscopic, single incision/single port, endoscopic and non-invasive surgical robots, laparoscopic or surgical towers comprising other energy-based or vision systems, surgical system racks or booms, imaging carts, etc.

In some embodiments, one or more amplifiers may comprise a Class D amplifier and related drive circuitry including matching network components. Depending on the transducer element electric impedance and choice of the matching network components (e.g., an LC circuit made of an inductor L1 in series and the capacitor C1 in parallel), the combined impedance can be aggressively set low in order to have high amplitude electric waveform necessary to drive the transducer element. The maximum amplitude that Class D amplifiers is dependent on the circuit components used, including the driving MOSFET/IGBT transistors, matching network components or inductor, and transformer or autotransformer, and of which may be typically in the low kV (e.g., 1-3 kV) range.

Therapy transducer element(s) are excited with an electrical waveform with an amplitude (voltage) to produce a pressure output sufficient for Histotripsy therapy. The excitation electric field can be defined as the necessary waveform voltage per thickness of the piezoelectric element. For example, because a piezoelectric element operating at 1 MHz transducer is half the thickness of an equivalent 500 kHz element, it will require half the voltage to achieve the same electric field and surface pressure.

The Therapy sub-system may also comprise therapy transducers of various designs and working parameters, supporting use in various procedures (and procedure settings). Systems may be configured with one or more therapy transducers, that may be further interchangeable, and work with various aspects of the system in similar or different ways (e.g., may interface to a robotic arm using a common interface and exchange feature, or conversely, may adapt to work differently with application specific imaging probes, where different imaging probes may interface and integrate with a therapy transducer in specifically different ways).

Therapy transducers may be configured of various parameters that may include size, shape (e.g., rectangular or round; anatomically curved housings, etc.), geometry, focal length, number of elements, size of elements, distribution of elements (e.g., number of rings, size of rings for annular patterned transducers), frequency, enabling electronic beam steering, etc. Transducers may be composed of various materials (e.g., piezoelectric, silicon, etc.), form factors and types (e.g., machined elements, chip-based, etc.) and/or by various methods of fabrication.

Transducers may be designed and optimized for clinical applications (e.g., abdominal tumors, peripheral vascular disease, fat ablation, etc.) and desired outcomes (e.g., acoustic cavitation/histotripsy without thermal injury to intervening tissue), and affording a breadth of working ranges, including relatively shallow and superficial targets (e.g., thyroid or breast nodules), versus, deeper or harder to reach targets, such as central liver or brain tumors. They may be configured to enable acoustic cavitation/histotripsy under various parameters and sets of, as enabled by the aforementioned system components (e.g., function generator and amplifier, etc.), including but not limited to frequency, pulse repetition rate, pulses, number of pulses, pulse length, pulse period, delays, repetitions, sync delays, sync period, sync pulses, sync pulse delays, various loop sets, others, and permutations of. The transducer may also be designed to allow for the activation of a drug payload either deposited in tissue through various means including injection, placement or delivery in micelle or nanostructures.

Integrated Imaging

The disclosed system may comprise various imaging modalities to allow users to visualize, monitor and collect/use feedback of the patient's anatomy, related regions of interest and treatment/procedure sites, as well as surrounding and intervening tissues to assess, plan and conduct procedures, and adjust treatment parameters as needed. Imaging modalities may comprise various ultrasound, x-ray, CT, MRI, PET, fluoroscopy, optical, contrast or agent enhanced versions, and/or various combinations of. It is further disclosed that various image processing and characterization technologies may also be utilized to afford enhanced visualization and user decision making. These may be selected or commanded manually by the user or in an automated fashion by the system. The system may be configured to allow side by side, toggling, overlays, 3D reconstruction, segmentation, registration, multi-modal image fusion, image flow, and/or any methodology affording the user to identify, define and inform various aspects of using imaging during the procedure, as displayed in the various system user interfaces and displays. Examples may include locating, displaying and characterizing regions of interest, organ systems, potential treatment sites within, with on and/or surrounding organs or tissues, identifying critical structures such as ducts, vessels, nerves, ureters, fissures, capsules, tumors, tissue trauma/injury/disease, other organs, connective tissues, etc., and/or in context to one another, of one or more (e.g., tumor draining lymphatics or vasculature; or tumor proximity to organ capsule or underlying other organ), as unlimited examples.

Systems may be configured to include onboard integrated imaging hardware, software, sensors, probes and wetware, and/or may be configured to communicate and interface with external imaging and image processing systems. The aforementioned components may be also integrated into the system's Therapy sub-system components wherein probes, imaging arrays, or the like, and electrically, mechanically or electromechanically integrated into therapy transducers. This may afford, in part, the ability to have geometrically aligned imaging and therapy, with the therapy directly within the field of view, and in some cases in line, with imaging. In some embodiments, this integration may comprise a fixed orientation of the imaging capability (e.g., imaging probe) in context to the therapy transducer. In other embodiments, the imaging solution may be able to move or adjust its position, including modifying angle, extension (e.g., distance from therapy transducer or patient), rotation (e.g., imaging plane in example of an ultrasound probe) and/or other parameters, including moving/adjusting dynamically while actively imaging. The imaging component or probe may be encoded so its orientation and position relative to another aspect of the system, such as the therapy transducer, and/or robotically-enabled positioning component may be determined.

In one embodiment, the system may comprise onboard ultrasound, further configured to allow users to visualize, monitor and receive feedback for procedure sites through the system displays and software, including allowing ultrasound imaging and characterization (and various forms of), ultrasound guided planning and ultrasound guided treatment, all in real-time. The system may be configured to allow users to manually, semi-automated or in fully automated means image the patient (e.g., by hand or using a robotically-enabled imager).

In some embodiments, imaging feedback and monitoring can include monitoring changes in: backscatter from bubble clouds; speckle reduction in backscatter; backscatter speckle statistics; mechanical properties of tissue (i.e., elastography); tissue perfusion (i.e., ultrasound contrast); shear wave propagation; acoustic emissions, electrical impedance tomography, and/or various combinations of, including as displayed or integrated with other forms of imaging (e.g., CT or MRI).

In some embodiments, imaging including feedback and monitoring from backscatter from bubble clouds, may be used as a method to determine immediately if the histotripsy process has been initiated, is being properly maintained, or even if it has been extinguished. For example, this method enables continuously monitored in real time drug delivery, tissue erosion, and the like. The method also can provide feedback permitting the histotripsy process to be initiated at a higher intensity and maintained at a much lower intensity. For example, backscatter feedback can be monitored by any transducer or ultrasonic imager. By measuring feedback for the therapy transducer, an accessory transducer can send out interrogation pulses or be configured to passively detect cavitation. Moreover, the nature of the feedback received can be used to adjust acoustic parameters (and associated system parameters) to optimize the drug delivery and/or tissue erosion process.

In some embodiments, imaging including feedback and monitoring from backscatter, and speckle reduction, may be configured in the system.

For systems comprising feedback and monitoring via backscattering, and as means of background, as tissue is progressively mechanically subdivided, in other words homogenized, disrupted, or eroded tissue, this process results in changes in the size and distribution of acoustic scatter. At some point in the process, the scattering particle size and density is reduced to levels where little ultrasound is scattered, or the amount scattered is reduced significantly. This results in a significant reduction in speckle, which is the coherent constructive and destructive interference patterns of light and dark spots seen on images when coherent sources of illumination are used; in this case, ultrasound. After some treatment time, the speckle reduction results in a dark area in the therapy volume. Since the amount of speckle reduction is related to the amount of tissue subdivision, it can be related to the size of the remaining tissue fragments. When this size is reduced to sub-cellular levels, no cells are assumed to have survived. So, treatment can proceed until a desired speckle reduction level has been reached. Speckle is easily seen and evaluated on standard ultrasound imaging systems. Specialized transducers and systems, including those disclosed herein, may also be used to evaluate the backscatter changes.

Further, systems comprising feedback and monitoring via speckle, and as means of background, an image may persist from frame to frame and change very little as long as the scatter distribution does not change and there is no movement of the imaged object. However, long before the scatters are reduced enough in size to cause speckle reduction, they may be changed sufficiently to be detected by signal processing and other means. This family of techniques can operate as detectors of speckle statistics changes. For example, the size and position of one or more speckles in an image will begin to decorrelate before observable speckle reduction occurs. Speckle decorrelation, after appropriate motion compensation, can be a sensitive measure of the mechanical disruption of the tissues, and thus a measure of therapeutic efficacy. This feedback and monitoring technique may permit early observation of changes resulting from the acoustic cavitation/histotripsy process and can identify changes in tissue before substantial or complete tissue effect (e.g., erosion occurs). In one embodiment, this method may be used to monitor the acoustic cavitation/histotripsy process for enhanced drug delivery where treatment sites/tissue is temporally disrupted, and tissue damage/erosion is not desired. In other embodiments, this may comprise speckle decorrelation by movement of scatters in an increasingly fluidized therapy volume. For example, in the case where partial or complete tissue erosion is desired.

For systems comprising feedback and monitoring via elastography, and as means of background, as treatment sites/tissue are further subdivided per an acoustic cavitation/histotripsy effect (homogenized, disrupted, or eroded), its mechanical properties change from a soft but interconnected solid to a viscous fluid or paste with few long-range interactions. These changes in mechanical properties can be measured by various imaging modalities including MRI and ultrasound imaging systems. For example, an ultrasound pulse can be used to produce a force (i.e., a radiation force) on a localized volume of tissue. The tissue response (displacements, strains, and velocities) can change significantly during histotripsy treatment allowing the state of tissue disruption to be determined by imaging or other quantitative means.

Systems may also comprise feedback and monitoring via shear wave propagation changes. As means of background, the subdivision of tissues makes the tissue more fluid and less solid and fluid systems generally do not propagate shear waves. Thus, the extent of tissue fluidization provides opportunities for feedback and monitoring of the histotripsy process. For example, ultrasound and MRI imaging systems can be used to observe the propagation of shear waves. The extinction of such waves in a treated volume is used as a measure of tissue destruction or disruption. In one system embodiment, the system and supporting sub-systems may be used to generate and measure the interacting shear waves. For example, two adjacent ultrasound foci might perturb tissue by pushing it in certain ways. If adjacent foci are in a fluid, no shear waves propagate to interact with each other. If the tissue is not fluidized, the interaction would be detected with external means, for example, by a difference frequency only detected when two shear waves interact nonlinearly, with their disappearance correlated to tissue damage. As such, the system may be configured to use this modality to enhance feedback and monitoring of the acoustic cavitation/histotripsy procedure.

For systems comprising feedback and monitoring via acoustic emission, and as means of background, as a tissue volume is subdivided, its effect on acoustic cavitation/histotripsy (e.g., the bubble cloud here) is changed. For example, bubbles may grow larger and have a different lifetime and collapse changing characteristics in intact versus fluidized tissue. Bubbles may also move and interact after tissue is subdivided producing larger bubbles or cooperative interaction among bubbles, all of which can result in changes in acoustic emission. These emissions can be heard during treatment and they change during treatment. Analysis of these changes, and their correlation to therapeutic efficacy, enables monitoring of the progress of therapy, and may be configured as a feature of the system.

For systems comprising feedback and monitoring via electrical impedance tomography, and as means of background, an impedance map of a therapy site can be produced based upon the spatial electrical characteristics throughout the therapy site. Imaging of the conductivity or permittivity of the therapy site of a patient can be inferred from taking skin surface electrical measurements. Conducting electrodes are attached to a patient's skin and small alternating currents are applied to some or all of the electrodes. One or more known currents are injected into the surface and the voltage is measured at a number of points using the electrodes. The process can be repeated for different configurations of applied current. The resolution of the resultant image can be adjusted by changing the number of electrodes employed. A measure of the electrical properties of the therapy site within the skin surface can be obtained from the impedance map, and changes in and location of the acoustic cavitation/histotripsy (e.g., bubble cloud, specifically) and histotripsy process can be monitored using this as configured in the system and supporting sub-systems.

The user may be allowed to further select, annotate, mark, highlight, and/or contour, various regions of interest or treatment sites, and defined treatment targets (on the image(s)), of which may be used to command and direct the system where to image, test and/or treat, through the system software and user interfaces and displays. In some arrangements, the user may use a manual ultrasound probe (e.g., diagnostic hand-held probe) to conduct the procedure. In another arrangement, the system may use a robot and/or electromechanical positioning system to conduct the procedure, as directed and/or automated by the system, or conversely, the system can enable combinations of manual and automated uses.

The system may further include the ability to conduct image registration, including imaging and image data set registration to allow navigation and localization of the system to the patient, including the treatment site (e.g., tumor, critical structure, bony anatomy, anatomy and identifying features of, etc.). In one embodiment, the system allows the user to image and identify a region of interest, for example the liver, using integrated ultrasound, and to select and mark a tumor (or surrogate marker of) comprised within the liver through/displayed in the system software, and wherein said system registers the image data to a coordinate system defined by the system, that further allows the system's Therapy and Robotics sub-systems to deliver synchronized acoustic cavitation/histotripsy to said marked tumor. The system may comprise the ability to register various image sets, including those previously disclosed, to one another, as well as to afford navigation and localization (e.g., of a therapy transducer to a CT or MRI/ultrasound fusion image with the therapy transducer and Robotics sub-system tracking to said image).

The system may also comprise the ability to work in a variety of interventional, endoscopic and surgical environments, including alone and with other systems (surgical/laparoscopic towers, vision systems, endoscope systems and towers, ultrasound enabled endoscopic ultrasound (flexible and rigid), percutaneous/endoscopic/laparoscopic and minimally invasive navigation systems (e.g., optical, electromagnetic, shape-sensing, ultrasound-enabled, etc.), of also which may work with, or comprise various optical imaging capabilities (e.g., fiber and or digital). The disclosed system may be configured to work with these systems, in some embodiments working alongside them in concert, or in other embodiments where all or some of the system may be integrated into the above systems/platforms (e.g., acoustic cavitation/histotripsy-enabled endoscope system or laparoscopic surgical robot). In many of these environments, a therapy transducer may be utilized at or around the time of use, for example, of an optically guided endoscope/bronchoscope, or as another example, at the time a laparoscopic robot (e.g., Intuitive Da Vinci* Xi system) is viewing/manipulating a tissue/treatment site. Further, these embodiments and examples may include where said other systems/platforms are used to deliver (locally) fluid to enable the creation of a man-made acoustic window, where on under normal circumstances may not exist (e.g., fluidizing a segment or lobe of the lung in preparation for acoustic cavitation/histotripsy via non-invasive transthoracic treatment (e.g., transducer externally placed on/around patient). Systems disclosed herein may also comprise all or some of their sub-system hardware packaged within the other system cart/console/systems described here (e.g., acoustic cavitation/histotripsy system and/or sub-systems integrated and operated from said navigation or laparoscopic system).

The system may also be configured, through various aforementioned parameters and other parameters, to display real-time visualization of a bubble cloud in a spatial-temporal manner, including the resulting tissue effect peri/post-treatment from tissue/bubble cloud interaction, wherein the system can dynamically image and visualize, and display, the bubble cloud, and any changes to it (e.g., decreasing or increasing echogenicity), which may include intensity, shape, size, location, morphology, persistence, etc. These features may allow users to continuously track and follow the treatment in real-time in one integrated procedure and interface/system, and confirm treatment safety and efficacy on the fly (versus other interventional or surgical modalities, which either require multiple procedures to achieve the same, or where the treatment effect is not visible in real-time (e.g., radiation therapy), or where it is not possible to achieve such (e.g., real-time visualization of local tissue during thermal ablation), and/or where the other procedure further require invasive approaches (e.g., incisions or punctures) and iterative imaging in a scanner between procedure steps (e.g., CT or MRI scanning). The above disclosed systems, sub-systems, components, modalities, features and work-flows/methods of use may be implemented in an unlimited fashion through enabling hardware, software, user interfaces and use environments, and future improvements, enhancements and inventions in this area are considered as included in the scope of this disclosure, as well as any of the resulting data and means of using said data for analytics, artificial intelligence or digital health applications and systems.

Treatment Head

This disclosure provides treatment head designs that typically includes a histotripsy therapy transducer, embedded coaxial ultrasound imaging probe, probe rotation and translation features including positional encoders, and mechanical, electrical and software support and/or related interfaces for controlling various treatment head features and functionality. This includes user various user interaction points and interfaces, including from installation, setup and through clinical procedure workflow(s), as well as procedure simulation and pre-planning support.

Figure 2A:
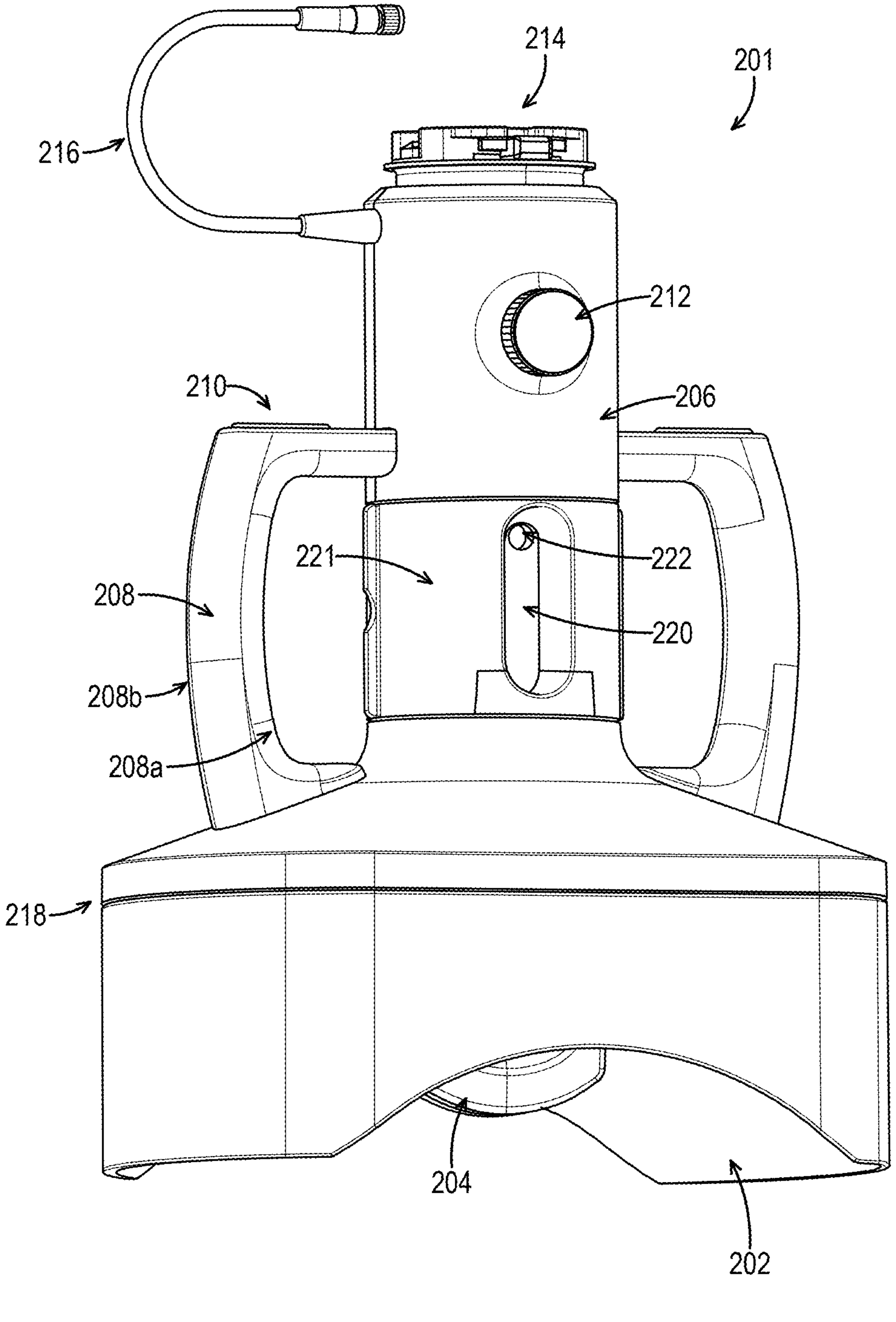
FIGS. 2A-2P are embodiments of a treatment head including a therapy transducer array and an imaging probe.
Figure 2B:
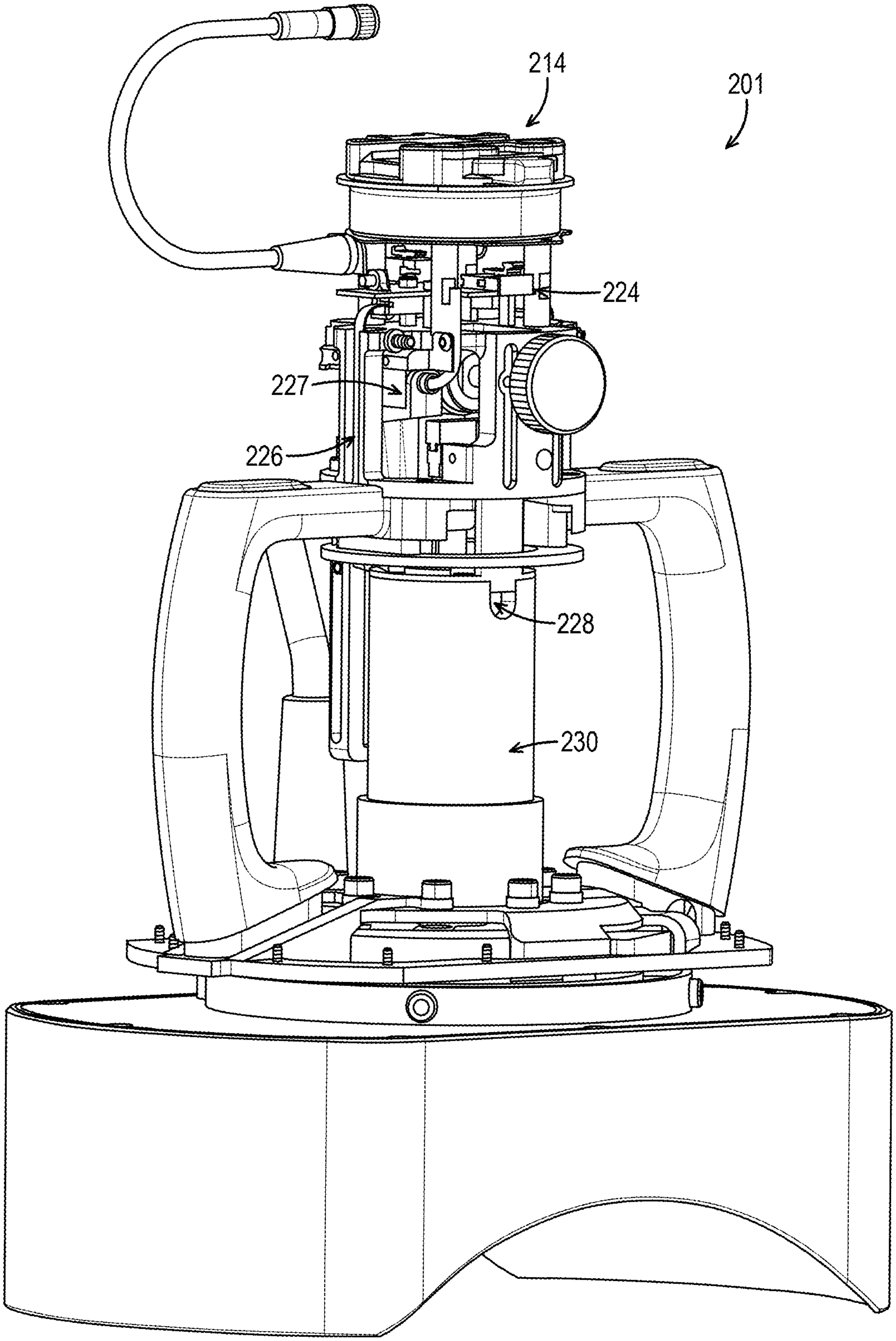

FIG. 2A provides additional details on treatment head 201 of the histotripsy system, which can include a histotripsy or therapy transducer array 202 and an imaging probe 204. The imaging probe 204 can be configured to translate axially and rotate within a bore of the treatment head. The treatment head can comprise a housing 206 which can cover and/or protect internal components of the treatment head. For example, FIG. 2A shows the treatment head with the housing intact, and FIG. 2B shows the treatment head with the housing removed, providing a view of the internal components.

Referring still to FIG. 2A, the treatment head 201 can include one or more handles 208 to allow for physical manipulation of the treatment head. The illustrated embodiment shows a pair of handles 208 opposing another on the treatment head, however it should be understood that less or more than two handles can be incorporated. In some embodiments, the one or more handles 208 can include user input devices 210. The user input devices can include, for example, buttons, levers, switches, graphical user interfaces (GUIs), or the like. The buttons can be, for example, physical buttons or electronic/capacitive buttons. In some implementations, the user input devices 210 can enable or control functionality of the treatment head, or the robotics system upon which the treatment head is mounted. For example, in one embodiment, when depressed or initiated, the user input devices 210 can change a system state from robotic drive control, where the robotic system is entirely responsible for positioning and moving the treatment head, to free-drive control, where a user can move or manipulate a position and/or orientation of the treatment head. Generally, free-drive control can be configured such that the robotics system is configured to support or hold the weight of the treatment head in place in 3D space, but additional force applied by the user to the treatment head may allow for movement or rotation of the treatment head. In some implementations, there can be various degrees or levels of free-drive control. For example, a first level of free drive control may allow the user to only manipulate the treatment head in a single plane (e.g., axially along z-plane, or side to side along either x or y-plane). Other levels of free-drive control may allow for rotation of the treatment head around an axis (e.g., z-axis), movement in more than one plane or axis, etc. In some embodiments, the various degrees or levels of free-drive control can be cycled through or selected with the user input devices 210.

The handles may be further configured to allow/support users to efficiently attach and release the treatment head to/from the robotic arm (including rapid exchange of application specific treatment heads); wherein the handles interface between the top surface (or interface to) of the therapy transducer, and the central stalk of the treatment head (comprising the electrical/mechanical internal components and imaging probe).

In some embodiments, the handle design, profile and geometry may also be designed to preferentially interact with the coupling system (and defined workspace geometry/volume) to allow required positioning within the coupling system (depth, angle, trajectory, etc.) to minimize/avoid collisions, etc. In other embodiments, handles may be monolithic with the treatment head.

In certain embodiments, the handles are configured for ease of manipulation of the treatment head. The handles may be symmetrical or mirror images of one another. As illustrated in at least FIGS. 2A, 2K, the handles are symmetrical and concave in shape. The handles can have a degree of curvature of about 24 degrees along an interior portion 208*a* of the handle (see also FIG. 2P). A corresponding exterior portion 208*b* may also be disposed at a degree of curvature of about 24 degrees. In some embodiments, the degree of curvature of the interior and exterior portions of the handles may range from 20-30 degrees, or alternatively from 15-35 degrees. One or more of the handles may be hollow or carved out such that cables, wires, tape or other electrical and non-electrical components may be run therethrough. In particular, the rotational encoder cable passes through the interior of at least one of the handles and connects up to the PCB. Weight of the overall treatment head is also reduced with hollowed-out handles. To achieve the durability and support desired while maintaining the complex shape and hollowed out design, a direct metal laser sintering process can be used to manufacture the handle components in aluminum.

Additional buttons, dials, knobs, or user input devices can be included in the treatment head. For example, the embodiment of FIG. 2A further includes an imaging probe control 212. The imaging probe control 212 can be configured to control axial movement of the imaging probe 204. In this embodiment the imaging probe control 212 is implemented as a knob or dial. The dial or knob imaging probe control 212 can control axial movement of the imaging probe either electronically via a motor or mechanically, as described below.

In one embodiment, the imaging probe control 212 provides direct mechanical control of axial movement of the imaging probe with respect to the therapy transducer array. For example, rotation of the imaging probe control 212 can control a direct mechanical linkage to the imaging probe, allowing for axial manipulation. Rotation of the imaging probe, on the other hand, can be controlled directly with rotation sleeve 221, which can be directly coupled to the imaging probe (e.g., with a groove and key or other mechanical arrangement). Additional details on the axial and rotational mechanical control of the imaging probe will be described below with respect to the embodiment of FIG. 2E.

In some embodiments, the imaging probe control 212 can control both axial movement and rotation of the imaging probe with respect to the therapy transducer. For example, embodiments can implement an electronic control of the imaging probe via imaging probe control 212, with one or more motors being electrically coupled to the imaging probe control 212 and physically connected or coupled to the imaging probe. In one embodiment, one motor is responsible for axial movement, and a second motor is responsible for rotation, and both can be controlled with the imaging probe control 212 (or a plurality of imaging probe controls).

When the imaging probe control 212 is set to control rotation, rotation of the knob or dial can result in a corresponding rotation of the imaging probe. For example, rotation of the imaging probe control 212 in the clockwise direction may result in a corresponding rotation of the imaging probe in the same clockwise direction (when viewed from the bottom of the therapy head). Alternatively, clockwise rotation of the imaging probe control can result in counter-clockwise rotation of the imaging probe. Any combination of rotation or manipulation of the imaging probe control and rotation of the imaging probe is contemplated. Furthermore, the amount of rotation imparted on the imaging probe relative to the amount of rotation of imaging probe control 212 can be customized. For example, in some embodiments there exists a 1:1 ratio of rotation of the imaging probe control 212 to actual rotation of the imaging probe (i.e., turning the imaging probe control by 90 degrees will result in a corresponding 90 degrees of rotation in the imaging probe). In other embodiments, the ratio may be 1:2, 1:3, 1:4, 2:1 3:1, 4:1, etc. In some embodiments, the ratio can be user-selected depending on user-preferences.

In some embodiments, switching between rotation mode and axial movement mode can be achieved by pushing in on the imaging probe control 212. Alternatively, separate buttons or input devices can be used to switch between modes. Additionally, in some embodiments, separate imaging probe controls 212 can be provided to allow for independent and simultaneous control of both rotation and axial movement. In other embodiments, input devices may be provided that allow for rotation and axial control without having to switch modes (e.g., a joystick or similar input device).

When the imaging probe control is set to control axial movement, rotation of the imaging probe control can result in axial translation of the imaging probe with respect to the therapy transducer. For example, clockwise rotation of the imaging probe control can cause the imaging probe to advance along the z-axis (e.g., extend distally away from the therapy transducer) and counter-clockwise rotation can cause the imaging probe to retract along the z-axis (e.g., extend proximally towards the therapy transducer), or vice versa.

Figure 2C:
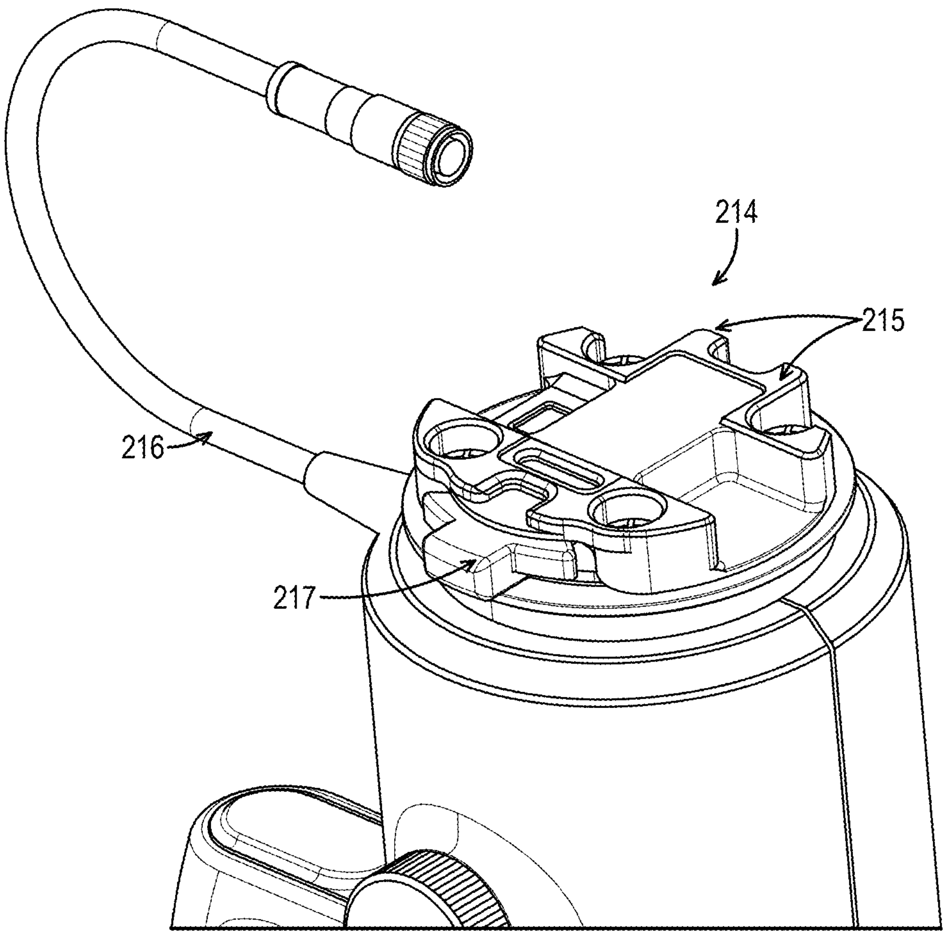
Figure 2D:
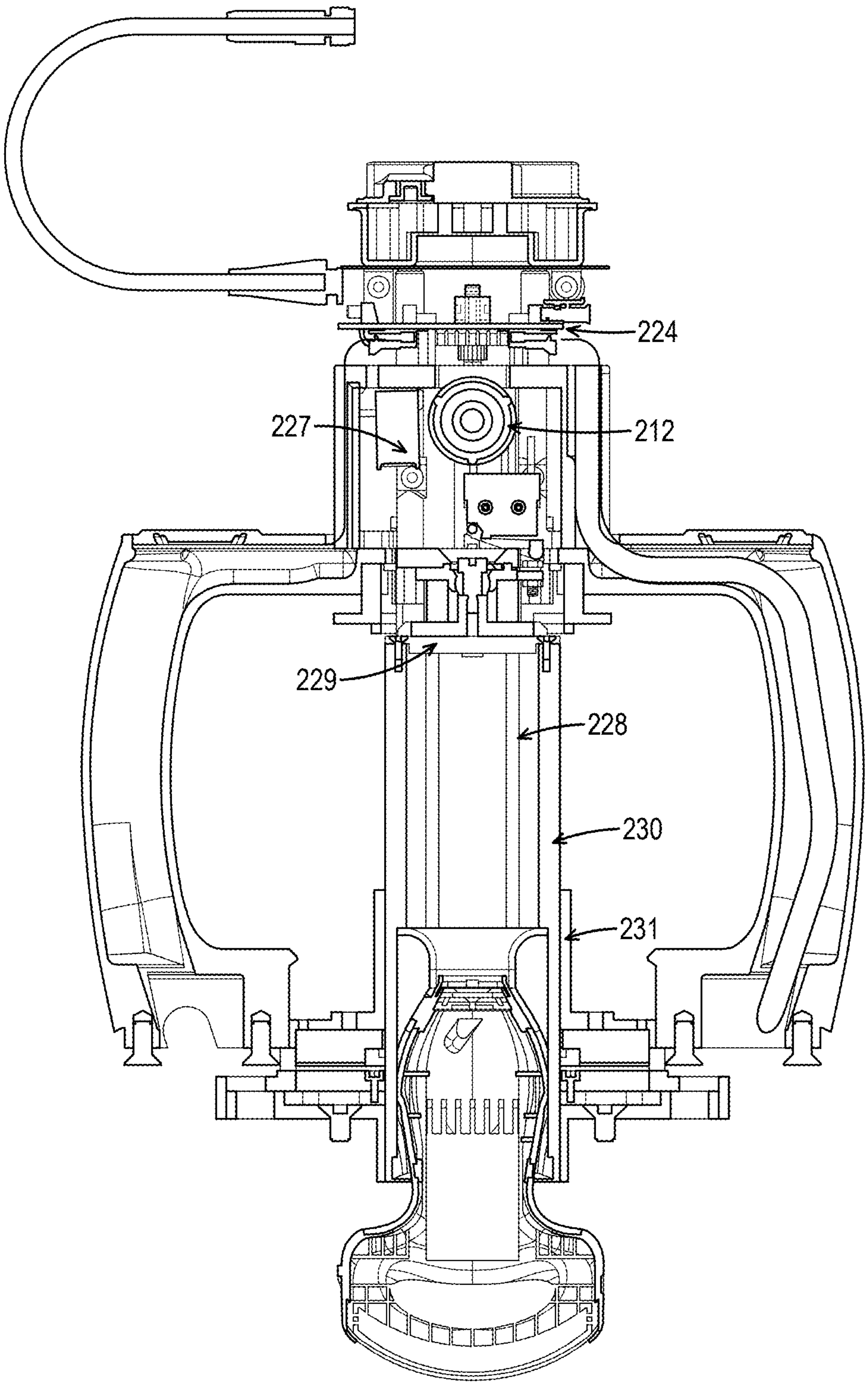
Figure 2E:
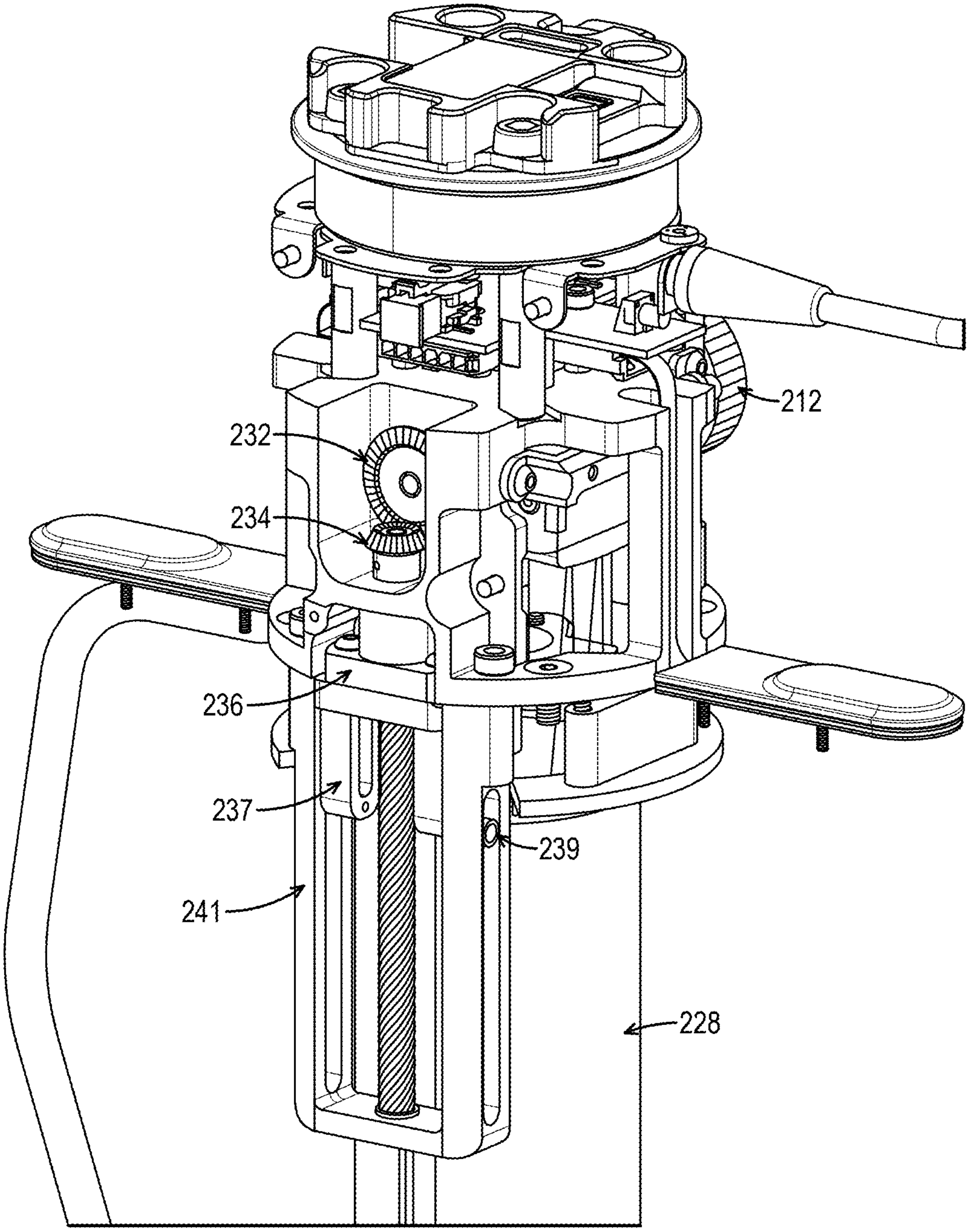
Figure 2F:
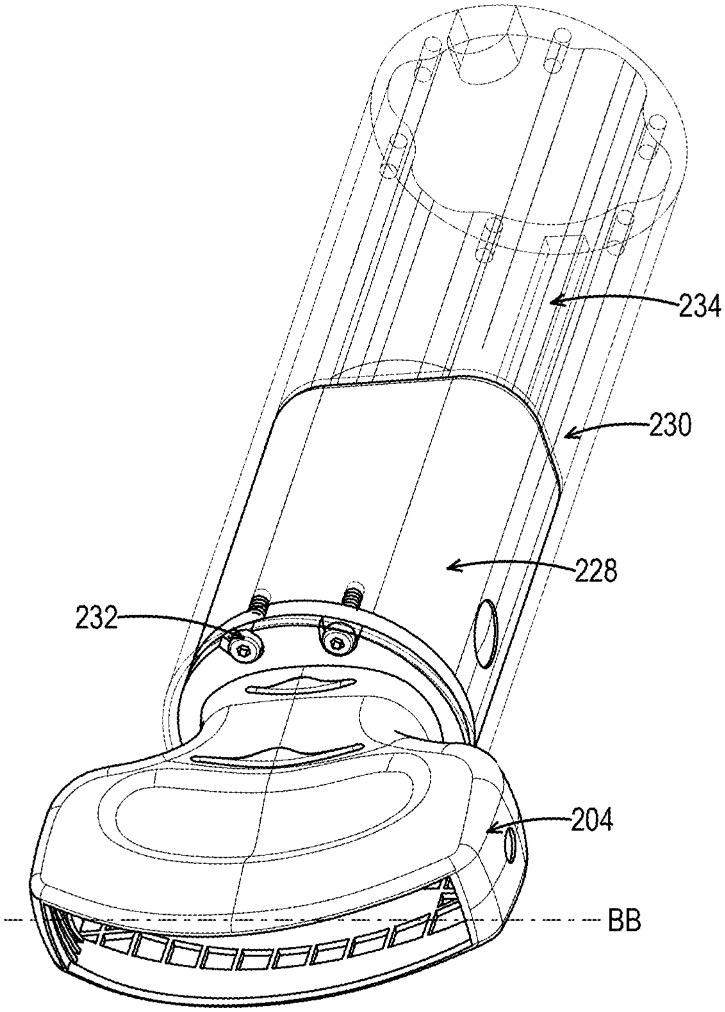
Figure 2G:
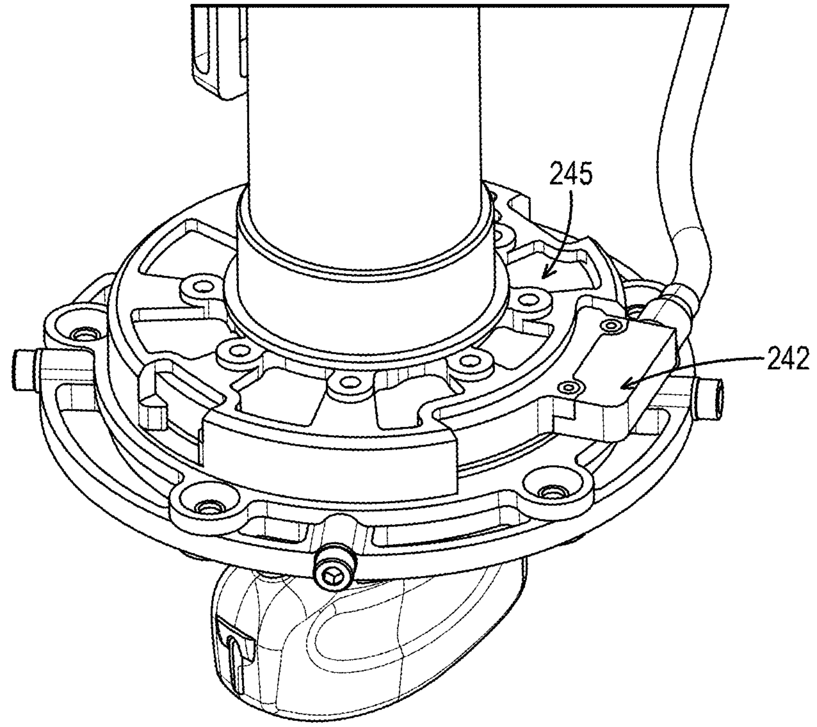

FIGS. 2A and 2C further show robotic arm coupler 214 which is configured to provide a secure connection to the robotic arm of the histotripsy system. FIG. 2C provides a close-up view of the robotic arm coupler 214. In FIG. 2C, the robotic arm coupler can include attachment features 215 which can be configured to securely engage with corresponding attachment features of the robotic arm. In some embodiments, the attachment features of the robotic arm coupler can provide secure attachment to the robotic arm by rotating the treatment head to lock everything in place. Detents in coupler 214 may interact with mating or extension features in the robotic arm. Button 217 can be depressed to release or disconnect the coupler 214 from the robotic arm.

FIGS. 2A and 2C show a separate electrical connection wire 216, which can provide an electrical connection between all the electronics in the treatment head and the console or cart of the histotripsy system. These electrical connections can include, for example, electrical connections to the therapy transducer array, the imaging probe, motors that control rotation/axial movement of the imaging probe, linear and rotational encoders, any of the user input devices, and additionally any other sensors or electronics disposed on or in the treatment head. While a separate electrical connection is shown it should be understood that in other embodiments the electrical connections can be made directly through the robotic arm coupler without requiring a separate connection wire. This implementation could include, for example, electrical contacts configured to mate with corresponding electrical contacts on the robotic arm.

The quick release connector or robotic arm coupler is configured to allow rapid exchange of treatment heads (and designs of), of which may include providing electrical/mechanical support (e.g., connecting encoders to system/system software via the robotic arm I/O at the distal end of the arm/adjacent tool flange). Further, the general interface designs described here include a general mechanical design approach to interface therapy transducer arrays to the central stalk/handles/housings, to allow broad flexibility of therapy transducer design while maintaining a similar treatment head design and interface to a/the robotic arm. Further, the robotic arm and control system, and software as implemented/integrated, may also comprise specific monitoring and watchdogging over various force/torque sensors, and designed to have a force fault system and method for triggering various categories of faults (of various risk/concern level), as well as the ability to alert, notify, interact and recover from one or more types of force faults.

Referring back to FIG. 2A, the treatment head can further include a window 220 configured to provide a view of the imaging probe shaft. In some embodiments, the window 220 can allow the user to visualize the axial position of the imaging probe relative to the therapy transducer array, such as with markings or measurements placed on the imaging probe shaft (not shown). In another embodiment, one or more detents or other protruding features 222 can extend out from the imaging probe shaft to provide a physical stop for the axial translation of the imaging probe. For example, the protruding features 222 can abut or contact the proximal and/or distal ends of the window 220 to maintain axial translation of the imaging probe within prescribed limits. The window 220, may also provide a path for any additional cables or connections to exit the treatment head, such as an ultrasound imaging cable (not shown).

As described above, FIG. 2B provides a view of the internal components of the treatment head 201 with the housing 206 removed. This provides a view of one or more printed circuit boards (PCBs) 224 and or electrical connections 226 which can be configured to provide processing on-board the treatment head and/or electrical connections to the other electrical components, respectively. Additionally, one or more encoders 227 can be provided that track rotation and/or axial movement of the imaging probe. In the illustrated embodiment, only a single encoder 227 is shown for tracking axial movement of the imaging probe. In some embodiments, the measured information from the one or more encoders can be used to update the position of the treatment head, imaging probe, and/or therapy transducer in real-time. In other embodiments, the encoded information on imaging probe position and orientation can be used by the histotripsy therapy system to register images taken by the imaging probe with a robotic positioning coordinate system, a digital treatment plan, and/or other images (e.g., MRI, CT, etc.). As such, the encoder information can be used to support fusion of the ultrasound images with another imaging modality (e.g., CT/MRI, or other medical imaging). Additionally, a shaft or handle 228 of the imaging probe is shown inside coupling assembly 230 of the treatment head. Clearances between the coupling assembly 230 and a bore of the treatment head can be very tight to ensure very precise tracking and movement of the imaging probe/coupling assembly with respect to the therapy transducer array.

As described briefly herein, the treatment head may include positional encoders for rotation and translation, including cable routing and I/O interfaces and support for quick exchanges with an encoded robotic arm, as well as other mechanical components to ensure the imaging probe maintains appropriate alignment within the central bore of the therapy transducer. These can provide either incremental positional feedback (typically relative to a single position sensor), or absolute positional feedback across the entire allowable range in each degree of freedom. Further, the status of probe positions, may be displayed through the system software and user interface(s). In the case of motorized embodiments, the user may interact with various physical controls (dials, etc.) and/or software controls (via software user interface) to manipulate and control probe positions. Further, these controls may be located in various locations on the system (e.g., display control panel, wireless remote controller, etc.).

On the electrical design side as a representative example and embodiment for manual translation, inputs to the PCBs can include a positional sensor for translation, which may comprise a laser positional sensor to track the distance to the stage that moves up and down the geared shaft as the probe is axially translated. The target for the laser can be the stage itself. The sensor connects to the treatment head PCB where it is powered and provides analog voltage output based on position of stage. Both rotational and translational position encoders may also be included. These can provide either incremental positional feedback (typically relative to a single position sensor), or absolute positional feedback across the entire allowable range in each degree of freedom. Encoders can be included in the mechanical design such that they measure motion of the imager tube directly, at the motor shafts directly, or anywhere along the mechanical linkages between them.

In FIG. 2B, an encoder 227 (e.g., a linear encoder) may be disposed in the treatment head. The linear encoder may a laser encoder, provided in a proximal portion (e.g., near the robotic coupler 214) of the treatment head. Position of the linear encoder here enables minimal interference with other mechanical elements of the treatment head. Further, this portion of the treatment head will not typically be submerged or be in contact with acoustic coupling medium and components will therefore remain dry. In some embodiments, the encoder can use a laser to determine a distance between the ultrasound imaging probe (including, for example, a stage or coupler attached to the ultrasound imaging probe) and the encoder. This distance may be conveyed as a voltage to the robot/histotripsy system and displayed to the user on the UI screen. This distance will also be incorporated into planning and treatment of a patient using histotripsy.

FIGS. 2G-21 show a second encoder 242 (e.g., a rotational encoder) located in a distal portion of the treatment head (e.g., near the ultrasound imaging probe). The encoder can be electrically connected to the PCB (e.g., PCB 224 in FIG. 2B) where it is powered and provides analog voltage output based on rotation of a rotor 244 and a stator 245. The rotor 244 can be attached to the keyed plate 246 that rotates with the ultrasound imaging probe as the stator remains fixed. In particular, the stator and rotor components are magnetic and provide feedback as to relative rotation of the rotor with respect to the stator. Rotational information is sent to the robot via the rotational encoder cable 248 which can be run up through a handle and connected to the PCB 224.

Figure 2H:
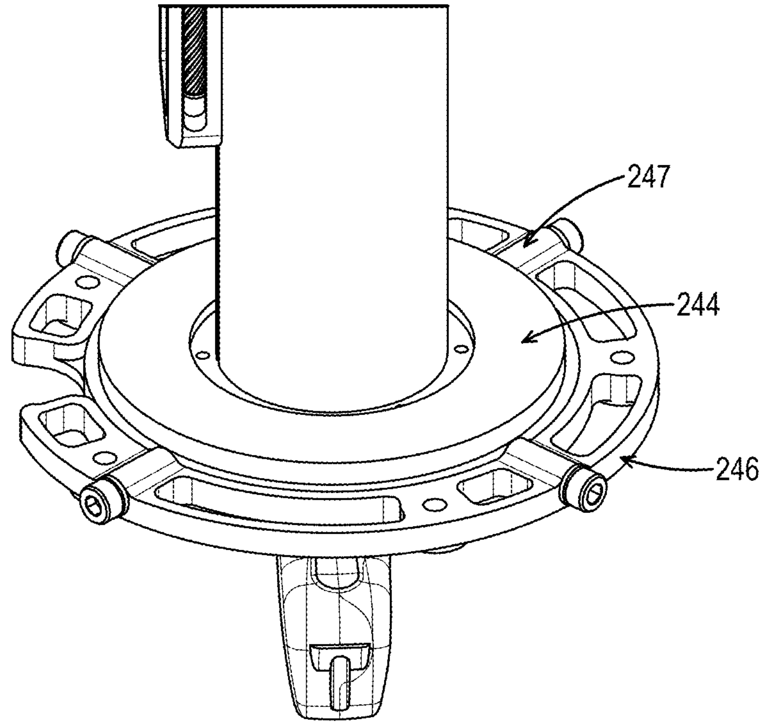
Figure 2I:
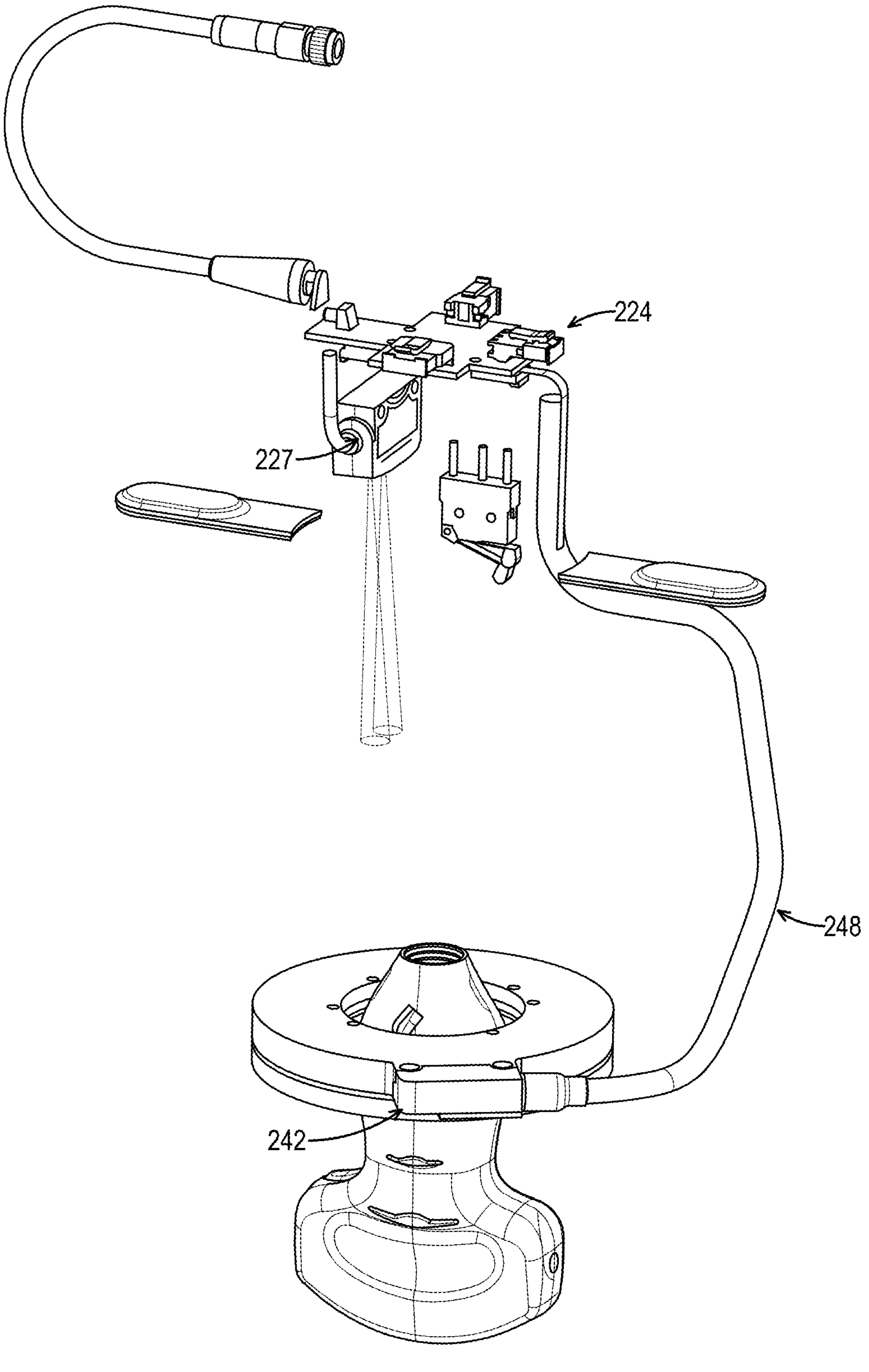
Figure 2J:
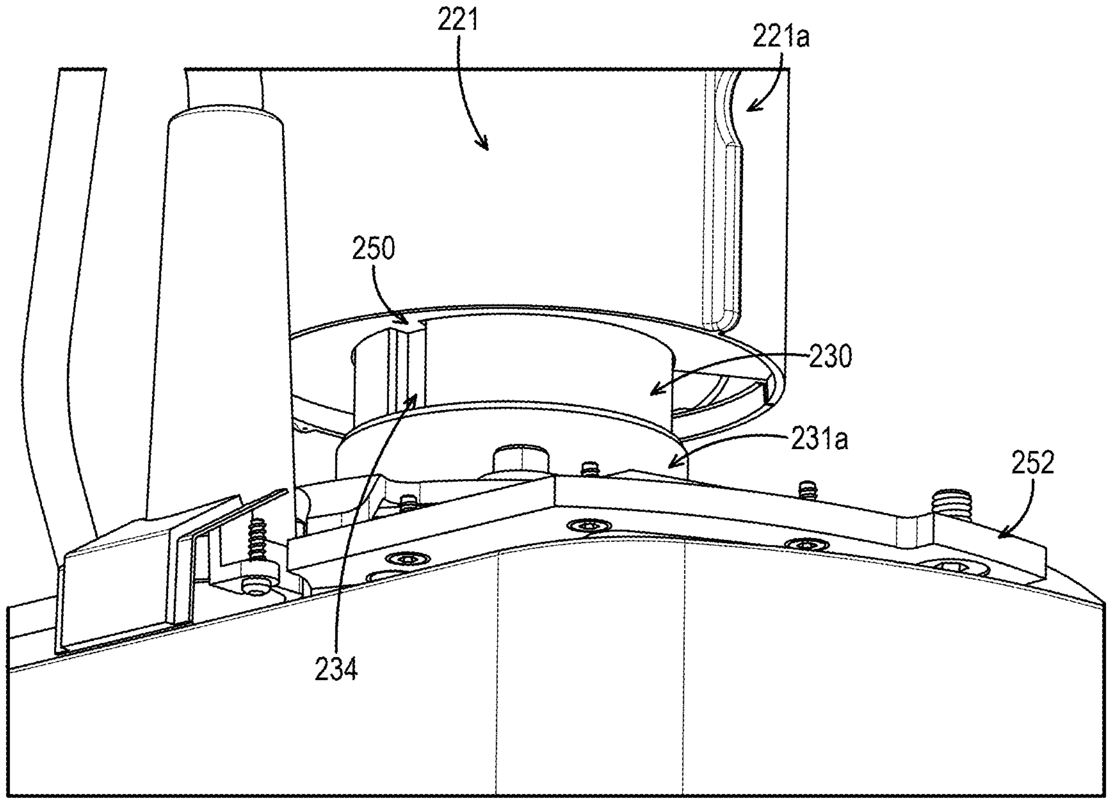
Figure 2K:
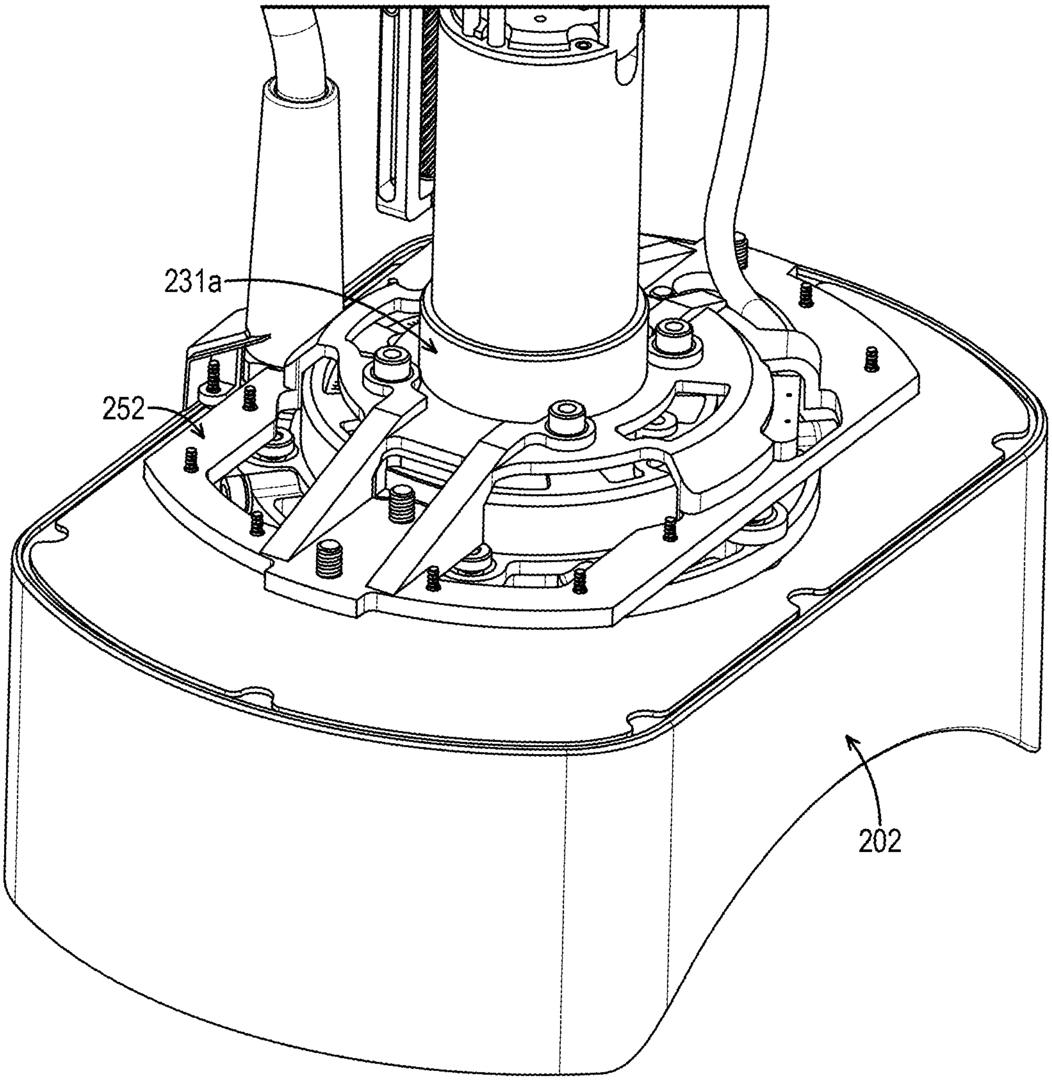
Figure 2L:
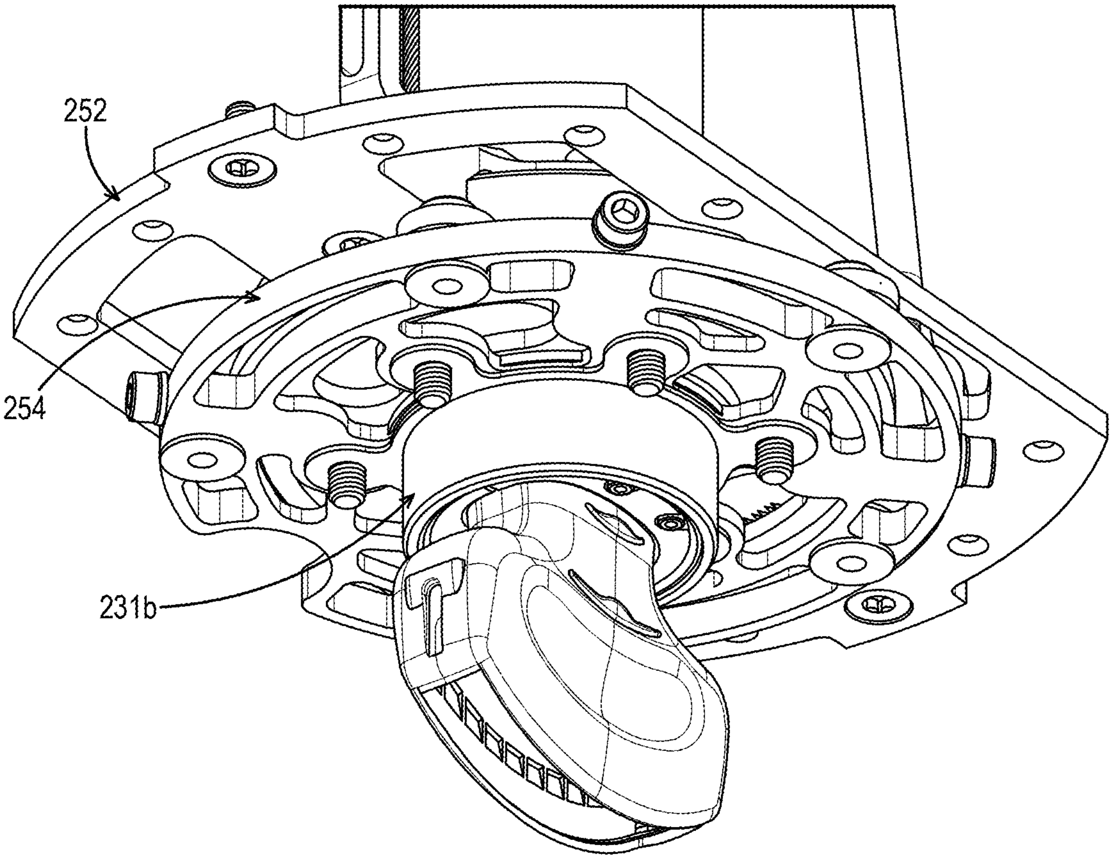
Figure 2M:
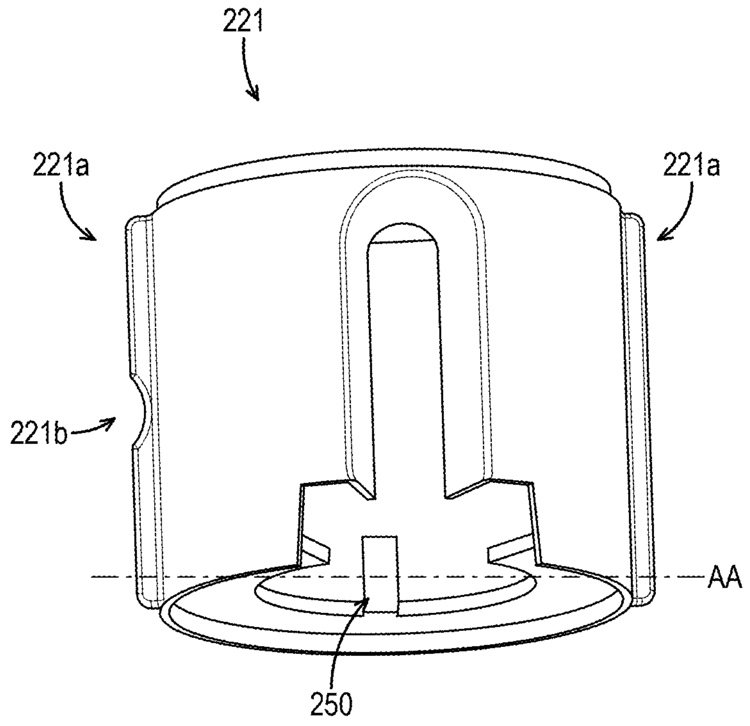
Figure 2N:
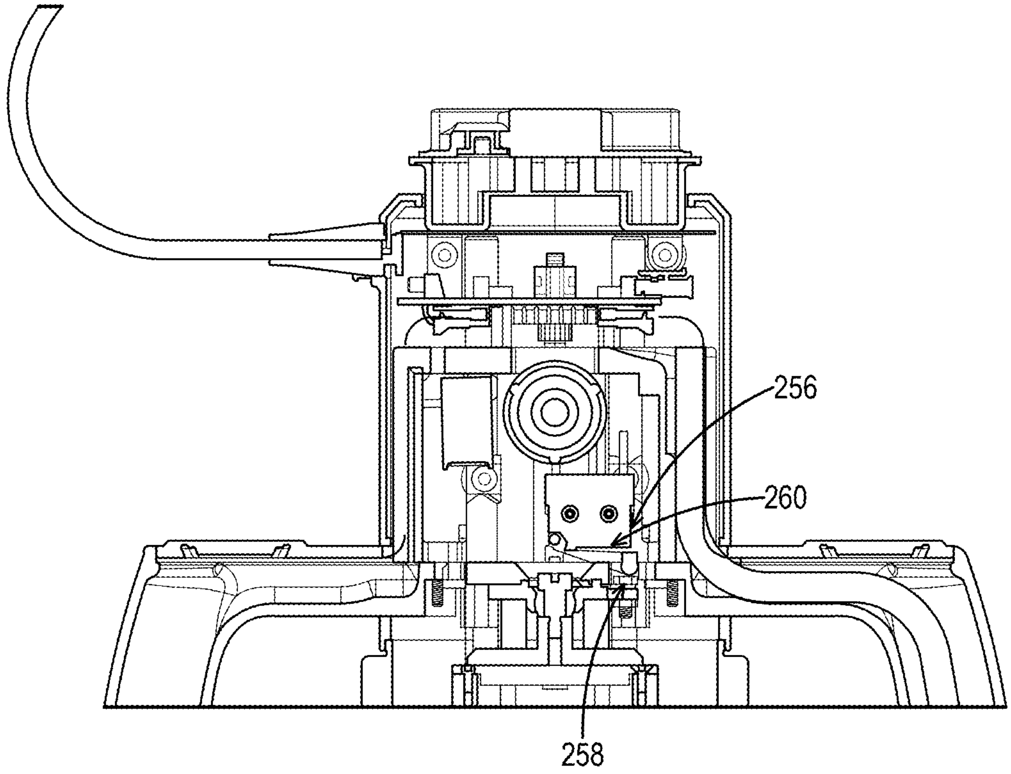

In some embodiments, referring to FIG. 2H, rotation of the ultrasound imaging probe (such as with rotation collar 221) activates detents 247 that can be located at periodic locations around the keyed plate 246 (e.g., at 0, +90 degrees and −90 degrees) to provide tactile feedback at specified rotation angles to the user.

Some embodiments can include one or more free drive membrane switches that are connected into the PCB and provide a digital output when pressed/activated. There can be at least one button on each of two handles on the treatment head. The PCB can then be designed in such a way that either of these buttons being pressed will send a digital signal to the robotic positioning system to activate free drive.

In terms of outputs, a Lumberg cable can be used as a connector out from the PCB that connects the PCB to the robot I/O. Through this connection, all electronic components are powered and there are 2 analog outputs (linear and rotation encoders) to the robot and 2 digital outputs (limit switch and free drive buttons).

FIG. 2D is a cross-sectional view of the treatment head including showing the shaft or handle 228 of the imaging probe and the coupling assembly 230 of the treatment head, in addition to the various other features previously described above including imaging probe control 212, PCBs 224, encoder(s) 227. Additionally, FIG. 2D shows linear motion coupler 229 which is a platform configured to translate axial movement of the mechanical linkage associated with the imaging probe control to the coupling assembly 230 to allow for axial movement of the imaging probe. Further details are provided herein with respect to FIG. 2E.

One or more bushings 231 can be positioned near a base of the handle(s) to provide a precise fit between the coupling assembly 230 and the bore of the treatment head. The bushing(s) can be configured to align an outer diameter of the coupling assembly with an inner diameter of the bore of the treatment head. The tight tolerances afforded by the bushings between the coupling assembly and the bore ensure a precise fit between the coupling assembly and the bore so that the imaging probe can track axially along the bore without any lateral movement, ensuring that the focus direction of the transducer array remains consistent.

Figure 2O:
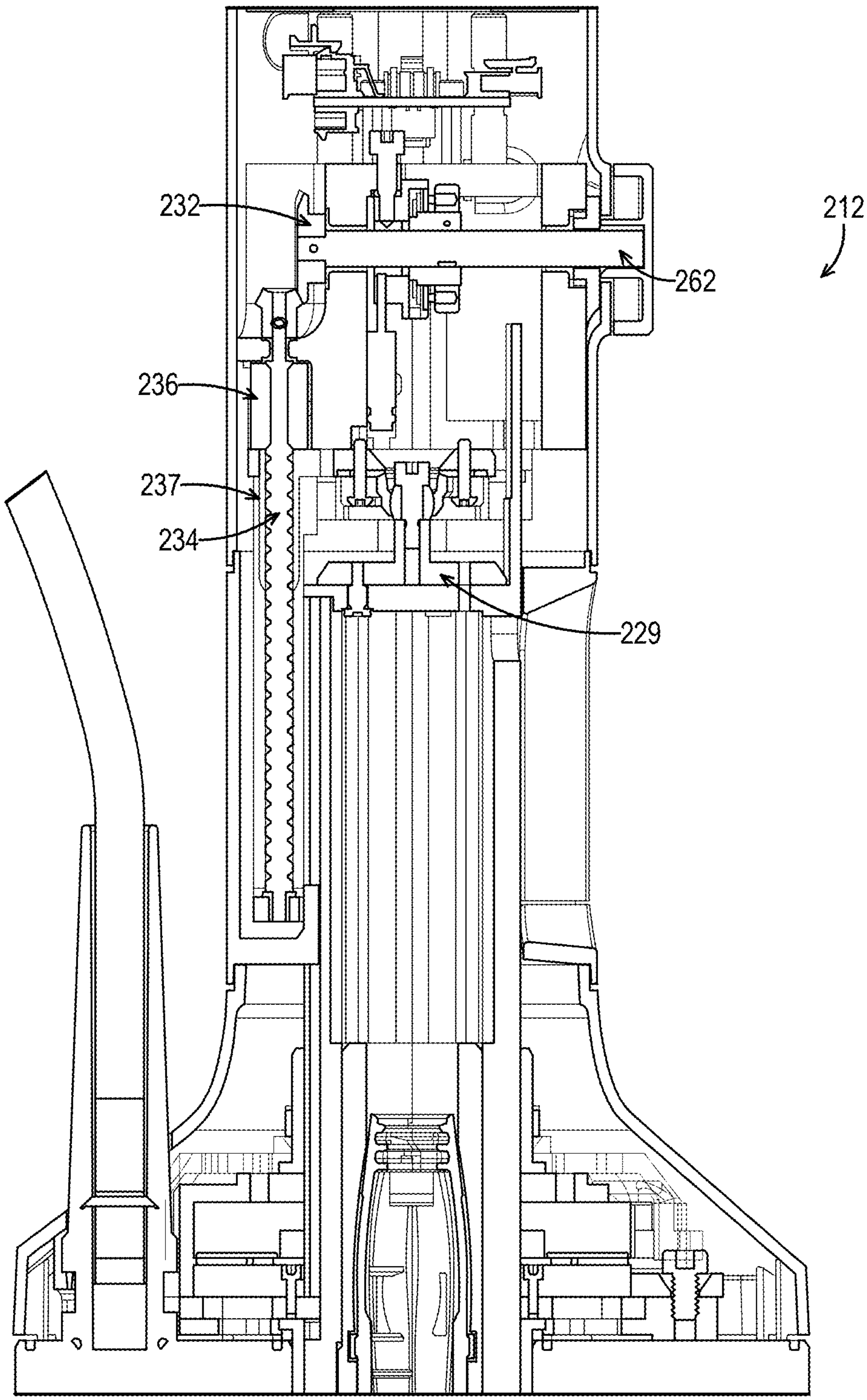
Figure 2P:
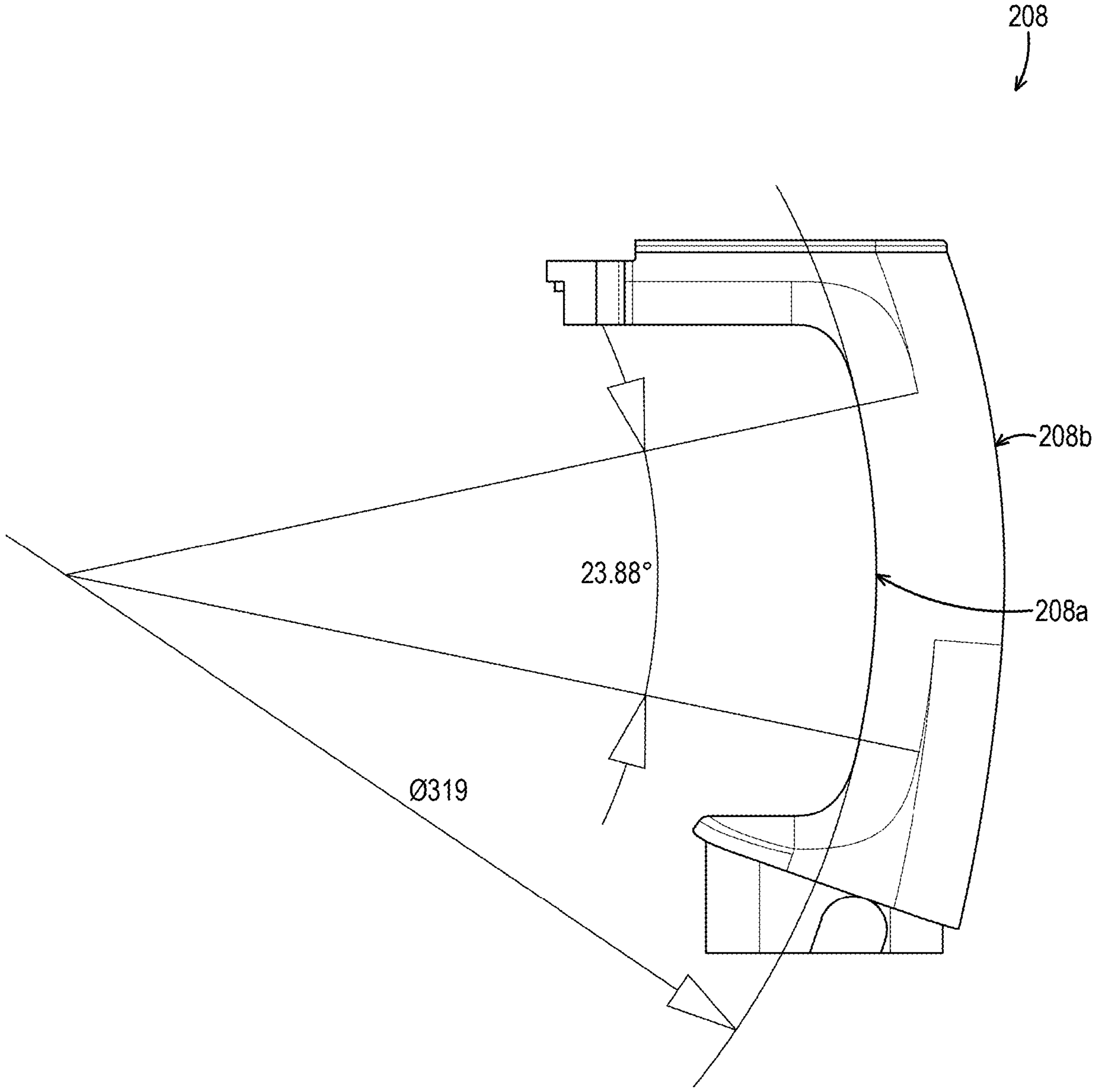

FIGS. 2E and 2O shows a mechanical implementation of the imaging probe control 212. In this embodiment, the imaging probe control 212 can include a shaft (e.g., shaft 262 in FIG. 2O) that is coupled or connected to a gear 232. Rotation of the imaging probe control 212 and shaft results in rotation of the gear 232, which engages with a geared shaft 234. The geared shaft (linear screw) 234 can be threaded and configured to engage with corresponding threading on a shuttle assembly 236. Rotation of the geared shaft 234 can cause the shuttle assembly 236 to move axially along the geared shaft. In some examples, the shuttle assembly can include extension arms 237 which can include protrusions or rods 239 configured to travel along a track 241. The rods 239 and track 241 can ensure smooth and consistent axial movement of the shuttle assembly when the imaging probe is translated. While the shuttle assembly and extension arms are shown as two separate components which are linked together, in this example, it should be understood that other embodiments may comprise a single piece shuttle assembly integral with the extension arms and rods. The linear motion coupler 229 can be fixedly attached to the shuttle assembly. With this configuration, rotation of the imaging probe control 212 can therefore cause axial advancement of the shuttle assembly, linear motion coupler, and therefore, imaging probe. The imaging probe is attached via inserts that fit tightly around the probe handle geometry to a tube that translates through the center bore of the therapy transducer. This tube is attached at the top to the linear motion coupler that is comprised of a tube cap and float plate. The float plate is attached to the tube cap in such a way that a small amount of motion is allowed horizontally between the tube cap and the shuttle assembly while maintaining a tight connection axially between the two. This allows for the bottom (tube and imaging probe) assembly in the translation stack to not be confined by alignment and tolerances of components above but maintain vertical alignment with the transducer bore given that small horizontal space to move as needed to translate freely.

While FIG. 2E provides the mechanical/manual implementation of axial and rotational movement of the imaging probe, it can be understood how the treatment head could be modified to provide automated or electronic control of the imaging probe. For example, a first motor could be coupled to gear 232 via a shaft, and rotation of the imaging probe control 212 could be used to control the rotation of the motor, and therefore the gear 232, which then translates rotational motion into linear motion by moving the shuttle assembly along geared shaft 234. A similar arrangement could be implemented for rotation by coupling a second motor to a second geared shaft that runs along the center of the coupling assembly and couples either directly to the probe handle or to another rigid feature of the coupling assembly. In this manner, rotation of the imaging probe control (or another knob or control) could result in rotation of the second shaft, and therefore rotation of the imaging probe.

Manual rotation of the imaging probe may be controlled with rotation sleeve 221, as illustrated in at least FIGS. 2A, 2F, and in more detail in FIG. 2J. Referring to FIG. 2F the coupling assembly 230 can include a slot, rail, groove, or other engagement feature 234 configured to engage with a corresponding engagement feature or key in the rotation sleeve (e.g., rotation sleeve 221 in FIG. 2A). For rotation of the imaging probe, the slot of the coupling assembly is keyed to the rotation sleeve 221 that the user can rotate +/−90 or +/−180 degrees. The slot 234 can run along the vertical length of the coupling assembly so that the imaging probe can be rotated anywhere along the translation of the probe.

Referring to FIG. 2J, it is shown how the slot 234 interacts with key 250 on the rotation sleeve 221.

FIGS. 2K and 2L additionally show how bushings 231*a* and 231*b* (which maintain tight clearances with the coupling assembly 230), are secured with or surrounded by grip base 252 and adapter plate 254, respectively. Additionally, the grip base 252 can couple to the therapy transducer array 202, as shown.

Referring to FIG. 2M, rotation sleeve 221 further includes tab(s) 221*a* disposed along an exterior portion of the sleeve 221. The tabs 221*a* can be, for example, disposed 180 degrees apart on the rotation sleeve. The tabs 221*a* can be manipulated by the user for sleeve rotation as well as providing the user with a visual indicator of probe orientation on the treatment head. The tabs 221*a* can be configured to align with the orientation of the ultrasound imaging probe. In some embodiments, a horizontal axis AA of the imaging probe head can pass through the tabs 221*a*. In some examples, one or more notch feature(s) 221*b* may be disposed on at least one of the tabs 221*a*. The notch feature(s) 221*b* may be used to indicate to the user not to submerge the treatment head in the coupling medium, past or above this notch feature(s) 221*b* to protect linear positional encoder accuracy.

In another representative example of a design for a treatment head with motorized probe rotation and translation, the design may comprise the following key components and mechanisms: The ultrasound imaging probe may be affixed within the coupling assembly such that the center of the imaging plane is aligned with a central axis of the coupling assembly. The therapy transducer may include (either within its own housing, or rigidly attached to it), a cylindrical bore whose axis is aligned with the therapy beam axis. The inner diameter of this bore may be configured to match (within a slip tolerance) the outer diameter of coupling assembly. This results in a shared axis of imaging and therapy, with alignment between the imaging axis and therapy axis maintained through both degrees of freedom of the cylindrical mating (rotation of the imager about that axis, and translation of the imager along that axis). The relative motion between these two components can be accomplished via electric motors. A motor to move the imager along the rotational degree of freedom may be coupled to the imager tube directly, or independently from translational motion by coupling rotation via an axially keyed or splined shaft. A motor to move the imager along the translational degree of freedom may be coupled to the imager tube directly, or independently from rotational motion by coupling translation via a circumferentially keyed shaft. If both motors are to be stationary (easier for wiring), one of the axes must be coupled independently from the other.

To provide feedback on the position of the imager, several possibilities exist. The simplest form is a single position sensor. This can be a mechanical switch or other contact/non-contact sensor that changes signal when the imager reaches a position of interest along one of the degrees of freedom. In more detail, the imaging probe position may be read by a position sensor, home switch, or contact switch 256 as illustrated in FIG. 2N. When the imaging probe is in an unextended position, the imaging probe is fully retracted, towards the transducer, in the home position. In one embodiment, and as illustrated in FIG. 2N, when the imaging probe is fully retracted, a set screw 258 will come into contact with a lever 260 and initiate a binary on/off signal from the home switch. The home position of the imaging probe is conveyed to the user and robot through a digital output triggered at the switch. When the imaging probe is unextended or retracted, the imaging probe is outside of the therapy path such that any histotripsy pulses will not pass through the ultrasound probe. When the imaging probe is extended for patient viewing and planning, the home switch lever will be released and the signal will turn to "off". The UI can display the imaging probe translation or extension, and rotation to the user. In embodiments, patient treatment cannot occur until the home switch has detected the imaging probe in fully or partially retracted such that the imaging probe is out of the transducer histotripsy pulses. For example, an electronic controller or processor of the system can be configured to prevent the initiation of histotripsy therapy unless the ultrasound imaging probe is retracted to a specified position (e.g., fully retracted, partially retracted, or retracted enough to not block or interfere with histotripsy pulses from the therapy transducer array). While the illustrated embodiment provides a physical switch to determine if the ultrasound imaging probe is retracted, other embodiments are also provided, including sensors that don't require a physical contact or connection. For example, laser, infrared (IR), or other similar sensors can be used to determine the axial position of the imaging probe and/or whether the imaging probe is retracted, extended, or in a position where it does not obstruct or substantially obstruct the therapy transducer elements of the therapy array.

Details related to mechanical coupling strategies can influence which strategy might be preferred. For example, measuring at the motor shaft is typically easiest as many motors include encoders, but any mechanical slip, flex, or backlash would result in inaccuracy of the reading relative to the true position of the imager. Motors may also require an appropriate controller to accomplish precise positioning. These controllers can be local to minimize the wiring/connections at the treatment head. These motor controllers are also typically controlled by a master coordinated motion controller. This master controller would then handle all communication with the System via a single communication channel, and coordinate and control all local motors, controllers, sensors, encoders, etc. The master controller may be integral to the treatment head itself, or configured/integrated into another sub-system of the overall histotripsy system, and with communication being provided through or in parallel to the robot IO, or other IO interfaces of the system.

In another example treatment head design, the manual and/or motorized rotating and translating probe treatment head may be used to execute controlled robotically-enabled ultrasound sweeps to enable the registration of tracked ultrasound data and multi-modal image registration of the live streaming ultrasound with a set of reference images, including but not limited to, MRI, CT, PET/CT, ultrasound, and/or other modalities. The sweep and related data may be used to construct, deform, register and augment 2D multi-planar data into deformable 3D models. The system and supporting software may also be enabled to display treatment plan contours within these data sets (2D, 3D and various overlays and views), and in terms of treatment planning and treatment parameters, the system may be configured to automatically populate a grid array of focal locations (e.g., bubble cloud locations) of various size, number, spacing, etc., as well as embedded logic/control over selected sequence and therapy parameters by focal location, and by application/indication, etc.

FIG. 2F provides a view of the imaging probe 204, including a probe shaft 228 and a coupling assembly 230. As shown, the handle or shaft 228 of a typical ultrasound imaging probe is much shorter than needed for the present application, so the coupling assembly 230 can be sized and configured to fit over the probe shaft or handle, and to extend from the treatment head bore to the linear motion coupler to provide the proper spacing between the treatment head handles/controls and the treatment head bore. The coupling assembly 230 can be affixed to the probe with screws 232, for example. Additionally, referring to FIG. 2F, the coupling assembly 230 can include a slot, rail, groove, or other engagement feature 234 configured to engage with a corresponding engagement feature in the rotation sleeve (e.g., rotation sleeve 221 in FIG. 2A). For rotation of the imaging probe, the slot of the coupling assembly is keyed to the rotation sleeve that the user can rotate +/−90 or +/−180 degrees. The slot can run along the vertical length of the coupling assembly so that the imaging probe can be rotated anywhere along the translation of the probe. In some embodiments, the coupling assembly and/or the linear motion coupler (e.g., linear motion coupler 229 in FIG. 2D) activates detents that are located at 0, +90 degrees and −90 degrees to provide tactile feedback at specified rotation angles to the user.

As the treatment head is frequently used within a coupling medium, specific components of the treatment head are required to be waterproof and not absorb the liquid coupling medium. In particular, the probe shaft 228 should not change in dimension(s) when in a use environment. As the ultrasound probe will translate and rotate within the probe shaft 228, the probe shaft 228 should be water resistant. The probe shaft is comprised of aluminum. Other components of the coupling assembly may also be provided waterproof, or water-resistant.

In some examples, axial translation of the imaging probe position enables the ability to modify a relative position of the therapy transducer array independent of the imaging probe position (e.g., the imaging probe remains in a fixed z-position on/near the skin as the therapy transducer executes its respective treatment and motion pattern/pathway).

The ultrasound imaging probe of the treatment head may comprise or be configured based on clinical application/use case (for visualizing the general target location, surrounding anatomy and critical structures/adjacent organs and/or target motion relative to such, bubble cloud during calibration, test pulses, automated treatment and post-treatment verification, etc.). As described, imaging probe mechanical/electrical support for encoded probe rotation and translation capabilities, to allow multiple (including orthogonal) imaging views/perspectives via rotation, as well as the ability to view on/near the skin independent to therapy transducer location via translation.

The histotripsy therapy transducer array may comprise various designs/geometries optimized for/by specific application and use requirements (abdominal targets, versus prostate, versus more superficial targets such as breast/thyroid, etc.). In some embodiments, the therapy transducer array may include various mechanical support features for interfacing/building up the proximal side of the treatment head, including support for an embedded coaxial imaging probe in a central bore, and mechanical mounting locations for internal components, treatment head handles, housings, etc. The therapy transducers may also be uniquely electronically keyed to allow variant/application specific use and recognition by the system software (e.g., a liver or abdominal treatment head, versus prostate, thyroid or breast, etc.).

Since the treatment head provides the ability to adjust the focus and rotational orientation of the imaging probe with respect to the therapy transducer array, new and novel functionality and treatment is enabled. For example, advancing or retracting the ultrasound imaging probe relative to the therapy transducer array enables the system to image tissue outside of a target tissue volume (e.g., at greater depth), or image very large target tissue volumes without having to move the therapy transducer array. Additionally, the ultrasound imaging probe can be moved closer to the target tissue volume to increase resolution and/or imaging quality, while the therapy transducer array can be maintained at a significant standoff from the body. Furthermore, the ability to rotate the ultrasound imaging probe relative to the therapy transducer provides additional slices or views of the tissue being imaged.

Figure 3A:
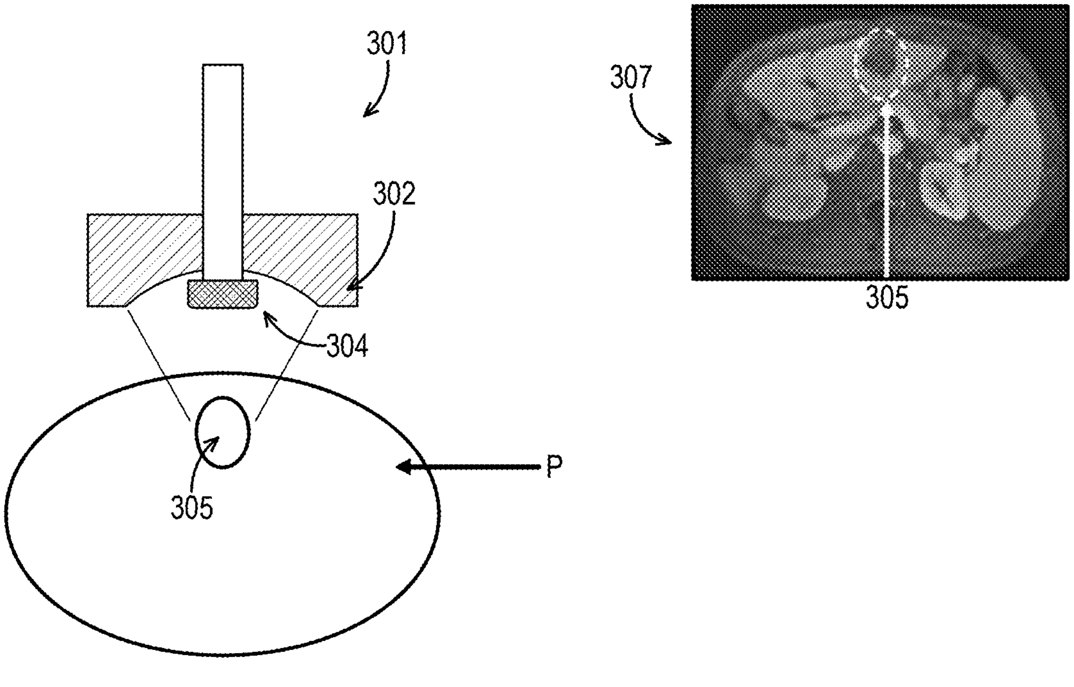
FIGS. 3A-3D illustrate axial movement of an ultrasound imaging probe relative to a therapy transducer and additionally movement of the therapy transducer while contacting the patient with the ultrasound imaging probe.

FIG. 3A illustrates one example of a treatment head 301 of a histotripsy therapy system positioned adjacent to a patient P having a therapy transducer array 302 and an imaging probe 304. While it should be understood that a coupling container and ultrasound coupling medium would be used to acoustically couple the treatment head to the patient, the coupling container is not shown for ease of illustration. The therapy transducer array 302 can have a focus positioned within a target treatment volume 305. Real-time ultrasound images from the imaging probe 304 can be displayed on display 307. In the example shown, the target treatment volume 305 can be graphically overlaid upon the real-time ultrasound images. In the example of FIG. 3A, both the imaging probe 304 and the therapy transducer array are positioned away from the skin of the patient. The resulting images from the imaging probe as a result of having to travel through the acoustic coupling medium can include increased noise and/or lower resolution compared to positioning the probe directly on the skin. Alternatively, if a coupling container is used to acoustically couple the treatment head to the patient, the imaging probe can be placed in contact with the coupling container, or a membrane of the coupling container, which itself can be in contact with the skin (or separated by a layer of acoustic coupling medium).

Figure 3B:
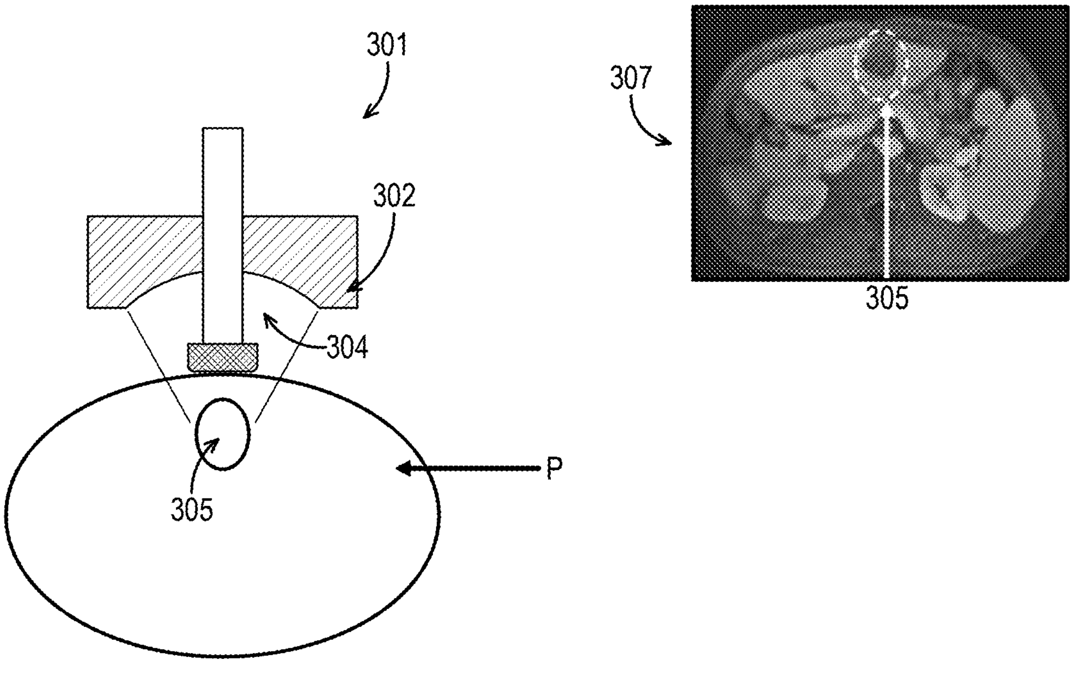

Referring to FIG. 3B, axial translation of the imaging probe 304 allows for the probe to be placed in contact with the skin of the patient to improve the resolution of images, reduce noise, and/or image at a greater depth than when the probe is fully retracted (as in FIG. 3A). It should be noted that while the imaging probe is translated toward the patient, the focal point and target treatment volume 305 (as displayed on display 307) remains in the same location.

Figure 3C:
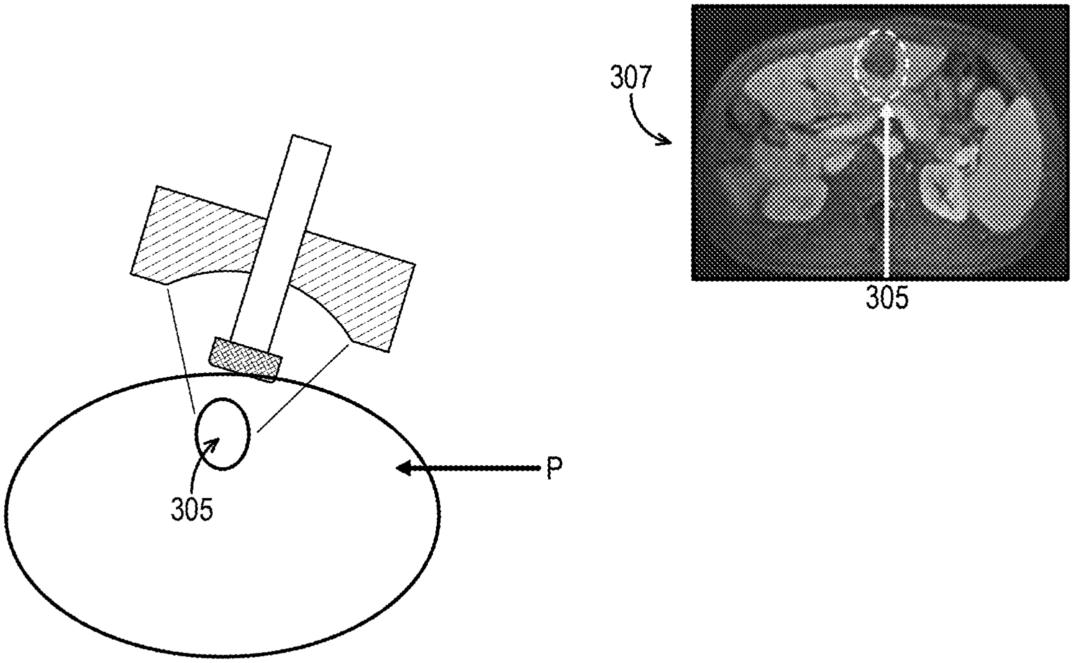
Figure 3D:
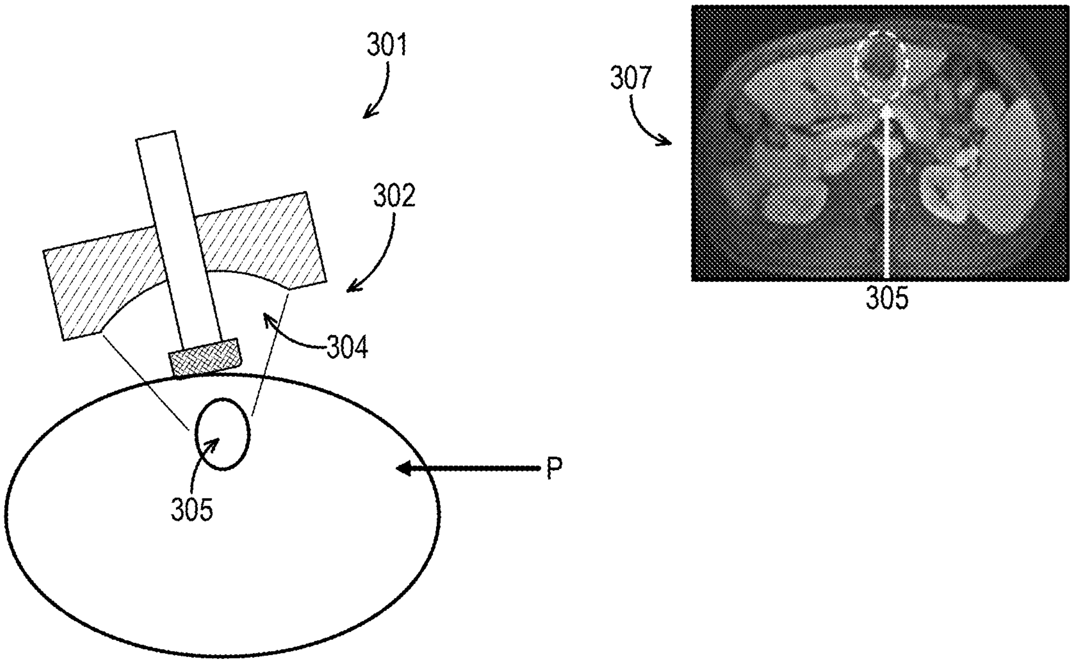

Referring to FIGS. 3C-3D, this allows for relative movement and/or rotation of the treatment head 301 while maintaining the probe in contact with the patient's skin to scan the target tissue volume and beyond.

Robotics

They system may comprise various Robotic sub-systems and components, including but not limited to, one or more robotic arms and controllers, which may further work with other sub-systems or components of the system to deliver and monitor acoustic cavitation/histotripsy. As previously discussed herein, robotic arms and control systems may be integrated into one or more Cart configurations.

For example, one system embodiment may comprise a Cart with an integrated robotic arm and control system, and Therapy, Integrated Imaging and Software, where the robotic arm and other listed sub-systems are controlled by the user through the form factor of a single bedside Cart.

In other embodiments, the Robotic sub-system may be configured in one or more separate Carts, that may be a driven in a master/slave configuration from a separate master or Cart, wherein the robotically-enabled Cart is positioned bed/patient-side, and the Master is at a distance from said Cart.

Disclosed robotic arms may be comprised of a plurality of joints, segments, and degrees of freedom and may also include various integrated sensor types and encoders, implemented for various use and safety features. Sensing technologies and data may comprise, as an example, vision, potentiometers, position/localization, kinematics, force, torque, speed, acceleration, dynamic loading, and/or others. In some cases, sensors may be used for users to direct robot commands (e.g., hand gesture the robot into a preferred set up position, or to dock home). Additional details on robotic arms can be found in US Patent Pub. No. 2013/0255426 to Kassow et al. which is disclosed herein by reference in its entirety.

The robotic arm receives control signals and commands from the robotic control system, which may be housed in a Cart. The system may be configured to provide various functionalities, including but not limited to, position, tracking, patterns, triggering, and events/actions.

Position may be configured to comprise fixed positions, pallet positions, time-controlled positions, distance-controlled positions, variable-time controlled positions, variable-distance controlled positions.

Tracking may be configured to comprise time-controlled tracking and/or distance-controlled tracking.

The patterns of movement may be configured to comprise intermediate positions or waypoints, as well as sequence of positions, through a defined path in space.

Triggers may be configured to comprise distance measuring means, time, and/or various sensor means including those disclosed herein, and not limited to, visual/imaging-based, force, torque, localization, energy/power feedback and/or others.

Events/actions may be configured to comprise various examples, including proximity-based (approaching/departing a target object), activation or de-activation of various end-effectors (e.g., therapy transducers), starting/stopping/pausing sequences of said events, triggering or switching between triggers of events/actions, initiating patterns of movement and changing/toggling between patterns of movement, and/or time-based and temporal over the defined work and time-space.

In one embodiment, the system comprises a three degree of freedom robotic positioning system, enabled to allow the user (through the software of the system and related user interfaces), to micro-position a therapy transducer through X, Y, and Z coordinate system, and where gross macro-positioning of the transducer (e.g., aligning the transducer on the patient's body) is completed manually. In some embodiments, the robot may comprise 6 degrees of freedom including X, Y, Z, and pitch, roll and yaw. In other embodiments, the Robotic sub-system may comprise further degrees of freedom, that allow the robot arm supporting base to be positioned along a linear axis running parallel to the general direction of the patient surface, and/or the supporting base height to be adjusted up or down, allowing the position of the robotic arm to be modified relative to the patient, patient surface, Cart, Coupling sub-system, additional robots/robotic arms and/or additional surgical systems, including but not limited to, surgical towers, imaging systems, endoscopic/laparoscopic systems, and/or other.

One or more robotic arms may also comprise various features to assist in maneuvering and modifying the arm position, manually or semi-manually, and of which said features may interface on or between the therapy transducer and the most distal joint of the robotic arm. In some embodiments, the feature is configured to comprise a handle allowing maneuvering and manual control with one or more hands. The handle may also be configured to include user input and electronic control features of the robotic arm, to command various drive capabilities or modes, to actuate the robot to assist in gross or fine positioning of the arm (e.g., activating or deactivating free drive mode). The work-flow for the initial positioning of the robotic arm and therapy head can be configured to allow either first positioning the therapy transducer/head in the coupling solution, with the therapy transducer directly interfaced to the arm, or in a different work-flow, allowing the user to set up the coupling solution first, and enabling the robot arm to be interfaced to the therapy transducer/coupling solution as a later/terminal set up step.

In some embodiments, the robotic arm may comprise a robotic arm on a laparoscopic, single port, endoscopic, hybrid or combination of, and/or other robot, wherein said robot of the system may be a slave to a master that controls said arm, as well as potentially a plurality of other arms, equipped to concurrently execute other tasks (vision, imaging, grasping, cutting, ligating, sealing, closing, stapling, ablating, suturing, marking, etc.), including actuating one or more laparoscopic arms (and instruments) and various histotripsy system components. For example, a laparoscopic robot may be utilized to prepare the surgical site, including manipulating organ position to provide more ideal acoustic access and further stabilizing said organ in some cases to minimize respiratory motion. In conjunction and parallel to this, a second robotic arm may be used to deliver non-invasive acoustic cavitation through a body cavity, as observed under real-time imaging from the therapy transducer (e.g., ultrasound) and with concurrent visualization via a laparoscopic camera. In other related aspects, a similar approach may be utilized with a combination of an endoscopic and non-invasive approach, and further, with a combination of an endoscopic, laparoscopic and non-invasive approach.

Software

The system may comprise various software applications, features and components which allow the user to interact, control and use the system for a plethora of clinical applications. The Software may communicate and work with one or more of the sub-systems, including but not limited to Therapy, Integrated Imaging, Robotics and Other Components, Ancillaries and Accessories of the system.

Overall, in no specific order of importance, the software may provide features and support to initialize and set up the system, service the system, communicate and import/export/store data, modify/manipulate/configure/control/command various settings and parameters by the user, mitigate safety and use-related risks, plan procedures, provide support to various configurations of transducers, robotic arms and drive systems, function generators and amplifier circuits/slaves, test and treatment ultrasound sequences, transducer steering and positioning (electromechanical and electronic beam steering, etc.), treatment patterns, support for imaging and imaging probes, manual and electromechanical/robotically-enabling movement of, imaging support for measuring/characterizing various dimensions within or around procedure and treatment sites (e.g., depth from one anatomical location to another, etc., pre-treatment assessments and protocols for measuring/characterizing in situ treatment site properties and conditions (e.g., acoustic cavitation/histotripsy thresholds and heterogeneity of), targeting and target alignment, calibration, marking/annotating, localizing/navigating, registering, guiding, providing and guiding through work-flows, procedure steps, executing treatment plans and protocols autonomously, autonomously and while under direct observation and viewing with real-time imaging as displayed through the software, including various views and viewports for viewing, communication tools (video, audio, sharing, etc.), troubleshooting, providing directions, warnings, alerts, and/or allowing communication through various networking devices and protocols. It is further envisioned that the software user interfaces and supporting displays may comprise various buttons, commands, icons, graphics, text, etc., that allow the user to interact with the system in a user-friendly and effective manner, and these may be presented in an unlimited number of permutations, layouts and designs, and displayed in similar or different manners or feature sets for systems that may comprise more than one display (e.g., touch screen monitor and touch pad), and/or may network to one or more external displays or systems (e.g., another robot, navigation system, system tower, console, monitor, touch display, mobile device, tablet, etc.).

The software, as a part of a representative system, including one or more computer processors, may support the various aforementioned function generators (e.g., FPGA), amplifiers, power supplies and therapy transducers. The software may be configured to allow users to select, determine and monitor various parameters and settings for acoustic cavitation/histotripsy, and upon observing/receiving feedback on performance and conditions, may allow the user to stop/start/modify said parameters and settings.

The software may be configured to allow users to select from a list or menu of multiple transducers and support the auto-detection of said transducers upon connection to the system (and verification of the appropriate sequence and parameter settings based on selected application). In other embodiments, the software may update the targeting and amplifier settings (e.g., channels) based on the specific transducer selection. The software may also provide transducer recommendations based on pre-treatment and planning inputs. Conversely, the software may provide error messages or warnings to the user if said therapy transducer, amplifier and/or function generator selections or parameters are erroneous, yield a fault or failure. This may further comprise reporting the details and location of such.

In addition to above, the software may be configured to allow users to select treatment sequences and protocols from a list or menu, and to store selected and/or previous selected sequences and protocols as associated with specific clinical uses or patient profiles. Related profiles may comprise any associated patient, procedure, clinical and/or engineering data, and maybe used to inform, modify and/or guide current or future treatments or procedures/interventions, whether as decision support or an active part of a procedure itself (e.g., using serial data sets to build and guide new treatments).

As a part of planning or during the treatment, the software (and in working with other components of the system) may allow the user to evaluate and test acoustic cavitation/histotripsy thresholds at various locations in a user-selected region of interest or defined treatment area/volume, to determine the minimum cavitation thresholds throughout said region or area/volume, to ensure treatment parameters are optimized to achieve, maintain and dynamically control acoustic cavitation/histotripsy. In one embodiment, the system allows a user to manually evaluate and test threshold parameters at various points. Said points may include those at defined boundary, interior to the boundary and center locations/positions, of the selected region of interest and treatment area/volume, and where resulting threshold measurements may be reported/displayed to the user, as well as utilized to update therapy parameters before treatment. In another embodiment, the system may be configured to allow automated threshold measurements and updates, as enabled by the aforementioned Robotics sub-system, wherein the user may direct the robot, or the robot may be commanded to execute the measurements autonomously.

Software may also be configured, by working with computer processors and one or more function generators, amplifiers and therapy transducers, to allow various permutations of delivering and positioning optimized acoustic cavitation/histotripsy in and through a selected area/volume. This may include, but not limited to, systems configured with a fixed/natural focus arrangement using purely electromechanical positioning configuration(s), electronic beam steering (with or without electromechanical positioning), electronic beam steering to a new selected fixed focus with further electromechanical positioning, axial (Z axis) electronic beam steering with lateral (X and Y) electromechanical positioning, high speed axial electronic beam steering with lateral electromechanical positioning, high speed beam steering in 3D space, various combinations of including with dynamically varying one or more acoustic cavitation/histotripsy parameters based on the aforementioned ability to update treatment parameters based on threshold measurements (e.g., dynamically adjusting amplitude across the treatment area/volume).

Other Components, Ancillaries and Accessories

The system may comprise various other components, ancillaries and accessories, including but not limited to computers, computer processors, power supplies including high voltage power supplies, controllers, cables, connectors, networking devices, software applications for security, communication, integration into information systems including hospital information systems, cellular communication devices and modems, handheld wired or wireless controllers, goggles or glasses for advanced visualization, augmented or virtual reality applications, cameras, sensors, tablets, smart devices, phones, internet of things enabling capabilities, specialized use “apps” or user training materials and applications (software or paper based), virtual proctors or trainers and/or other enabling features, devices, systems or applications, and/or methods of using the above.

Treatment Head Methods/Applications and Examples

In addition to performing a breadth of procedures, the system may allow additional benefits, such as enhanced planning, imaging and guidance to assist the user. In one embodiment, the system may allow a user to create a patient, target and application specific treatment plan, wherein the system may be configured to optimize treatment parameters based on feedback to the system during planning, and where planning may further comprise the ability to run various test protocols to gather specific inputs to the system and plan.

Feedback may include various energy, power, location, position, tissue and/or other parameters.

The system, and the above feedback, may also be further configured and used to autonomously (and robotically) execute the delivery of the optimized treatment plan and protocol, as visualized under real-time imaging during the procedure, allowing the user to directly observe the local treatment tissue effect, as it progresses through treatment, and start/stop/modify treatment at their discretion. Both test and treatment protocols may be updated over the course of the procedure at the direction of the user, or in some embodiments, based on logic embedded within the system.

It is also recognized that many of these benefits may further improve other forms of acoustic therapy, including thermal ablation with high intensity focused ultrasound (HIFU), high intensity therapeutic ultrasound (HITU) including boiling histotripsy (thermal cavitation), and are considered as part of this disclosure. The disclosure also considers the application of histotripsy as a means to activate previously delivered in active drug payloads whose activity is inert due to protection in a micelle, nanostructure or similar protective structure or through molecular arrangement that allows activation only when struck with acoustic energy.

In another aspect, the Therapy sub-system, comprising in part, one or more amplifiers, transducers and power supplies, may be configured to allow multiple acoustic cavitation and histotripsy driving capabilities, affording specific benefits based on application, method and/or patient specific use. These benefits may include, but are not limited to, the ability to better optimize and control treatment parameters, which may allow delivery of more energy, with more desirable thermal profiles, increased treatment speed and reduced procedure times, enable electronic beam steering and/or other features.

This disclosure also includes novel systems and concepts as related to systems and sub-systems comprising new and “universal” amplifiers, which may allow multiple driving approaches (e.g., single and multi-cycle pulsing). In some embodiments, this may include various novel features to further protect the system and user, in terms of electrical safety or other hazards (e.g., damage to transducer and/or amplifier circuitry).

In another aspect, the system, and Therapy sub-system, may include a plethora of therapy transducers, where said therapy transducers are configured for specific applications and uses and may accommodate treating over a wide range of working parameters (target size, depth, location, etc.) and may comprise a wide range of working specifications (detailed below). Transducers may further adapt, interface and connect to a robotically-enabled system, as well as the Coupling sub-system, allowing the transducer to be positioned within, or along with, an acoustic coupling device allowing, in many embodiments, concurrent imaging and histotripsy treatments through an acceptable acoustic window. The therapy transducer may also comprise an integrated imaging probe or localization sensors, capable of displaying and determining transducer position within the treatment site and affording a direct field of view (or representation of) the treatment site, and as the acoustic cavitation/histotripsy tissue effect and bubble cloud may or may not change in appearance and intensity, throughout the treatment, and as a function of its location within said treatment (e.g., tumor, healthy tissue surrounding, critical structures, adipose tissue, etc.).

The systems, methods and use of the system disclosed herein, may be beneficial to overcoming significant unmet needs in the areas of soft tissue ablation, oncology, immuno-oncology, advanced image guided procedures, surgical procedures including but not limited to open, laparoscopic, single incision, natural orifice, endoscopic, non-invasive, various combination of, various interventional spaces for catheter-based procedures of the vascular, cardiovascular pulmonary and/or neurocranial-related spaces, cosmetics/aesthetics, metabolic (e.g., type 2 diabetes), plastic and reconstructive, ocular and ophthalmology, orthopedic, gynecology and men’s health, and other systems, devices and methods of treating diseased, injured, undesired, or healthy tissues, organs or cells.

Systems and methods are also provided for improving treatment patterns within tissue that can reduce treatment time, improve efficacy, and reduce the amount of energy and prefocal tissue heating delivered to patients.

Methods and use of the treatment head including the translatable/rotatable imaging probe are also provided herein.

Figure 4:
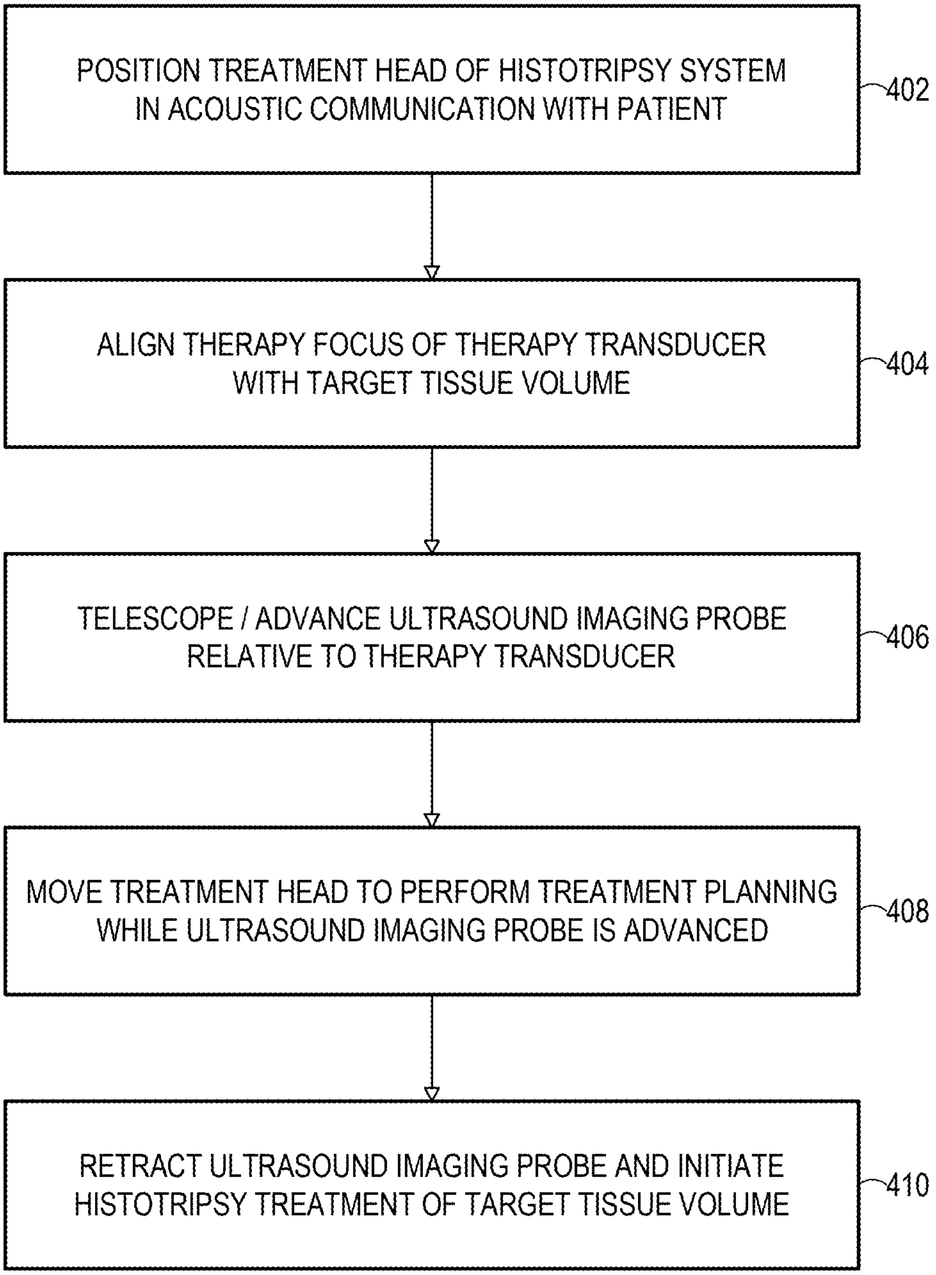
FIG. 4 is a flowchart describing methods of using a treatment head according to the present disclosure.

For example, referring to FIG. 4, a flowchart is illustrated that describes a method of using the treatment head described above. Referring to step 402, the treatment head of the histotripsy system can be positioned in acoustic communication with the patient. For example, the treatment head can be mounted to a robotic positioning system and manipulated or guided (manually or automatically) into a coupling container configured to acoustically couple the treatment head to the patient's skin.

Next, at step 404, the therapy focus of the therapy transducer can be aligned with the target tissue volume to be treated. In some embodiments, the focal distance of the therapy transducer is known and fixed, so the robotic positioning system can position the therapy transducer from the target tissue volume by that known focal distance.

At step 406, the ultrasound imaging probe can be axially extended, advanced or telescoped towards the target tissue volume to allow for imaging and treatment planning. In some examples, the ultrasound imaging probe can be advanced to be in contact with the patient's skin, while the therapy transducer is not in contact with the patient's skin. Positioning the imaging probe closer to the target tissue volume than the therapy transducer allows for a better view of the target tissue and includes improved spatial and contrast resolution and can be used to eliminate reflection artifacts from cluttering the image.

At step 408, the method further comprises moving the treatment head to perform treatment planning while the ultrasound imaging probe is axially extended or advanced. This allows for movement of the therapy transducer to scan the tissue volume while maintaining skin contact (or a telescoped state of the probe) with the ultrasound imaging probe.

At step 410, the method can include retracting the ultrasound imaging probe to a fully retracted position and initiating histotripsy therapy. In some embodiments, a switch can be activated when the imaging probe is fully retracted to indicate to the system the position of the ultrasound imaging probe (e.g., fully retracted). In some embodiments, initiating histotripsy therapy while the ultrasound imaging probe is telescoped outwards can result in one or more of the therapy transducers being blocked by the ultrasound imaging probe. Retracting the probe still allows for real-time visualization of the target tissue volume, but eliminates any potential therapy blockage.

In some embodiments, referring to FIG. 4, the ultrasound imaging probe can be retracted back in towards the therapy transducer during the therapeutic procedure. However, in another embodiment, the imaging probe can be maintained at the telescoped position during therapy. This fixes the imager in the telescoped position for better visualization of the target tissue and histotripsy bubble cloud with respect to the treatment plan. It should be noted, however, that in this embodiment, depending on how far the probe is advanced, the imaging probe could potentially block some of the therapy transducers from delivering histotripsy pulses to the tissue. Optionally, as a hybrid to the two approaches described above, the imaging probe can be telescoped out from the therapy transducer during treatment planning, but then retracted slightly (but not fully) based on the size of the target tissue volume or treatment plan so as to not block any therapy pulses from reaching the intended target. This configuration balances improved imaging quality with a reduction in registration/blocking issues.

Examples of use are also provided:

Example 1

In a representative example, the novel treatment head system is configured to allow axially translating (e.g., telescoping) the imaging probe out to/near the skin/body for planning to afford more optimal image quality, and then directing the imaging probe into a retracted "home position" for the remainder of the procedure. When the imaging probe is in a "home position," the home switch is initiated and communicates to the robot and UI the imaging probe is in a retracted position. Histotripsy therapy can then be initiated. In this example, this would enable enhanced visualization of the target (and target location) during therapy planning, including improved spatial and contrast resolution and may be used to eliminate/reduce reflection artifacts from cluttering the image. In this example, the system software would be configured to ensure the position of the planning contours (target and margin) and associated geometries/location are accurate and may include features to enforce/watchdog over potential changes, including enforcing the probe to remain in a locked position during various phases of the procedure, as displayed/monitored via the software UI.

Example 2

In another representative example, the treatment head and probe translation feature may be used as translated or "telescoped" from the planning phase and all the way through treatment, including automated therapy. As in the previous example, this would enhance visualization during planning, but also provide enhanced real-time visualization and treatment monitoring (of the target, target tissue location and histotripsy bubble cloud) throughout the procedure. In this specific example, the histotripsy system (and therapy sub-system including the transducer, drive electronics and excitation sequence) would be further configured to have sufficient therapy head room to enable this use case. In this example, the system may be further configured to monitor/assess blockage, thermal and/or any additional therapy consideration that may impact a desired therapy outcome (or performance measure/metric). There may also be specific user guided workflow steps to ensure/minimize physical collisions with the probe in the translated position, and likewise, the treatment pattern/pathway (rectilinear columns versus radial bottom-up spirals) may be uniquely configured in non-obvious ways to afford this use case (e.g., verify locked probe positions at most extreme plan locations (bottom) to minimize collisions, etc.). In addition, other features to assist in real or perceived differences between the plan and target tissue based on speed of sound differences in media (tissue and water) between imaging probe and depth/location of the plan may be implemented to ensure users have accurate rendering of the treatment contours in space.

Example 3

In another representative example, including embodiments with motorized probe translation and rotation, the imaging probe may be translated or "telescoped" out to a maximum position per requirements of the procedure, but the allowed range of translation is determined based on user selection of the intended treatment plan size (of target and margin contours). In this example, the system is configured to provide the best possible image quality and minimal real or perceived differences between the plan and the target tissue throughout the procedure. As such, the system, and system software, may be configured to have an automated set of rules of probe position in context to user selected plans.

Example 4

Based on the above, in this representative example, the system is configured to allow probe translation by the user (manual or motorized) and probe rotation, and following determining the probe is in the desired position/location and locking it, the system, directed via software control and user input, is configured to execute an automated robotically enabled imaging sweep of the patient. The robotically enabled tracked imaging sweep may be programmed to include minimum/desired parameters, such as speed or rate, distance, degree of angulation or arc, manipulation of other degrees of freedom (roll, pitch, yaw, etc.), and/or any other sweep variable. Said sweep may be viewed in replay through the system UI, and maybe edited and/or cropped to enrich the sweep data, and following these steps, may be directed through a registration process to other reference data (CT, MRI, PET CT, contrast enhanced imaging, etc.) to generate 2D, 3D and/or 4D models (including motion models).

Example 5

In another example, the treatment head design, based on computer aided design and surface models, may be rendered (geometrically and scaling accurate) in a DICOM viewing tool, to afford users the ability to select and simulate various treatment head variants in prospective patients/cases, to help assess interactions, collisions, treatment plan sizes, shapes, locations, acoustic pathways/windows, acoustic field interactions, etc. The simulation software may also include the ability to virtually simulate the imaging probe position and image quality, using an imaging simulator algorithm. This, as an unlimited example, may be used in part to determine preferred use configuration (above examples) and/or specific treatment head selection and procedure approach, etc.

Example 6

In another example, during patient planning, a user axially translates the probe, and then rotates the probe 90 degrees for optimal visualization of a target volume. Once the user is directed through various planning screens, the patient plan is locked in and the probe is then rotated back 90 degrees and then telescoped distally to the home position. Treatment can be initiated once the robot and has detected a home position of the fully retracted probe and the user can completed associated UI screens.

Use Environments

The disclosed system, methods of use, and use of the system, may be conducted in a plethora of environments and settings, with or without various support systems such as anesthesia, including but not limited to, procedure suites, operating rooms, hybrid rooms, in and out-patient settings, ambulatory settings, imaging centers, radiology, radiation therapy, oncology, surgical and/or any medical center, as well as physician offices, mobile healthcare centers or systems, automobiles and related vehicles (e.g., van), aero and marine transportation vehicles such as planes and ships, and/or any structure capable of providing temporary procedure support (e.g., tent). In some cases, systems and/or sub-systems disclosed herein may also be provided as integrated features into other environments, for example, the direct integration of the histotripsy Therapy sub-system into a MRI scanner or patient surface/bed, wherein at a minimum the therapy generator and transducer are integral to such, and in other cases wherein the histotripsy configuration further includes a robotic positioning system, which also may be integral to a scanner or bed centered design.

Coupling

Systems may comprise a variety of Coupling sub-system embodiments, of which are enabled and configured to allow acoustic coupling to the patient to afford effective acoustic access for ultrasound visualization and acoustic cavitation/histotripsy (e.g., provide acoustic window and medium between the transducer(s) and patient, and support of). These may include different form factors of such, including open and enclosed device solutions, and some arrangements which may be configured to allow dynamic control over the acoustic medium (e.g., temperature, dissolved gas content, level of particulate filtration, sterility, volume, composition, etc.). Such dynamic control components may be directly integrated to the system (within the Cart), or may be in temporary/intermittent or continuous communication with the system, but externally situated in a separate device and/or cart.

The Coupling sub-system typically comprises, at a minimum, coupling medium (e.g., degassed water or water solutions), a reservoir/container to contain said coupling medium, and a support structure (including interfaces to other surfaces or devices). In most embodiments, the coupling medium is water, and wherein the water may be conditioned before or during the procedure (e.g., chilled, degassed, filtered, etc.). Various conditioning parameters may be employed based on the configuration of the system and its intended use/application.

The reservoir or medium container may be formed and shaped to various sizes and shapes, and to adapt/conform to the patient, allow the therapy transducer to engage/access and work within the acoustic medium, per defined and required working space (minimum volume of medium to allow the therapy transducer to be positioned and/or move through one or more treatment positions or patterns, and at various standoffs or depths from the patient, etc.), and wherein said reservoir or medium container may also mechanically support the load, and distribution of the load, through the use of a mechanical and/or electromechanical support structure. As a representative example, this may include a support frame. The container may be of various shapes, sizes, curvatures, and dimensions, and may be comprised of a variety of materials compositions (single, multiple, composites, etc.), of which may vary throughout. In some embodiments, it may comprise features such as films, drapes, membranes, bellows, etc. that may be insertable and removable, and/or fabricated within, of which may be used to conform to the patient and assist in confining/containing the medium within the container. It may further contain various sensors (e.g., volume/fill level), drains (e.g., inlet/outlet), lighting (e.g., LEDs), markings (e.g., fill lines, set up orientations, etc.), text (e.g., labeling), etc.

In one embodiment, the reservoir or medium container contains a sealable frame, of which a membrane and/or film may be positioned within, to afford a conformable means of contacting the reservoir (later comprising the treatment head/therapy transducer) as an interface to the patient, that further provides a barrier to the medium (e.g., water) between the patient and therapy transducer). In other embodiments, the membrane and/or film may comprise an opening, the patient contacting edge of which affords a fluid/mechanical seal to the patient, but in contrast allows medium communication directly with the patient (e.g., direct degassed water interface with patient). The superstructure of the reservoir or medium container in both these examples may further afford the proximal portion of the structure (e.g., top) to be open or enclosed (e.g., to prevent spillage or afford additional features).

Disclosed membranes may be comprised of various elastomers, viscoelastic polymers, thermoplastics, thermoplastic elastomers, thermoset polymers, silicones, urethanes, rigid/flexible co-polymers, block co-polymers, random block co-polymers, etc. Materials may be hydrophilic, hydrophobic, surface modified, coated, extracted, etc., and may also contain various additives to enhance performance, appearance or stability. In some embodiments, the thermoplastic elastomer may be styrene-ethylene-butylene-styrene (SEBS), or other like strong and flexible elastomers. The membrane form factor can be flat or pre-shaped prior to use. In other embodiments, the membrane could be inelastic (i.e., a convex shape) and pressed against the patient's skin to acoustically couple the transducer to the tissue. Systems and methods are further disclosed to control the level of contaminants (e.g., particulates, etc.) on the membrane to maintain the proper level of ultrasound coupling. Too many particulates or contaminants can cause scattering of the ultrasound waves. This can be achieved with removable films or coatings on the outer surfaces of the membrane to protect against contamination.

Said materials may be formed into useful membranes through molding, casting, spraying, ultrasonic spraying, extruding, and/or any other processing methodology that produces useful embodiments. They may be single use or reposable/reusable. They may be provided non-sterile, aseptically cleaned or sterile, where sterilization may comprise any known method, including but not limited to ethylene oxide, gamma, e-beam, autoclaving, steam, peroxide, plasma, chemical, etc. Membranes can be further configured with an outer molded or over molded frame to provide mechanical stability to the membrane during handling including assembly, set up and take down of the coupling sub-system. Various parameters of the membrane can be optimized for this method of use, including thickness, thickness profile, density, formulation (e.g., polymer molecular weight and copolymer ratios, additives, plasticizers, etc.), including optimizing specifically to maximize acoustic transmission properties, including minimizing impact to cavitation initiation threshold values, and/or ultrasound imaging artifacts, including but not limited to membrane reflections, as representative examples.

Open reservoirs or medium containers may comprise various methods of filling, including using pre-prepared medium or water, that may be delivered into the containers, in some cases to a defined specification of water (level of temperature, gas saturation, etc.), or they may comprise additional features integral to the design that allow filling and draining (e.g., ports, valves, hoses, tubing, fittings, bags, pumps, etc.). These features may be further configured into or to interface to other devices, including for example, a fluidics system. In some cases, the fluidics system may be an in-house medium preparation system in a hospital or care setting room, or conversely, a mobile cart-based system which can prepare and transport medium to and from the cart to the medium container, etc.

Enclosed iterations of the reservoir or medium container may comprise various features for sealing, in some embodiments sealing to a proximal/top portion or structure of a reservoir/container, or in other cases where sealing may comprise embodiments that seal to the transducer, or a feature on the transducer housings. Further, some embodiments may comprise the dynamic ability to control the volume of fluid within these designs, to minimize the potential for air bubbles or turbulence in said fluid and to allow for changes in the focal length to the target area without moving the transducer. As such, integrated features allowing fluid communication, and control of, may be provided (ability to provide/remove fluid on demand), including the ability to monitor and control various fluid parameters, some disclosed above. In order to provide this functionality, the overall system, and as part, the Coupling sub-system, may comprise a fluid conditioning system, which may contain various electromechanical devices, systems, power, sensing, computing, pumping, filtering and control systems, etc. The reservoir may also be configured to receive signals that cause it to deform or change shape in a specific and controlled manner to allow the target point to be adjusted without moving the transducer.

Coupling support systems may include various mechanical support devices to interface the reservoir/container and medium to the patient, and the workspace (e.g., bed, floor, etc.). In some embodiments, the support system comprises a mechanical arm with 3 or more degrees of freedom. Said arm may have a proximal interface with one or more locations (and features) of the bed, including but not limited to, the frame, rails, customized rails or inserts, as well as one or more distal locations of the reservoir or container. The arm may also be a feature implemented on one or more Carts, wherein Carts may be configured in various unlimited permutations, in some cases where a Cart only comprises the role of supporting and providing the disclosed support structure.

In some embodiments, the support structure and arm may be a robotically-enabled arm, implemented as a stand-alone Cart, or integrated into a Cart further comprising two or more system sub-systems, or where in the robotically-enabled arm is an arm of another robot, of interventional, surgical or other type, and may further comprise various user input features to actuate/control the robotic arm (e.g., positioning into/within coupling medium) and/or Coupling solution features (e.g., filling, draining, etc.). In some examples, the support structure robotic arm positional encoders may be used to coordinate the manipulation of the second arm (e.g., comprising the therapy transducer/treatment head), such as to position the therapy transducer to a desired/known location and pose within the coupling support structure.

Overall, significant unmet needs exist in interventional and surgical medical procedures today, including those procedures utilizing minimally invasive devices and approaches to treat disease and/or injury, and across various types of procedures where the unmet needs may be solved with entirely new medical procedures. Today's medical system capabilities are often limited by access, wherein a less or non-invasive approach would be preferred, or wherein today's tools aren't capable to deliver preferred/required tissue effects (e.g., operate around/through critical structures without serious injury), or where the physical set up of the systems makes certain procedure approaches less desirable or not possible, and where a combination of approaches, along with enhanced tissue effecting treatments, may enable entirely new procedures and approaches, not possible today.

In addition, specific needs exist for enabling histotripsy delivery, including robotic histotripsy delivery, wherein one or more histotripsy therapy transducers may be configured to acoustically couple to a patient, using a completely sealed approach (e.g., no acoustic medium communication with the patient's skin) and allowing the one or more histotripsy transducers to be moved within the coupling solution without impeding the motion/movement of the robotic arm or interfering/disturbing the coupling interface, which could affect the intended treatment and/or target location.

Disclosed herein are histotripsy acoustic and patient coupling systems and methods, to enable histotripsy therapy/treatment, as envisioned in any setting, from interventional suite, operating room, hybrid suites, imaging centers, medical centers, office settings, mobile treatment centers, and/or others, as non-limiting examples. The following disclosure further describes novel systems used to create, control, maintain, modify/enhance, monitor and setup/takedown acoustic and patient coupling systems, in a variety of approaches, methods, environments, architectures and work-flows. In general, the disclosed novel systems may allow for a coupling medium, in some examples degassed water, to be interfaced between a histotripsy therapy transducer and a patient, wherein the acoustic medium provides sufficient acoustic coupling to said patient, allowing the delivery of histotripsy pulses through a user desired treatment location (and volume), where the delivery may require physically moving the histotripsy therapy transducer within a defined work-space comprising the coupling medium, and also where the coupling system is configured to allow said movement of the therapy transducer (and positioning system, e.g., robot) freely and unencumbered from by the coupling support system (e.g., a frame or manifold holding the coupling medium).

Membranes/Barrier Films and Related Architectures

Membranes and barrier films may be composed of various biocompatible materials which allow conformal coupling to patient anatomy with minimal or no entrapped bubbles capable of interfering with ultrasound imaging and histotripsy therapy, and that are capable of providing a sealed barrier layer between said patient anatomy and the ultrasound medium, of which is contained within the work-space provided by the frame and assembly.

Membrane and barrier film materials may comprise flexible and elastomeric biocompatible materials/polymers, such as various thermoplastic and thermoset materials, as well as permanent or bioresorbable polymers. Additionally, the frame of the UMC can also comprise the same materials. In some examples, the membrane may be rigid or semi-rigid polymers which are pre-shaped or flat. Some non-limiting examples of materials from which the membrane and barrier film may be made include but are not limited to polyurethanes, polystyrene copolymers, poly(lactic acid), poly(glycolic acid), poly(hydroxybutyrate), poly(phosphazine), polyesters, polyethylene glycols, polyethylene oxides, polyacrylamides, polyhydroxyethylmethylacrylate, polyvinylpyrrolidone, polyvinyl alcohols, polyacrylic acid, polyacetate, polycaprolactone, polyethylene, polypropylene, polybutylene, aliphatic polyesters, glycerols, poly(amino acids), copoly(ether-esters), polyalkylene oxalates, polyamides, poly(iminocarbonates), polyalkylene oxalates, polyoxaesters, polyorthoesters, polyphosphazenes and copolymers, block copolymers, homopolymers, blends and combinations thereof. In some embodiments, the membrane is composed of polystyrene copolymers and block copolymers comprising ethylene, butadiene, butylene and/or additional styrene blocks, with examples including styrene-butadiene-styrene (SBS) and styrene-ethylene-butylene-styrene (SEBS). In other examples, they may be comprised of various silicone and silicone co-polymers, and/or formulations of various silicone compositions, including those with lower molecular weight silicones or silicone-based oils. They may further contain additives to enhance thermal or optical stability, mechanical properties, biological properties (e.g., anti-infectives, etc.), sterilization stability including steam, heat, chemical, radiation and/or e-beam stability, as well as various additives including oils or low molecule weight fluids to plasticize or soften materials, and/or improve adherence to other surfaces (e.g., backing materials, skin, etc.). In some embodiments, membranes/barrier films comprise 10-80% oil, in other embodiments, 40-60%, by weight %. In some cases the oil is a paraffin oil. In some embodiments, the additives also include blooming agents and/or other agents to enhance surface properties. Some membranes/barrier film compositions may also include adhesives, or one or more components, of an adhesive formulation to allow adherence of the membrane/film to the patients anatomy (e.g., skin), and restraint features, etc., aimed to prevent membrane "run away" from the body and/or frame/manifold.

Membranes/barrier films may vary in thickness from 0.01 mm to 7 mm, and in some embodiments are preferred to be between 1 and 5 mm. In some embodiments the membrane has a thickness between 2 mm and 4 mm, and in additional embodiments the membrane has a thickness of between 2.5 mm and 3.5 mm. The membranes can have a tensile strength of >0.2 MPa. In some embodiments, the tensile strength can be between 0.4 MPa and 1 MPa. The membranes can be configured to stretch or elongate by up to 200%, and in some embodiments by up to 500% or up to 3000%. Thickness may be selected to balance physio-mechanical properties, impact to acoustic cavitation/histotripsy threshold, conformance to patient anatomy and the degree of membrane elongation and displacement (based on set up position and anticipated ultrasound medium volume and relative spatial distribution). They may be transparent or translucent, and/or may be colored or tinted, including being completely colored or tinted, or partially, and as markings or continuous/discrete regions. In some examples, membranes are preferably transparent/translucent to allow visibility of work-space and any potential air bubbles present in the ultrasound medium and the sealed system, as well as visualizing the ultrasound imaging probe comprised within the central bore of the therapy transducer. This may include, as an example, viewing the probe and its position/orientation (e.g., if translated out onto the skin and/or if retracted back off the skin).

Membranes/barrier films may further contain a structural component, such as a frame or fixture, that may further improve the handling and ease of use of the acoustic and patient coupling system, including but not limited to, procedure set up and take down, and without comprising acoustic window size. Frames may be comprised of biocompatible metals and/or polymers, including but not limited to, aluminum, aluminum alloys, acrylonitrile butadiene styrene (ABS), polyethylene, propylene, polyamides, and/or other impact resistant materials. The disclosed frame may be positioned along an edge contour of the membrane/barrier film, of which may be continuous or in segments/lengths. As a representative example, the frame is located along the outer edge contour of the membrane. The frame may be positioned (e.g., over molded membrane) within the membrane/barrier film, or conversely, may be comprised with on the membrane/barrier film, wherein the frame is molded around the membrane. As such, disclosed concepts may provide one or more means of interfacing to membrane/barrier films, wherein said interfaces include "hard", "semi-hard", and/or "soft" interfaces, or combinations of. For example, creating a seal along exposed/revealed soft membrane/barrier film surfaces and edge surfaces, versus sealing and interfacing along hard membrane frames to larger system "frames and assemblies" described below. Further, interfaces may comprise various features to enhance mechanical joining, mating, fit, interlocking and/or sealing, and may include, but not limited to, mechanical ridges, grooves, pins, key and interlocking structures, of which may be prepared in various heights, depths, grading/pitch, tapers, angles, stand-offs, shapes, spacings, frequency/amount, and/or cut-outs. In some examples, the membrane/barrier film may comprise a window for direct physical/acoustic access, wherein the edge region of the window (e.g., cut out) may be adhered to the patient and where said edge region acts as the "mechanical support interface and frame-like feature."

The membrane/barrier film frame may be made of various shapes and dimensions/sizes to accommodate various work-spaces and work-space volumes as provided by the coupling system, and for/from smaller (<5 cm) to larger (>20 cm in long axis) transducers and related required travel space to accommodate location/pose, and set up and target anatomical locations (e.g., abdominal, neuro, etc.), where varied acoustic windows and conformal anatomical contouring of (conforming with abdomen, thorax/chest, head/neck, extremities, etc.), are desired. Frames may be constructed from various metals, alloys, polymers/plastics, ceramics and/or composites and combinations of, and using casting, molding, machining and/or any useful/known fabrication method. In some embodiments, they are preferably aluminum. In other embodiments they are an injection molded plastic derived from the list above.

Overall, the disclosed membrane physio-mechanical, chemical, dimensional and processing derived characteristics/properties afford the ability to control, and in some cases, minimize acoustic cavitation initiation (histotripsy) threshold requirements, as compared to other membranes. In some embodiments, membranes and barrier films may increase cavitation thresholds (and required drive amplitude) by 50% or more (over thresholds obtained directly through skin and coupled using degassed water). In other embodiments, 10-50%, as tested in similar fashion. In other embodiments, membranes/barrier films increase threshold requirements around 10%, and in preferred embodiments, they increase threshold requirements no more than 5-10%. In some embodiments, they also afford this capability without diminishing clinically relevant ultrasound imaging properties. In other embodiments, the window, as detailed previously, may afford no change in threshold given the direct acoustic access through skin. This may include B-mode or other forms of ultrasound imaging or post-acquisition image enhancements, some of which may be used to further enable multi-modal image reconstruction, segmentation, registration and fusion (with MRI, CT, cone beam CT, fluoroscopy, and forms of augmented fluoroscopy, etc.).

The therapy ultrasound systems described herein typically operate with a threshold voltage (to produce effective acoustic cavitation and histotripsy) which is as low as reasonable possible, and which is capable of effective operation at a maximum penetration depth.

The use of a membranes described herein has advantages such as improving ease of use, enabling better targeting of difficult tissue locations in the patient and improved patient comfort. However, a membrane has the disadvantage that it places additional material layers between the therapy transducer and the skin of the patient. These additional layers—specifically the membrane—have two potential effects: transmission loss and aberration.

Transmission loss refers to how much of the ultrasound energy is coupled through the membrane-which is a function of the thickness, speed of sound, acoustic impedance and how well we can get a bubble free interface in the membrane and in the gel or oil layer which is used between the membrane and the tissue. The membranes address the transmission effects by having an acoustic impedance close to that of water/tissue while keeping thin enough that losses in the membrane itself are minimal. The contact is achieved through a combination of having a very high compliance which lets the membrane conform to the body, the self-wetting nature of the oil infused material and the application technique (bubble swipe) that allows us to control the interface.

Managing the level of aberration can be achieved by having a similar speed of sound for the media and the membrane and by keeping the membrane as thin as possible. The level of aberration is likely to be dominated by the speed of sound differential between the coupling media (e.g., water) and the tissue.

The properties of the membrane which will affect the level of transmission loss and aberration are related to the raw material properties (composition and additives), the design of the membrane (e.g., membrane thickness, cross-section and surface roughness), the manufacturing process and the method for deploying the membrane onto the patient so that a sufficiently large and effective contact area is generated.

The membrane raw material can be selected to have an acoustic impedance as close as possible to that of the ultrasound media and should be biocompatible as well as being compatible with the ultrasound media and gels and oils used on the patient skin. The membrane materials can also provide sufficient temperature resistance (e.g., use of antioxidants to enable the material to survive high temperatures in the final manufacturing process) and environmental resistance during storage. The material should also not contain have additives which might reduce the ultrasound transmission (such as particulates, which could scatter the ultrasound). Other material properties which may provide application advantages are a high level of transparency (to enable visualization of bubbles through the membrane), good puncture resistance (safety), avoidance of absorbance of the ultrasound media (e.g., water) and a low bubble containment. Materials such as SEBS, which can leach/bloom mineral oil to the surface, may improve the quality of the contact between the membrane and any oils or gels used on the patient skin (i.e., this should reduce the risk of trapped bubbles). However, the level of any leached/bloomed material must be safe to handle and not contaminate the ultrasound media.

The mechanical properties and design of the membrane needs to be specified in order to create a sufficiently large area of effective ultrasound coupling between the ultrasound transducer and the patient skin. The area of contact should include no trapped air or air bubbles (which would cause transmission loss) and it should not apply loading to the patient which could cause discomfort or injury or unduly change the position of the internal organs. The cross-section of the membrane in the patient contact area should be constant to avoid variable transmission loss. The structural stiffness of the material should be low enough so that the material is in tension at all times during contact with the patient's skin in order to prevent creasing, folding or wrinkling of the skin which could trap air. The preferred embodiment is a flat membrane which stretches during filling to be convex and provides an initial, single contact point with the patient. As this membrane is lowered or further expanded/ filled, the skin contact increases radially, largely preventing the formation of trapped air pockets. Alternatively, a pre-shaped, convex membrane could be used but a risk is that this embodiment may not have sufficient material tension at either the initial contact point or during the deployment phase.

The manufacturing process also has an impact on the presence of air bubbles in the material, particulates and contamination of the material, material composition variance, variability in membrane thickness and on surface roughness and surface defects. All of the above could potentially increase transmission losses.

Frames and Assemblies

Coupling solution frames and assemblies, in some cases referred to as an ultrasound medium container (UMC), coupling solution, and/or coupling device, are generally configured to retain, seal and support the membrane/barrier film as well as allow/provide interfaces to 1) an upper boot (e.g., upper enclosure/seal), 2) fluid inlets/outlets (e.g., receive/remove ultrasound medium), 3) mechanical arm(s), as well as 4) other features including/for, but not limited to, membrane supports/constraints, handles, locking mechanisms (for membrane frame, boots, frame/assembly pieces), venting and bubble management, imaging probe controls, etc. In some examples, the frame may incorporate pressure sensors configured to measure the pressure of the medium within the UMC, which can be used to detect leaks or over-pressure events. The UMC may further include pressure relief valves.

Ultrasound Medium

As previously described, the ultrasound medium may comprise any applicable medium capable of providing sufficient and useful acoustic coupling to allow histotripsy treatments and enable sufficient clinical imaging (e.g., ultrasound). Ultrasound mediums, as a part of this disclosure and system, may comprise, but are not limited to, various aqueous solutions/mediums, including mixtures with other co-soluble fluids, of which may have preferred or more preferred acoustic qualities, including ability to match speed of sound, etc. Example mediums may comprise degassed water and/or mixtures/co-solutions of degassed water and various alcohols, such as ethanol.

Mechanical Support Arms and Arm Architectures

In order to support the acoustic and patient coupling system, including providing efficient and ergonomic workflows for users, various designs and configurations of mechanical support arms (and arm architectures) may be employed. Support arms may be configured with a range of degrees of freedom, including but not limited to allowing, x, y, z, pitch, roll and yaw, as well additional interfacing features that may allow additional height adjustment or translation.

Arms may comprise a varied number and type of joints and segments. Typically, arms may comprise a minimum of 2 segments. In some configurations, arms may comprise 3 to 5 segments.

Arms are also be configured to interface proximally to a main support base or base interface (e.g., robot, table, table/bed rail, cart, floor mount, etc.) and distally to the frame/assembly and overall "UMC" or "coupling solution". This specific distal interface may further include features for controlling position/orientation of the frame/assembly, at the frame/assembly interface.

For example, in some embodiments, the arm/frame interface may comprise a ball joint wrist. In another example, the interface may include use of a gimbal wrist or an adjustable pitch and roll controlled wrist. These interfaces may be further employed with specific user interfaces and inputs, to assist with interacting with the various wrists, of which may include additional handles or knobs (as an unlimited example), to further enable positioning the UMC/coupling solution. For example, a gimbal wrist may benefit from allowing the frame/assembly to have 3 degrees of freedom (independent of the arm degrees of freedom), including pitch, roll and yaw adjustments.

Support arms, configured with arm wrists, further interfaced with frames/assemblies, may comprise features such as brakes, including cable or electronic actuated brakes, and quick releases, which may interact with one or more axis, individually, or in groupings. They may also include electronic lift systems and base supports. In some embodiments, these lift systems/base supports are co-located with robot arm bases, wherein said robot arm is equipped with the histotripsy therapy transducer configured to fit/work within the enclosed coupling solution. In other embodiments, the support arm is located on a separate cart. In some cases, the separate cart may comprise a fluidics system or user console. In other embodiments, it is interfaced to a bed/table, including but not limited to a rail, side surface, and/or bed/table base. In other examples/embodiments, it is interfaced to a floor-based structure/footing, capable of managing weight and tipping requirements.

Fluidics Systems, Control Systems and System Architectures

As a part of overall fluidics management, histotripsy systems including acoustic/patient coupling systems, may be configured to include an automated fluidics system, which primarily is responsible for providing a reservoir for preparation and use of coupling medium, where preparation may include the ability to degas, chill, monitor, adjust, dispense/fill, and retrieve/drain coupling medium to/from the frame/assembly. The fluidics system may include an emergency high flow rate system for rapid draining of the coupling medium from the UMC. In some embodiments, the fluidics system can be configured for a single use of the coupling medium, or alternatively, for re-use of the medium. In some embodiments, the fluidics system can implement positive air pressure or vacuum to carry out leak tests of the UMC and membrane prior to filling with a coupling medium. Vacuum assist can also be used for removal of air from the UMC during the filling process. The fluidics system can further include filters configured to prevent particulate contamination from reaching the UMC.

What is claimed is:

1. An ultrasound treatment head, comprising:

a therapy transducer array configured to deliver ultrasound pulses to a focal location;

a bore located within the therapy transducer array;

a coupling assembly sized and configured for axial and rotational movement within the bore of the therapy transducer array;

an ultrasound imaging probe coupled to the coupling assembly;

a first user input device configured to control axial movement of the ultrasound imaging probe relative to the therapy transducer array; and a second user input device configured to control rotational movement of the ultrasound imaging probe relative to the therapy transducer array, the second user input device comprising a rotational sleeve disposed around the coupling assembly, the rotational sleeve being keyed to the coupling assembly, wherein manual rotation of the rotational sleeve results in a corresponding rotational movement of the ultrasound imaging probe;

further comprising a keyed plate configured to rotate with rotation of the ultrasound imaging probe.

2. The ultrasound treatment head of claim 1, further comprising at least one encoder configured to track an axial position and a rotational position of the ultrasound imaging probe relative to the therapy transducer array.

3. The ultrasound treatment head of claim 2, further comprising one or more processors configured to register the axial position and rotational position of the ultrasound imaging probe with a digital treatment plan.

4. The ultrasound treatment head of claim 2, wherein the at least one encoder is in electrical communication with one or more remote processors configured to register the axial position and rotational position of the ultrasound imaging probe with a digital treatment plan.

5. The ultrasound treatment head of claim 4, wherein the digital treatment plan further comprises at least one of a target contour and a margin contour.

6. The ultrasound treatment head of claim 1, wherein the first user input device further comprises:

an image probe control;

a first shaft coupled to the image probe control;

a first gear coupled to the first shaft;

a second gear coupled to the first gear;

a second shaft coupled to the second gear;

a shuttle assembly coupled to the coupling assembly and configured to move axially along the second shaft when the second shaft is rotated;

wherein manipulation of the image probe control results in a corresponding axial movement of the ultrasound imaging probe along a length of the second shaft.

7. The ultrasound treatment head of claim 1, further comprising one or more detents positioned against the rotational sleeve at specified rotational angles of the ultrasound imaging probe relative to the therapy transducer array to provide tactile feedback to a user when the ultrasound imaging probe is rotated to the specified rotation angles.

8. The ultrasound treatment head of claim 1, wherein the rotational sleeve further includes two tabs disposed 180 degrees apart which align with an imaging plane of the ultrasound imaging probe.

9. The ultrasound treatment head of claim 1, further comprising one or more bushings configured to align an outer diameter of the coupling assembly with an inner diameter of the bore.

10. The ultrasound treatment head of claim 1, further comprising a position sensor configured to determine when the ultrasound imaging probe is in a retracted position.

11. The ultrasound treatment head of claim 10, further comprising one or more processors in electrical communication with the position sensor configured to prevent initiation of therapy with the therapy transducer array if the position sensor determines that the ultrasound imaging probe is not in a specified position with respect to the therapy transducer array.

12. The ultrasound treatment head of claim 11, wherein the specified position comprises fully retracted within the ultrasound treatment head.

13. The ultrasound treatment head of claim 11, wherein the specified position comprises positioned so as to not obstruct or substantially obstruct the therapy transducer array.

14. The ultrasound treatment head of claim 1, further comprising a rotational encoder coupled to the keyed plate, wherein a rotor of the rotational encoder rotates with rotation of the keyed plate and a stator of the rotational encoder remains static during rotation of the keyed plate.

15. The ultrasound treatment head of claim 14, further comprising a grip base disposed over the keyed plate and configured to couple to the therapy transducer array.

16. The ultrasound treatment head of claim 14, further comprising one or more handles, wherein at least one handle is hollow to allow for routing of a wire from the rotational encoder to a processor.

17. The ultrasound treatment head of claim 1, further comprising a quick-release connector configured to couple a robotic positioning arm to the ultrasound treatment head.

18. The ultrasound treatment head of claim 17, wherein the quick-release connector includes mating features configured to interface with corresponding mating features on the robotic positioning arm.

19. The ultrasound treatment head of claim 1, further comprising a visual indicator configured to indicate a maximum insertion depth of the ultrasound treatment head into a coupling medium.

20. The ultrasound treatment head of claim 19, wherein the visual indicator comprises a notch feature in the rotational sleeve.

21. The ultrasound treatment head of claim 20, wherein a position of the notch feature on the ultrasound treatment head for indicating the maximum insertion depth is selected to protect one more electronic components in the ultrasound treatment head.

* * * * *